United States Patent [19]

Ménard et al.

[11] 4,068,080
[45] Jan. 10, 1978

[54] O-2-ISOCEPHEM-4-CARBOXYLIC ACID DERIVATIVES AS ANTIBACTERIAL AGENTS

[75] Inventors: Marcel Ménard; Gary M. F. Lim, both of Candiac; Terry T. Conway, Brossard, all of Canada

[73] Assignee: Bristol-Myers Company, New York, N.Y.

[21] Appl. No.: 715,956

[22] Filed: Aug. 19, 1976

Related U.S. Application Data

[62] Division of Ser. No. 567,323, April 11, 1975, Pat. No. 4,011,216.

[51] Int. Cl.$^2$ .................. C07D 265/34; C07D 413/12; C07D 417/12
[52] U.S. Cl. .................................................. 544/105
[58] Field of Search ..................... 260/244 R

[56] References Cited

U.S. PATENT DOCUMENTS

3,835,130  9/1974  Woodward .................. 260/243 C

FOREIGN PATENT DOCUMENTS

| | | |
|---|---|---|
| 2,046,822 | 3/1972 | Germany. |
| 2,046,823 | 3/1972 | Germany. |
| 2,046,824 | 3/1972 | Germany. |
| 2,355,209 | 3/1974 | Germany. |
| 1,377,715 | 12/1974 | United Kingdom. |

OTHER PUBLICATIONS

Brunwin et al., J. Chem. Soc. Chem. Comm., 865–867 (1971).
Brunwin et al., J. Chem. Soc. Chem. Comm., 589–590 (1972).
Brunwin et al., J. Chem. Soc. (c) 3756–3762 (1971).
Wolfe et al., Can. J. Chem., 50, 2894–2905 (1972).
Kukolja, J.A.C.S. 93, 6267–6270 (1971).
Kukolja, J.A.C.S. 94, 7590–7593 (1972).
Lowe, et al., J. Chem. Soc. Perkins I, 1321–1328 (1973).
Luttringer et al., Tetrahedron Letters, 4163–4166 (1973).
Sheehan et al., J. Heterocycl. Chem., 5, 779–783 (1968).
Mukerjee et al., Synthesis, 327–346 (1973).

*Primary Examiner*—Jane S. Myers
*Attorney, Agent, or Firm*—David M. Morse

[57] ABSTRACT

There is described the stereoselective total synthesis of novel $\Delta^{2,3}$-1,4-morpholine-2-carboxylic acids possessing a fused $\beta$-lactam ring in the 1, 6-position and carrying a substituent cis to carbon 5 in the 7-position of the fused ring system represented by the general formula

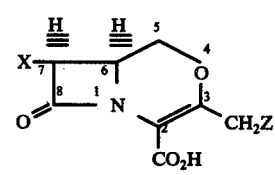

wherein Z is halo, hydroxyl, etherified hydroxyl or hydroxyl esterified with a carboxylic acid residue or a sulfonic acid residue and X is amino, azido or acylamino. Also included in the invention are compounds of formula I in which the carbonyl group at the 2-position is protected as by an easily cleavable ester group and salts of both the free acids and carboxyl-protected compounds of formula I. The compounds of formula I are potent antibacterial agents or are of use as intermediates in the preparation of such antibacterial agents.

9 Claims, No Drawings

O-2-ISOCEPHEM-4-CARBOXYLIC ACID DERIVATIVES AS ANTIBACTERIAL AGENTS

CROSS-REFERENCE TO RELATED APPLICATION

This is a divisional application of co-pending application Ser. No. 567,323, filed Apr. 11, 1975 now U.S. Pat. No. 4,011,216.

BACKGROUND OF THE INVENTION

1. Field of the Invention.

The chemical processes of the present invention produce novel antibacterial agents of the β-lactam type containing a hitherto unknown nucleus and useful intermediates for their synthesis.

2. Description of the Prior Art.

Penicillins and cephalosporins comprise a group of well-known antibacterial agents commonly grouped together as a class called β-lactam antibiotics. For a recent review of this field with many citations (especially the first ten) to the prior work, see J. P. Hou and J. W. Poole, β-lactam Antibiotics: Their Physicochemical Properties and Biological Activities in Relation to Structure, J. Pharmaceutical Sciences, 60(4), 503–532 (April, 1971). Most of the work in this field has fundamentally been done, speaking broadly, with 6-aminopenicillanic acid, 7-aminocephalosporanic acid and derivatives thereof produced by fermentation or chemical transformation of the natural products. Despite the extensive progress made in preparing active derivatives of 6-aminopenicillanic acid and 7-aminocephalosporanic acid, there is a continuing search for synthetic and semi-synthetic routes to new families of β-lactam antibiotics which may possess more advantageous properties then those derived from the known penicillin and cephalosporin nuclei.

Considerable work has been done on total chemical synthesis of both known β-lactams and nuclear analogs of such known compounds. A recent review is the text by M. S. Manhas and A. K. Bose, Synthesis of Penicillin, Cephalosporin C and Analogues, Marcel Decker, Inc., 95 Madison Avenue, New York, New York, 1969. Another extensive review is by R. B. Morin and B. G. Jackson, Chemistry of Cephalosporin Antibiotics, Fortschr. Chem. Org. Naturst., 28, 343–403 (1970), especially pages 379–393; the now famous "Woodward Intermediate" is shown therein as compound 146 on page 387. A more recent review of β-lactams is that by M. S. Manhas and A. K. Bose, Beta-Lactams: Natural and Synthetic: Part 1, Wiley-Interscience, New York, New York, 1971. A still further review article on the synthesis of β-lactams is that by A. K. Kokerjee et al., Synthesis, 327 (1973).

Other pertinent publications relating to synthesis of β-lactams are:

a. D. M. Brunwin, G. Lowe and J. Parker, J.C.S. Chem. Comm., 1971, 865–867, describing synthesis of nuclear analogs of the penicillin-cephalosporin group.

b. D. M. Brunwin et al., J. Chem. Soc. (C), 1971, 3756–3762 and J.C.S. Chem. Comm., 1972, 589–590 describing total synthesis of nuclear analogs of penicillins and cephalosporins.

c. S. Kukolja, J. Amer. Chem. Soc., 93, 6267–6270 (1971) and 94, 7590–7593 (1972) describing preparation of 6-phthalimido-5-epipenicillanates and disulfide analogs of penicillins.

d. J. A. Webber et al., J. Medicinal Chemistry, 14(11), 1136–1138 (1971) describing preparation of 3-cyanomethyl cephem nucleus.

e. West German Patent Specification No. 2,219,601 (Farmdoc 76,051T) describing synthesis of β-lactams of the formula $$X-CH-CH \overset{A}{\diagdown} \underset{R^3}{\overset{R^1}{\underset{|}{C-R^2}}} \\ O=C-N-C-COOH$$

wherein X is halo, $N_3-$ or $H_2N-$, A is $-S-$, $-S-CH_2-$, $-O-$, $-O-CH_2-$, $-CH_2$, $-CH_2CH_2-$ or $-NH-$ and $R^1$, $R^2$ and $R^3$ are hydrogen, $C_1-C_6$ alkyl or aryl.

f. U.K. Patent 1,308,822 disclosing β-lactams of the formula $$Y-CH-CH \overset{S}{\diagdown} CH_2 \\ CO-N \diagdown CO \\ C \\ \| \\ CH_3 / C \diagdown CH_3$$

where Y = amino or substituted amino.

g. S. Wolfe et al., Can. J. Chem., 50, 2894–2905 (1972) describing synthesis of sulfur-free penicillin derivatives.

h. French Patent No. 2,111,859 describing nuclei of the formula $$H_2N \diagdown \overset{S}{\diagdown} CH_2 \\ -N \diagdown CH \\ O \diagup C \\ O=C-O-R^2$$

and 7-acylated derivatives thereof.

i. Helvetica Chimica Acta, 55(2), 388–429 (1972) describing nuclear modified cephalosporins and penicillins.

j. F. Moll et al., Zeit. fur Naturforsch. B, 27(b)6, 727 (1972) describing nuclear analogs of cephalosporins.

k. U.K. Pat. Specifications Nos. 1,271,013 and 1,271,014 describing γ-lactams of 7-(acylamino)-3-aminomethyl-ceph-3-em-4-carboxylic acids.

l. U.K. Pat. Specification No. 1,271,180 describing preparation of novel thiazoline azetidinone rearrangement products useful as intermediates in penicillin and cephalosporin synthesis.

m. German Patent Specifications Nos. 2,046,822, 2,046,823 and 2,046,824 describing synthesis of novel azetidinone intermediates.

n. G. Lowe et al., J. Chem. Soc. Perkins I, 1322 (1973) describing total synthesis of nuclear analogs of 7-methylcephalosporins having the formula o. D. M. Brunwin et al., J. Chem. Soc. Chem. Comm., 865 (1971) describing synthesis of compounds of the formula

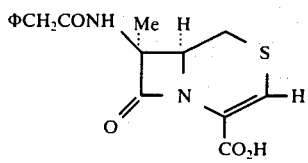

p. S. Wolfe et al., Canadian J. Chem., 50, 2902 (1972) describing compounds of the formula

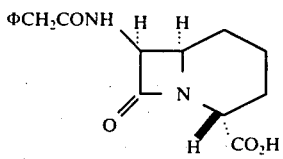

q. J. P. Luttringer et al., Tetrahedron Letters, 4163-4166 (1973) describing compounds of the formula

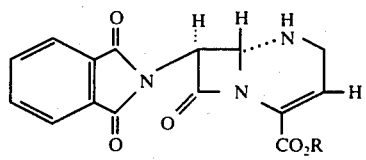

r. U.S. Pat. No. 3,835,130 disclosing β-lactams of the formula

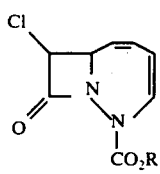

wherein $R_a$ and $R_b$ are each hydrogen or $R_a$ and $R_b$ form a covalent carbon-to-carbon bond, $R_1'$ represents hydrogen, $R_1''$ is cyanoacetyl, bromacetyl or an acyl group of the formula

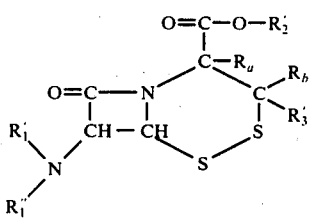

in which Ar is phenyl, 3-hydroxyphenyl, 4-hydroxyphenyl, 3-chloro-4-hydroxyphenyl, 3,5-dichloro-4-hydroxyphenyl or 2-thienyl, $R_2'$ is hydrogen and $R_3'$ is hydrogen or lower alkyl.

s. West German Offenlegungsschrift No. 2,355,209 describing synthesis of β-lactams of the formula

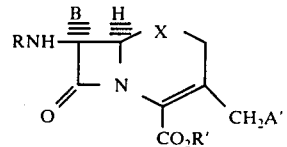

wherein R is acyl, A' is hydrogen, hydroxy, carbamoyloxy, thiocarbamoyloxy, quaternary ammonium, N-lower alkyl carbamoyloxy, N,N-di-lower alkyl carbamoyloxy, N-lower alkylthio and N,N-diloweralkyl-thiocarbamoyloxy, azido, halo, cyano, a tertiary amine, acyloxy, or a 5-member heterocyclic thio group having 1-4 hetero atoms; B is H, $OCH_3$ or SR where R is lower alkyl or aryl; X is a divalent radical selected from —O—, —$CH_2$— or —NY— where Y is hydrogen, lower alkyl, formyl or benzyl and R' is hydrogen or a protecting group.

SUMMARY OF THE INVENTION

The present invention provides stereoselective total synthesis of certain novel substituted Δ$^{2,3}$-1,4-morpholine-2-carboxylic acids possessing a fused β-lactam ring in the 1,6-position and carrying a substituent cis to carbon 5 in the 7-position of the fused ring system represented by the general formula

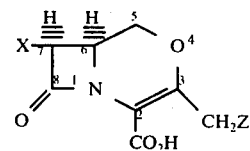

wherein Z is halo, hydroxyl, etherified hydroxyl or hydroxyl esterified with a carboxylic or a sulfonic acid residue and X is azido, amino or acylamino. When X is acylamino, these acids (and their pharmaceutically acceptable salts and physiologically hydrolyzed esters) are potent antibacterial agents.

Also included in this invention are various novel intermediates useful in preparing the active β-lactam derivatives described above and various processes for the production of the intermediates and active compounds.

The compounds having the above general formula represent a new family of β-lactam antibiotics. They can be considered nuclear analogs of cephalosporins in which the sulfur atom of the dihydrothiazine ring is replaced by an oxygen atom and shifted from position 5 to position 4 of the β-lactam ring system as numbered in the formula above. The nomenclature to be used could be the following:

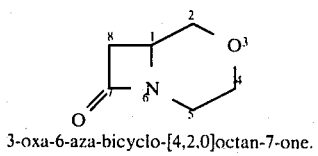

3-oxa-6-aza-bicyclo-[4,2.0]octan-7-one.

However, Sheehan has used the term 0-cephem for the structure

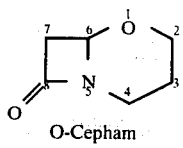

O-Cepham

[J. C. Sheehan and M. Dadic, J. Heterocyclic Chem., 5, 770 (1968)] and we propose the use of the term 0-2-isocephem for the basic system having the formula

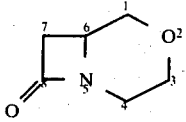

The numerical prefix indicates the position of the hetero-atom.

To illustrate the above system, the intermediate of the formula

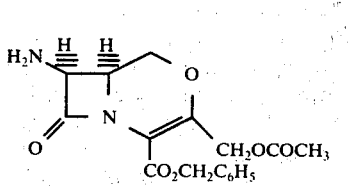

may be named benzyl 7β-amino-3-acetoxymethyl-Δ³-0-2-isocephem-4-carboxylate and the compound of the formula

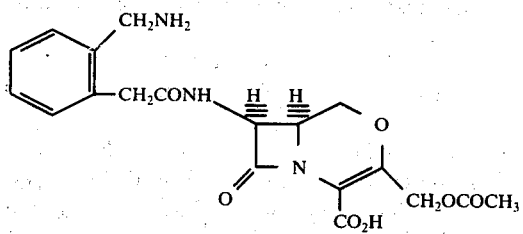

may be named 7β-(2-aminomethylphenylacetamido)-3-acetoxymethyl-Δ ³-0-2-isocephem-4-carboxylic acid.

There is thus provided by the present invention the novel 0-2-isocephem compounds having the formula

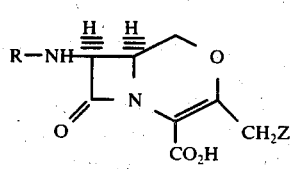

II wherein R is an acyl group and Z is halo, hydroxyl, hydroxyl esterified with a carboxylic acid or a sulfonic acid residue or etherified hydroxyl, and easily cleavable esters and pharmaceutically acceptable salts of said acids and esters.

The acyl group R can be chosen from a wide variety of organic acyl radicals which yield products of improved properties and is preferably an acyl radical which is contained in a naturally occurring or biosynthetically, semi-synthetically or totally-synthetically produced pharmacologically active N-acyl derivative of 6-aminopenicillanic acid or 7-aminocephalosporanic acid. Examples of suitable acyl groups are defined in the following general formulae, but it should be noted that this is not intended to be an exhaustive list of all the possible acyl groups which may be used.

i. $R^a C_n H_{2n} CO-$ where $R^a$ is aryl (carbocyclic or heterocyclic), substituted aryl, cycloalkyl, substituted cycloalkyl, cycloalkenyl, substituted cycloalkenyl or a nonaromatic or mesoionic heterocyclic group, and n is an integer from 1-4. The preferred $R^a$ substituents are (a) aryl selected from phenyl, 2-thienyl, 3-thienyl, furyl, 4-isoxazolyl, pyridyl, tetrazolyl, sydnone-3 or -4, imidazolyl, naphthoyl, quinoxalinyl, triazolyl, isothiazolyl, thiadiazolyl, thiazolyl, oxazolyl, oxadiazolyl, pyrazolyl, furazan, pyrazinyl, pyrimidinyl, pyridazinyl or triazinyl; (b) substituted aryl in which the aryl groups mentioned above under (a) are substituted by one or more radicals selected from chloro, bromo, iodo, fluoro, nitro, amino, cyano, (lower)alkanoyloxy, (lower)-alkanoyl, (lower)alkoxyamino, (lower)alkoxy, (lower)-alkyl, (lower)alkylamino, hydroxy, guanidino, (lower)-alkylthio, carboxy, phenyl, halophenyl, trifluoromethyl, di(lower)alkylamino, sulfamyl, (lower)alkanoylamino, phenyl(lower)alkylamido, cycloalkylamino, allylamido morpholinocarbonyl, pyrrolidinocarbonyl, piperidinocarbonyl, tetrahydropyridino, furfurylamido or N-alkyl-N-anilino; (c) $C_3-C_{12}$ cycloalkyl; (d) substituted $C_3-C_{12}$ cycloalkyl where the substituents are one or more radicals selected from chloro, bromo, fluoro, iodo, nitro, trifluoromethyl, $C_1-C_4$ alkyl, $C_1-C_4$ alkylamino, $C_1-C_2$ alkoxy or amino; (e) $C_3-C_{12}$ cycloalkenyl, said cycloalkenyl group having 1 or 2 double bonds; and (f) substituted $C_3-C_{12}$ cycloalkenyl, said cycloalkenyl group having 1 or 2 double bonds and being substituted by one or more radicals selected from chloro, bromo, fluoro, iodo, nitro, trifluoromethyl, $C_1-C_4$ alkyl, $C_1-C_4$ alkylamino, $C_1-C_2$ alkoxy or amino. The most preferred $R^a$ groups are phenyl; phenyl substituted by one or more radicals selected from chloro, bromo, iodo, fluoro, nitro, amino, (lower)alkyl, guanidino, (lower)alkylthio, cyano, (lower)-alkoxy, sulfamyl, (lower)alkylamino, hydroxy, acetoxy, or trifluoromethyl; 2-thienyl; 3-thienyl; tetrazolyl; sydnone -3; sydnone -4; furyl; isothiazolyl; thiadiazolyl optionally substituted with phenyl; oxadiazolyl optionally substituted with phenyl; thiazolyl; imidazolyl; triazolyl; oxazolyl; pyridyl; furazan optionally substituted at the 3-position with methoxy; 4-isoxazolyl optionally substituted at the 5-position with methyl and at the 3-position with phenyl or halophenyl; 1,4-cyclohexadienyl; 1-cyclohexenyl and 1-aminocyclohexyl.

The most preferred acyl groups of this category are those in which n is 1. Examples of this category include phenylacetyl, halophenylacetyl, nitrophenylacetyl, aminophenylacetyl, β-(o-aminomethylphenyl)propionyl, (lower)alkanoyloxyphenylacetyl (e.g. p-acetoxyphenylacetyl), (lower)alkoxyphenylacetyl (e.g. methoxyphenylacetyl, ethoxyphenylacetyl), (lower)alkylphenylacetyl (e.g. methylphenylacetyl or ethylphenylacetyl), hydroxyphenylacetyl (e.g. o-hydroxyphenylacetyl), (lower)alkylaminophenylacetyl (e.g. o-, m- or p-aminomethylphenylacetyl), o- m- or p-guanidinophenylacetyl, o-carboxyphenylacetyl, N,N-bis-(2-chloroethyl)aminophenylpropionyl, thien-2 and 3-ylacetyl, 2- or 3-furylacetyl, 1,2,5-thiadiazole-3-acetyl, isothiazolyl-4-acetyl, 4-isoxazolylacetyl, 1-cyclohexenylacetyl, 2-aminomethyl-1-cyclohexenylacetyl, 1-aminocyclohexylacetyl, 1,4-cyclohexadienylacetyl, 2-aminomethyl-1,4-cyclohexadienylacetyl, pyridylacetyl, tetrazolylacetyl (other heterocyclic groups of this type are disclosed in U.S. Pat. No. 3,819,623 and 3,516,997) or a sydnoneacetyl group as disclosed in U.S. Pat. No. 3,681,328, 3,530,123 and 3,563,983. Other groups of this type include 3-phenyl-5-chlorophenyl-5-methylisoxazol-4-ylacetyl and 3-(2,6-dichlorophenyl)-5-methylisoxazol-4-ylacetyl or a group in which isoxazolyl is replaced by isothiazole as disclosed in U.S. Pat. No. 3,551,440. Still other examples are o-, m- and p-(2'-aminoethoxy)phenylacetyl (as disclosed in U.S. Pat. No. 3,759,905), 4,5-dimethoxycarbonyl-1,2,3-triazol-1-ylacetyl or 4-cyano-1,2,3-triazol-1-yl-acetyl (as disclosed in U.S. Pat. No. 3,821,206) and imidazol-(1)-acetyl (as disclosed in U.S. Pat. No. 3,632,810;

ii. $C_nH_{2n+1}CO-$ where $n$ is an integer from 1–7. The alkyl group may be straight or branched and, if desired, may be interrupted by an oxygen or sulphur atom or substituted by, e.g., a cyano group. Examples of this group include cyanoacetyl, valeryl, hexanoyl, heptanoyl, ethoxycarbonyl, octanoyl and butylthioacetyl. A preferred acyl group is cyanoacetyl;

iii. $C_nH_{2n-1}CO-$ where $n$ is an integer from 2–7. The alkenyl group may be straight or branched and, if desired, may be interrupted by an oxygen or sulphur atom. An example of this group is allylthioacetyl;

(iv)

where $R^a$ is as defined under (i) and in addition may be benzyl, $C_1-C_6$ alkyl or (lower)alkoxycarbonyl and $R^b$ and $R^c$ which may be the same or different each represent hydrogen, phenyl, benzyl, phenethyl or $C_1-C_6$ alkyl. The preferred $R^a$ substituents in this category are benzyl, $C_1-C_6$ alkyl, (lower)alkoxycarbonyl and those mentioned under (i) as being preferred aryl, substituted aryl, cycloalkyl (and substituted cycloalkyl) and cycloalkenyl (and substituted cycloalkenyl) groups. The most preferred $R^a$ group is phenyl. Examples of this group include phenoxyacetyl, 2-phenoxy-2-phenylacetyl, 2-phenoxypropionyl, 2-phenoxybutyryl, benzyloxyacetyl, 2-methyl-2-phenoxypropionyl, p-cresoxyacetyl, p-methylthiophenoxyacetyl and ethoxycarbonylacetyl;

(v)

where $R^a$ is as defined under (i) and in addition may be benzyl or $C_1-C_6$ alkyl and $R^b$ and $R^c$ have the meanings defined under (iv). The preferred $R^a$ substituents in this category are benzyl, $C_1-C_6$ alkyl and those mentioned under (i) as being preferred aryl, substituted aryl, cycloalkyl (and substituted cycloalkyl) and cycloalkenyl (and substituted cycloalkenyl) groups. The most preferred aryl groups of this type are those in which $R^b$ and $R^c$ are hydrogen and $R^a$ is phenyl; phenyl substituted with one or more radicals selected from chloro, bromo, iodo, fluoro, nitro, amino, (lower)alkyl, (lower)alkylthio, cyano, (lower)alkoxy, (lower)alkylamino, hydroxy, acetoxy or trifluoromethyl; 3-pyridyl; or 4-pyridyl;

vi. $R^aX(CH_2)_mCO-$ where $R^a$ is as defined under (i) and in addition may be benzyl, X is oxygen or sulphur and $m$ is an integer from 2–5. The preferred $R^a$ groups are benzyl and those mentioned under (i) as being preferred aryl, substituted aryl, cycloalkyl (and substituted cycloalkyl) and cycloalkenyl (and substituted cycloalkenyl) groups. An example of this group is S-benzylthiopropionyl.

vii. $R^aCO-$ where $R^a$ is as defined under (i). The preferred $R^a$ groups are those mentioned under (i) as being preferred aryl, substituted aryl, cycloalkyl (and substituted cycloalkyl) and cycloalkenyl (and substituted cycloalkenyl) groups. The most preferred aryl groups of this category are those in which $R^a$ is phenyl; phenyl substituted with one or more radicals selected from chloro, bromo, iodo, fluoro, nitro, amino, (lower)-alkyl, (lower)alkylthio, cyano, (lower)alkoxy, (lower)-alkylamino, di(lower)alkylamino, hydroxy, acetoxy or trifluoromethyl, and most preferably phenyl substituted at the 2-position by carboxy or phenyl or at the 2- and 6-positions by methoxy; 2-ethoxynaphthoyl; 3-phenyl-5-methylisoxazol-4-yl; 3-o-chlorophenyl-5-methylisoxazol-4-yl; 3-(2,6-dichlorophenyl)-5-methylisoxazol-4-yl and 1-aminocyclohexyl. Examples of this group include 2,6-dimethoxybenzoyl, benzoyl, 2-biphenylcarbonyl, 2-aminomethylbenzoyl, 2-carboxybenzoyl-2-phenylbenzoyl, 2-thienylcarbonyl, 3-thienylcarbonyl and 2-chlorobenzoyl;

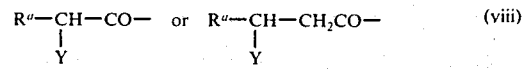
(viii)

where $R^a$ is as defined under (i) and Y is hydrazino, guanidino, ureido, thioureido and substituted thioureido (as disclosed in U.S. Pat. No. 3,741,962), allophanamido (as described in U.S. Pat. No. 3,483,188), 3-guanyl-1-ureido (as in U.S. Pat. No. 3,796,709), 3-(2-furoyl-)ureido, cyanamino (as in U.S. Pat. No. 3,796,709), 3-(benzoyl)ureido, azido, amino, acylamino (e.g. carbobenzoxyamino), a group obtained by reacting the amino group of the 7-side chain with an aldehyde or ketone (e.g. acetone, formaldehyde, acetaldehyde, butyraldehyde, acetylacetone, methyl acetoacetate, benzaldehyde, salicylaldehyde, methyl ethyl ketone or ethyl acetoacetate), hydroxy, etherified hydroxy, esterified hydroxy, carboxy, esterified carboxy (as disclosed for example in U.S. Pat. Nos. 3,282,926, 3,819,601 and 3,635,961 and including especially

), triazolyl, tetrazolyl, cyano, halogeno, acyloxy (e.g. formyloxy or (lower)alkanoyloxy), sulfo, sulfoamino or esterified sulfo. The preferred $R^a$ substituents are those mentioned under (i) as being preferred aryl, substituted aryl, cycloalkyl (and substituted cycloalkyl) and cycloalkenyl (and substituted cycloalkenyl) groups. Preferred Y substituents are hydrazino; guanidino; ureido; substituted thioureido of the formula

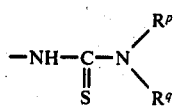

in which $R^p$ is hydrogen or $C_1$-$C_8$ alkyl and $R^q$ is hydrogen, $C_1$-$C_8$ alkyl, $C_2$-$C_8$ alkenyl, phenyl, benzoyl, $C_1$-$C_8$ alkoxy-$C_1$-$C_8$ alkyl, (carbo-$C_1$-$C_8$ alkoxy) $C_1$-$C_8$ alkyl; allophanamido; 3-guanyl-1-ureido; 3-(2-furoyl)ureido; 3-(benzoyl)ureido; azido; amino; a group obtained by reacting the amino group Y with acetone, formaldehyde, acetaldehyde, butyraldehyde, acetylacetone, methyl acetoacetate, benzaldehyde, salicylaldehyde, methyl ethyl ketone or ethyl acetoacetate; hydroxy; etherified hydroxyl including especially (lower)alkoxy; carboxy; esterified carboxy including especially 5-indanyloxycarbonyl; triazolyl; tetrazolyl; cyano; cyanamino; halogeno; formyloxy; (lower)alkanoyloxy; sulfo; or sulfoamino. Examples of this group include α-aminophenylacetyl; α-carboxyphenylacetyl; 2,2-dimethyl-5-oxo-4-phenyl-1-imidazolyl; α-amino-p-hydroxyphenylacetyl; α-hydroxyphenylacetyl; α-formyloxyphenylacetyl and other aryl groups of this type disclosed in U.S. Pat. No. 3,812,116 and 3,821,017; α-amino-α-2- or 3-thienylacetyl; α-amino-α-(3-chloro-4-hydroxy)phenylacetyl; α-amino-α-(1,4-cyclohexadienyl)acetyl; α-azidophenylacetyl; α-amino-α-(1-cyclohexenyl)acetyl; 2-carboxy-α-3-thienylacetyl; α-amino-α-(3,5-dichloro-4-hydroxyphenyl)acetyl; α-amino-α-3- or 4- or 5-isothiazolylacetyl (as in U.S. Pat. No. 3,579,506) and other α-amino and α-hydroxy-heterocyclylacetyl groups as disclosed for example in U.S. Pat. No. 3,821,207;

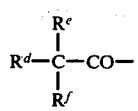 (ix)

where $R^d$, $R^e$ and $R^f$ which may be the same or different may each represent $C_1$-$C_6$ alkyl, phenyl or substituted phenyl. The preferred phenyl substituents are one or more radicals selected from chloro, bromo, iodo, fluoro, trifluoromethyl, nitro, amino, cyano, (lower)alkanoyloxy, (lower)alkanoyl, (lower)alkoxyamino, (lower)alkoxy, (lower)alkyl, (lower)alkylamino, hydroxy, (lower)alkylthio, carboxy, di(lower)alkylamino or sulfamyl. An example of this group is triphenylmethylcarbonyl.

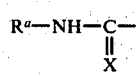 (x)

where $R^a$ is as defined under (i) and in addition may be hydrogen, $C_1$-$C_6$ alkyl, halogen substituted $C_1$-$C_6$ alkyl, phenethyl, phenoxymethyl; benzyl or

and X is oxygen or sulphur. An example of such a group is $Cl(CH_2)_2NHCO$;

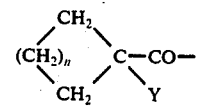 (xi)

where Y is as defined under (viii) and n is an integer of 1-4. A most preferred Y substituent is amino. An example of this group is 1-aminocyclohexanecarbonyl.

xii. Aminoacyl, for example

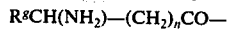

where n is an integer of 1-10, or

where m is zero or an integer from 1-10, and n is 0, 1, or 2; $R^g$ is hydrogen or an alkyl, aryl, aralkyl or carboxy group or a group as defined under $R^a$ in (i) above; and Ar is an arylene group, e.g. p-phenylene or 1,4-naphthylene. Preferred aryl groups of the above formulae are those in which $R^g$ is hydrogen, (lower)-alkyl, phenyl, benzyl or carboxy and Ar is p-phenylene or 1,4-naphthylene. Examples of such groups are disclosed in U.K. Pat. No. 1,054,806. Examples of groups of this type include p-aminophenylacetyl and δ-aminoadipoyl derived from naturally occurring amino acids and derivatives thereof, e.g. N-benzoyl-δ-aminoadipoyl;

xiii. Substituted glyoxylyl groups of the formula

where $R^h$ is an aliphatic, araliphatic or aromatic group. The preferred $R^h$ groups are 2-thienyl; 3-thienyl; α-naphthyl; 2-phenanthryl or a mono-, di- or trisubstituted phenyl group, the substituents being selected from chloro, bromo, iodo, fluoro, amino, di(lower)alkylamino, (lower)alkyl, (lower)alkoxy, nitro or (lower)alkanoylamino. Examples of this category are disclosed in U.S. Pat. No. 3,546,219 and 3,573,294. Included in this group are also the α-carbonyl derivatives of the above substituted glyoxylyl groups formed for example with hydroxylamine, semicarbazide, thiosemicarbazide, isoniazide or hydrazine;

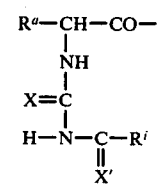 (xiv)

where $R^a$ has the meaning defined under (i), X is oxygen or sulphur, X' is oxygen or imino and $R^i$ represents (lower)alkyl, cycloalkyl having 4,5,6 or 7 carbon atoms, monohalo(lower)alkyl, dichloromethyl, trichloromethyl, (lower)alkenyl of 2-6 carbon atoms,

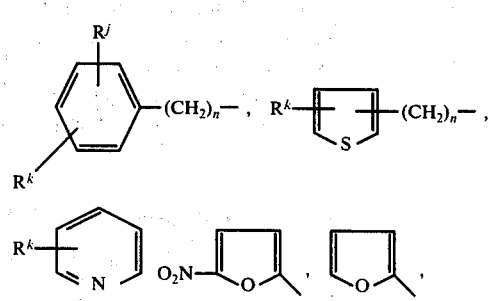

-continued

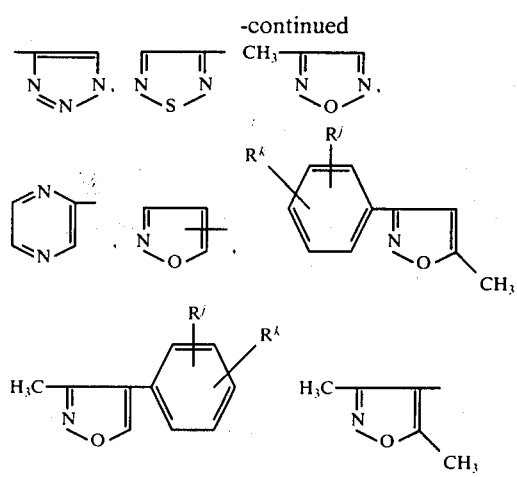

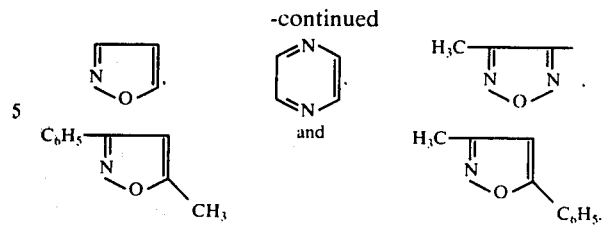

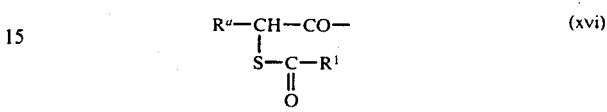

Examples of this group are disclosed in U.S. Pat. Nos. 3,626,024 and 3,692,779;

$$R^a-CH-CO- \atop S-C-R^1 \atop \| \atop O \qquad (xvi)$$

where $R^a$ has the meaning defined in (i) and $R^1$ is (lower)alkyl, $C_3$–$C_{12}$ cycloalkyl, aryl (especially phenyl), a monocyclic heterocyclic radical having 5 or 6 atoms exclusive of hydrogen which are C, S, N or O, no more than 2 atoms being other than C, or a substituted monocyclic heterocyclic radical as defined above having one or more substituents selected from halo, (lower)alkyl, (lower)alkoxy or phenyl. Examples of this group are disclosed in U.S. Pat. No. 3,778,436. Most preferred $R^1$ groups are (lower)alkyl, phenyl, thienyl or furyl.

*n* is an integer from 0 to 3 inclusive and each of $R^k$ and $R^j$ is hydrogen, nitro, di(lower)alkylamino, (lower)alkanoylamino, (lower)alkanoyloxy, $C_1$–$C_6$ alkyl, $C_1$–$C_6$ alkoxy, sulfamyl, chloro, bromo, iodo, fluoro or trifluoromethyl. The preferred $R^a$ substituents are those mentioned under (i) as being preferred aryl, substituted aryl, cycloalkyl (and substituted cycloalkyl) and cycloalkenyl (and substituted cycloalkenyl) groups. Preferred acyl groups of this type are those in which $R^a$ is 2-thienyl; 3-thienyl; phenyl; or phenyl substituted by one or more radicals selected from nitro, di(lower)alkylamino, (lower)alkanoylamino, amino, hydroxy, (lower)alkanoyloxy, $C_1$–$C_6$ alkyl, $C_1$–$C_6$ alkoxy, sulfamyl, chloro, bromo, iodo, fluoro or trifluoromethyl; X is oxygen; X' is oxygen or imino and $R^i$ is (lower)alkyl, phenyl, 2-thienyl, 3-thienyl, 2-furyl or 5-nitro-2-furyl. The most preferred groups are those of the above formula where $R^a$ is phenyl, p-hydroxyphenyl, 2-thienyl or 3-thienyl; X is oxygen; X' is oxygen, and $R^i$ is phenyl or 2-furyl. Examples are disclosed in U.S. Pat. Nos. 3,687,949 and 3,646,024;

A preferred class of acyl groups are those of the formula $$Ar'-CH-C- \atop | \atop Y \qquad \overset{O}{\|}$$

wherein Ar' is a radical of the formula

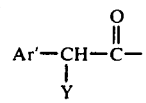

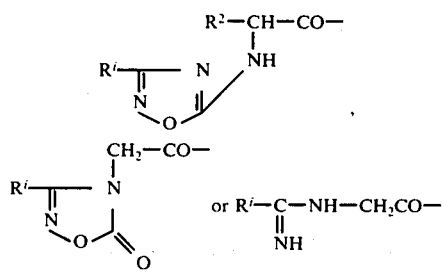

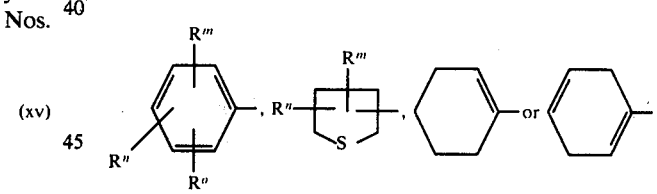

where $R^a$ has the meaning defined in (i) and $R^i$ has the meaning defined in (xiv). The preferred $R^a$ substituents are those mentioned under (i) as being preferred aryl, substituted aryl, cycloalkyl (and substituted cycloalkyl) and cycloalkenyl (and substituted cycloalkenyl) groups. Preferred $R^i$ substituents include (lower)alkyl, dichloromethyl, $C_4$–$C_7$ cycloalkyl, 2-thienyl, 3-thienyl, phenyl, benzyl, halobenzyl,

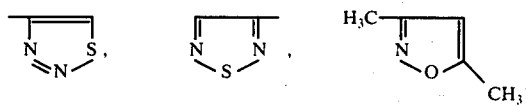

in which $R^m$, $R^n$ and $R^o$ are alike or different and each is hydrogen, hydroxy, (lower)alkyl, cyano, (lower)alkoxy, chloro, bromo, iodo, fluoro, trifluoromethyl, nitro, amino, (lower)alkylamino, di(lower)alkylamino, (lower)alkanoyl, (lower)alkanoyloxy such as p-acetoxy or phenyl and Y is amino or a group obtained by reacting the amino group with acetaldehyde, formaldehyde or acetone, fluoro, chloro, bromo, iodo, hydroxy, (lower)alkanoyloxy, carboxy, guanidino, 3-guanyl-1-ureido, 3-(2-furoyl)ureido, 3-benzoylureido, sulfo, sulfoamino, ureido, thioureido, (lower)alkoxy, cyano, cyanamino or indanyloxycarbonyl. Particularly preferred Ar radicals are phenyl, p-hydroxyphenyl, 4-hydroxy-3,5-dichlorophenyl, 3-chloro-4-hydroxyphenyl, o-, m- or p-aminomethylphenyl, 2-thienyl, 3-thienyl, 1-cyclohexenyl and 1,4-cyclohexadienyl. Particularly preferred Y groups are amino, hydroxy and carboxy. Set forth below are formulae of the most preferred acyl groups of this class:

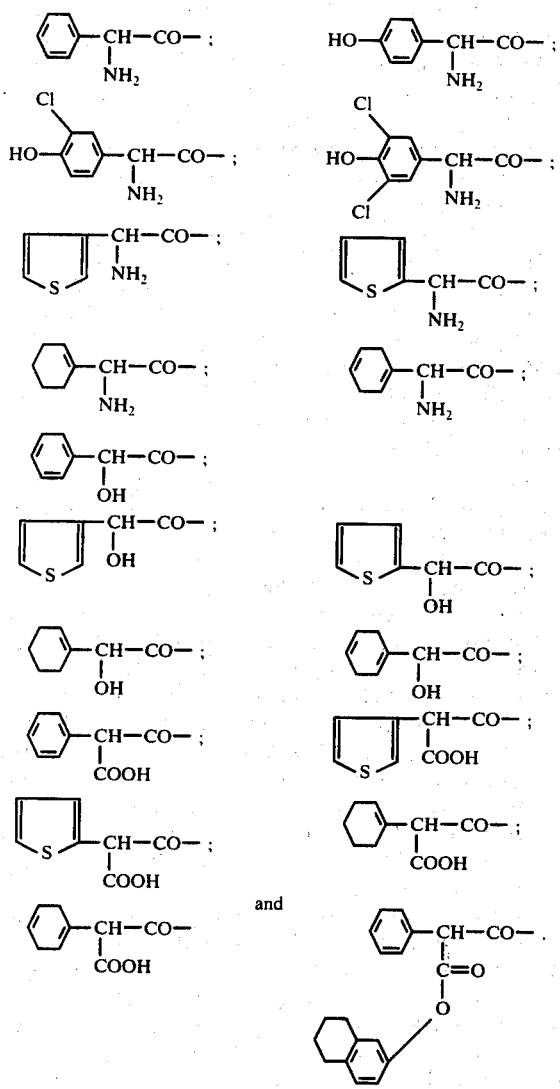
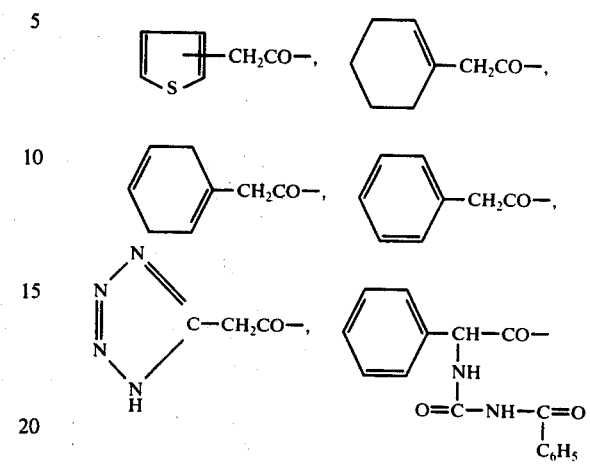
where U and V are alike or different and each is hydrogen, chloro or fluoro;
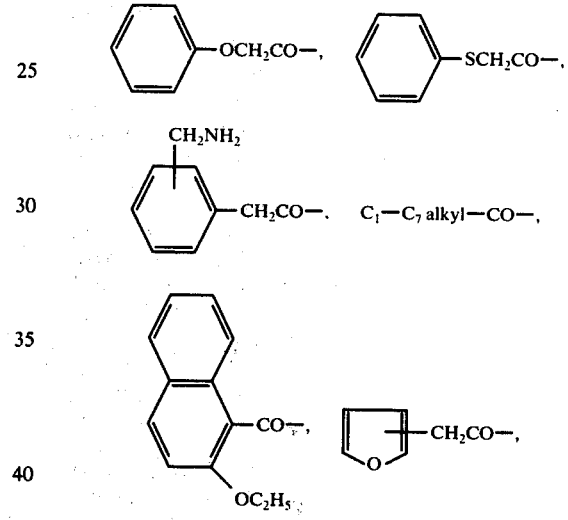
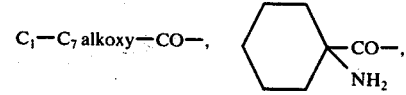
Of most interest are the acyl groups of the above class where the acid ArCH(X)COOH is of the D-series.
Other particularly preferred acyl groups for the compounds of formula I are
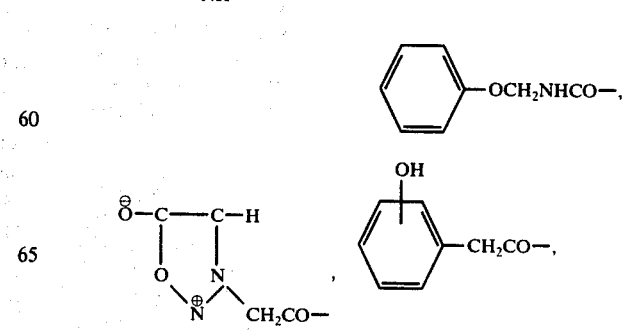

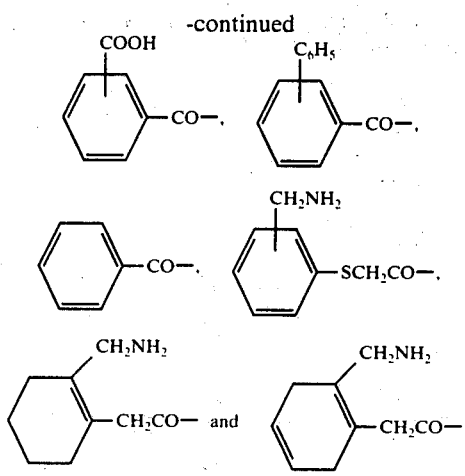

Substituent Z in formulae I and II above may be halo (chloro, bromo, fluoro or iodo), hydroxyl, hydroxyl esterified with a carboxylic acid or a sulfonic acid residue or etherified hydroxyl. Esterified hydroxyl groups include radicals of the formula

—OR$_1$ wherein R$_1$ is an acyl group, a (lower)alkylsulfonyl group, an arylsulfonyl group or an aralkylsulfonyl group and are preferably those of the formula —OCOR$_2$ or —OSO$_2$R$_2$' wherein R$_2$ is hydrogen, amino, (lower)alkyl (e.g. methyl, ethyl, propyl, isopropyl, butyl, isobutyl, t-butyl, amyl, hexyl), C$_3$–C$_7$ cycloalkyl (e.g. cyclobutyl, cyclopentyl, cyclohexyl, cyclopropyl or cycloheptyl), C$_3$–C$_7$ cycloalkyl-(lower)alkyl (e.g. cyclobutylmethyl, cyclobutylethyl, cyclopentylmethyl, cyclohexylmethyl, cyclopentylpropyl, etc.), aryl (e.g. phenyl or naphthyl), aralkyl (e.g. benzyl, tetrazolylacetyl, 2-(1-naphthyl)ethyl or phenethyl), or aryloxyalkylene, e.g., phenoxymethyl, and R$_2$' is (lower)alkyl, aryl or aralkyl. The R$_2$ and R$_2$' groups above may be optionally substituted as by one or more (lower)alkoxy, (lower)alkylthio, halogen, (lower)alkyl, nitro, hydroxy, acyloxy, carboxy, amino, (lower)alkylamino or acylamino radicals. The preferred R$_2$ groups are hydrogen, (lower)alkyl (especially methyl) and amino. The most preferred R$_2$' groups are (lower)alkyl (especially methyl), trifluoromethyl an p-tolyl.

Etherified hydroxyl groups include radicals of the formula

—OR$_3$ where R$_3$ is (lower)alkyl, (lower)cycloalkyl, (lower)cycloalkyl-(lower)alkyl, aryl, aralkyl or a heterocyclic group, any of said R$_3$ groups bring optionally substituted by one or more (lower)alkoxy, (lower)alkoxy(lower)alkyl, (lower)alkylthio, halogen, (lower)alkyl, (lower)cycloalkyl, (lower)alkenyl, nitro, hydroxy, acyloxy, carboxy, amino, di(lower)alkylamino, (lower)alkylamino, trifluoromethyl, aryl, aralkyl or acylamino radicals.

Preferred R$_3$ groups include benzyl and 5- or 6-membered heterocyclic radicals containing 1–4 atoms selected from N, O and S, said heterocyclic radicals being optionally substituted by one or more substituents selected from halogen, amino, nitro, C$_1$–C$_4$ alkyl, C$_3$–C$_4$ cycloalkyl, C$_1$–C$_4$ alkoxy, C$_2$–C$_4$ alkenyl, trifluoromethyl phenyl, benzyl, C$_1$–C$_4$ alkylthio, C$_1$–C$_4$ alkyl-amino, di C$_1$–C$_4$ alkylamino or alkoxyalkyl of up to 4 carbon atoms. Examples of preferred heterocyclic R$_3$ groups include furyl, thienyl, pyrazolyl, imidazolyl, isoimidazolyl, triazolyl, tetrazolyl, thiazolyl, thiadiazolyl, thiatriazolyl, oxazolyl, oxadiazolyl, isothiazolyl, isoxazolyl, pyridyl, pyridazinyl, pyrimidinyl and triazinyl, said radicals being optionally substituted by one or two of the above-mentioned substituents, most preferably C$_1$–C$_4$ alkyl, C$_1$–C$_4$ alkoxy or trifluoromethyl groups. Particularly preferred heterocyclic R$_3$ groups include 1,2,3-triazolyl, 1,2,4-triazolyl, 1,2,4-thiadiazolyl, 1,3,4-thiadiazolyl, 1,3,4-oxadiazolyl, 1,2,3,4-tetrazolyl, 2-methyl-1,3,4-thiadiazol-5-yl, 2-methyl-1,3,4-oxadiazol-5-yl and 1-N-methyltetrazolyl.

Preferred Z substituents in formula I and II are those of the formulae -halo, i.e. chloro, bromo, iodo, fluoro; —OH; —OCHO; —OCOCH$_3$; —OSO$_2$CH$_3$; —OSO$_2$CF$_3$; —OSO$_2$C$_6$H$_4$CH$_3$ (para); —OCH$_2$C$_6$H$_5$; and —OCONH$_2$.

When Z is hydroxyl, compounds of formulae I and II may also exist as the lactones which are formed by internal esterification with the carboxyl groups.

The term "(lower)alkyl" as used herein means both straight and branched chain aliphatic hydrocarbon radicals having from one to ten carbon atoms such as methyl, ethyl, propyl, isopropyl, butyl, isobutyl, t-butyl, amyl, hexyl, 2-ethylhexyl, heptyl, decyl, etc. Similarly, where the term "(lower)" is used as part of the description of another group, e.g. "(lower)alkoxy", it refers to the alkyl portion of such group which is therefore described above in connection with "(lower)alkyl".

The pharmaceutically acceptable salts referred to above include the nontoxic carboxylic acid salts, e.g. nontoxic metallic salts such as sodium, potassium, calcium and aluminum, the ammonium salt and salts with nontoxic amines, e.g. trialkylamines, procaine, dibenzylamine, N-benzyl-β-phenethylamine, 1-ephenamine, N,N'-dibenzylethylenediamine, N-alkylpiperidine and other amines which have been used to form salts of penicillins and cephalosporins. When a basic group is present, as when it occurs in the 7-acyl group, the present invention also includes the pharmaceutically acceptable acid addition salts, e.g. salts with mineral acids such as hydrochloric, hydrobromic, hydroiodic, phosphoric, sulfuric and salts with organic acids such as maleic, acetic, citric, oxalic, succinic, benzoic, tartaric, fumaric, mandelic, ascorbic and malic. The term "pharmaceutically acceptable salts" is also meant to include nontoxic acid addition salts of the easily cleavable esters referred to above. The compounds which contain a basic group in radical R may also be present in the form of an internal salt, i.e. in the form of the zwitterion.

The easily cleavable esters referred to above include ester groups which are removable by methods, e.g. chemical or enzymatic hydrolysis, treatment with chemical reducing agents under mild conditions, irradiation with ultraviolet light or catalytic hydrogenation, which do not result in any appreciable destruction of the remaining portion of the molecule. Examples of suitable esters include those disclosed in U.S. Pat. Nos. 3,284,451 and 3,249,622 and U.K. Pat. Nos. 1,229,453 and 1,073,530. Esters which have been used previously in penicillin and cephalosporin chemistry include for example benzhydryl, p-nitrobenzyl, benzyl, trichloroethyl, silyl such as trimethylsilyl, phenacyl, p-methoxybenzyl, acetonyl, phthalidyl, indanyl and (lower)alkyl such as methyl, ethyl and t-butyl. Particularly preferred easily cleavable esters are those which are hydrolyzed under physiological conditions such as pivaloyloxymethyl, acetoxymethyl, phthalidyl, indanyl and methoxymethyl.

As the 0-2-isocephem compounds of the present invention may possess one or more asymmetric carbon atoms, the invention includes all of the possible enantiomeric and diastereomeric forms of the compounds of the general formula II shown above. Resulting mixtures of isomers can be separated into the individual isomers according to methods which are known per se, e.g. fractional crystallization, adsorption chromatography or other suitable separation processes. Resulting racemates can be separated into the antipodes in the usual manner after introduction of suitable salt-forming groupings, e.g. by forming a mixture of diastereoisomeric salts with optically active salt-forming agents, separating the mixture into diastereoisomeric salts, and converting the separated salts into the free compounds, or by fractional crystallization from optically active solvents.

It will be appreciated that certain of the compounds of this invention exist in various states of solvation and the anhydrous as well as solvated forms are within the scope of the invention.

The free acid compounds of the above general formula II where R is acyl and physiologically hydrolyzed esters thereof together with the pharmaceutically acceptable salts of such free acids and esters are useful as antibacterial agents. Certain of the 7-acylated compounds of formula II, e.g. those in which Z is halo, hydroxyl, —OCHO, —OCH$_2$C$_6$H$_5$ or sulfonyloxy (especially —OSO$_2$CH$_3$, —OSO$_2$CF$_3$ or —OC$_6$H$_4$CH$_3$) are useful not only as active antibacterial agents per se but as intermediates in preparation of other active 7-acylated derivatives within the scope of formula II. The remaining compounds of the above general formula II including salts and esters thereof are valuable intermediates which can be converted into the above-mentioned pharmacologically active compounds in a simple manner for example, as described below.

Preferred embodiments of the present invention are the compounds of the formula

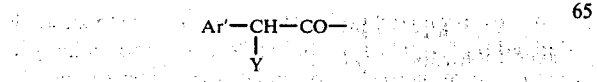

wherein R is an acyl group and R$_4$ is halo, hydroxyl, —OCHO, —OCONH$_2$, —OCOCH$_3$, —OCH$_2$C$_6$H$_5$ or —OSO$_2$CH$_3$, and easily cleavable esters and pharmaceutically acceptable salts thereof.

Preferred compounds of formula IIa are those in which R is an acyl group selected from the acyl groups defined above under (i) to (xvi). Use of the acyl groups mentioned above as being preferred within categories (i) to (xvi) results in active end-products having the most advantageous pharmacological properties.

More preferred acids, esters and salts of formula IIa are those in which acyl group R is

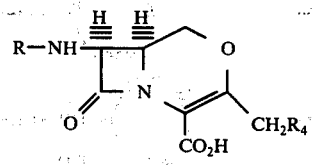

in which Ar' is a radical of the formula

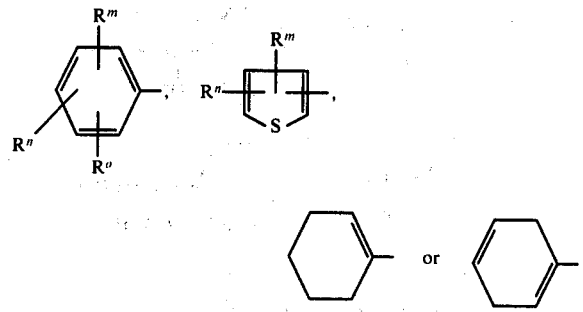

in which R$^m$, R$^n$ and R$^o$ are alike or different and each is hydrogen, hydroxy, (lower)alkyl, cyano, (lower)alkoxy, chloro, bromo, iodo, fluoro, trifluoromethyl, nitro, amino, (lower)alkylamino, di(lower)alkylamino, (lower)-alkanoyl, (lower)alkanoyloxy such as p-acetoxy or phenyl and Y is amino or a group obtained by reacting the amino group with acetaldehyde, formaldehyde or acetone; fluoro; chloro; bromo; iodo; hydroxy; (lower)alkanoyloxy; carboxy; guanidino; 3-guanyl-1-ureido; 3-(2-furoyl)ureido; 3-benzoylureido; sulfo; sulfoamino; ureido; thioureido; (lower)alkoxy; cyano; cyanamino; or indanyloxycarbonyl.

Other preferred acids, esters and salts of formula IIa are those in which R is

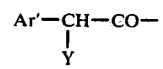

wherein Ar' is phenyl, p-hydroxyphenyl, 4-hydroxy-3-,5-dichlorophenyl, o-, m- or p-aminomethylphenyl, 2-thienyl, 3-thienyl, 1-cyclohexenyl or 1,4-cyclo-hexadienyl and Y is amino, carboxy or hydroxy.

Other preferred compounds of formula IIa are those wherein R is an acyl group of the formula

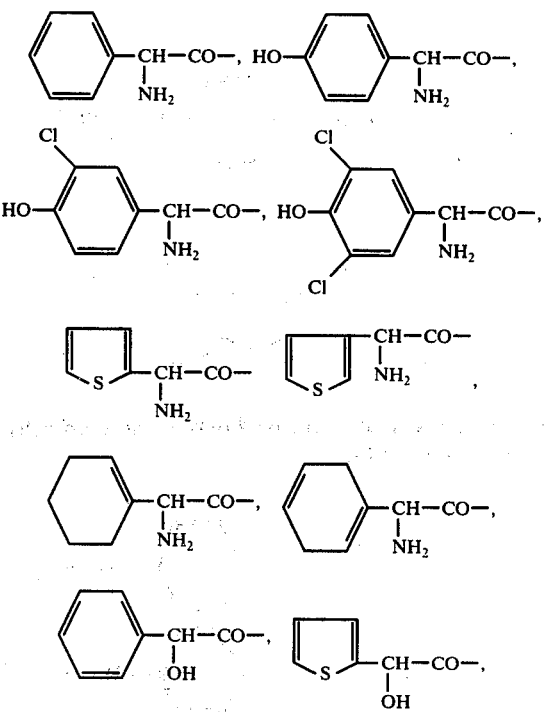

-continued

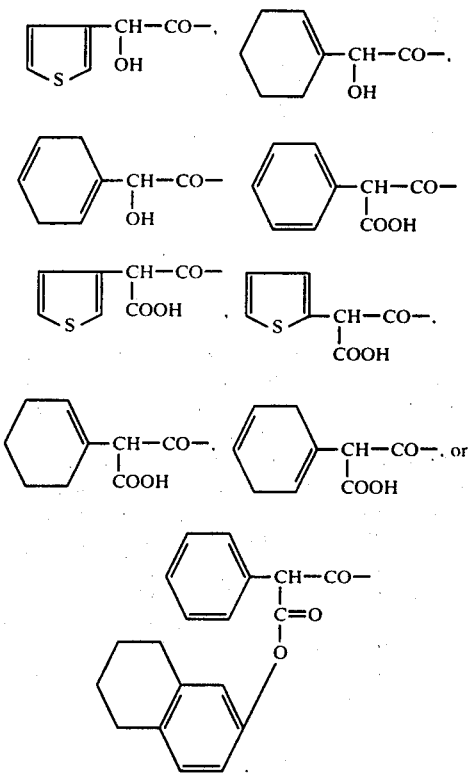

Other preferred compounds of formula IIa are those wherein R is an acyl group of the formula

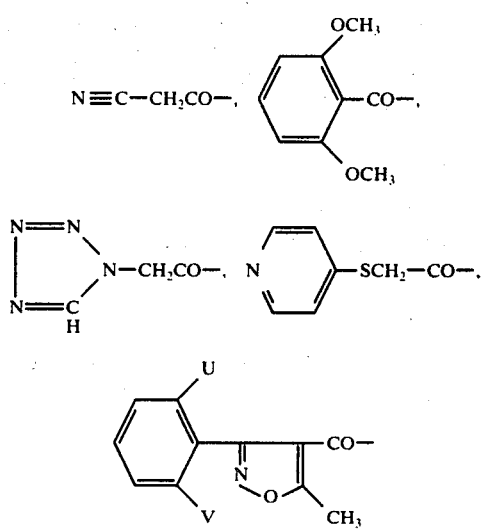

wherein U and V are alike or different and each is hydrogen, chloro or fluoro;

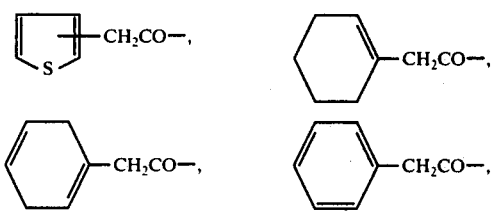

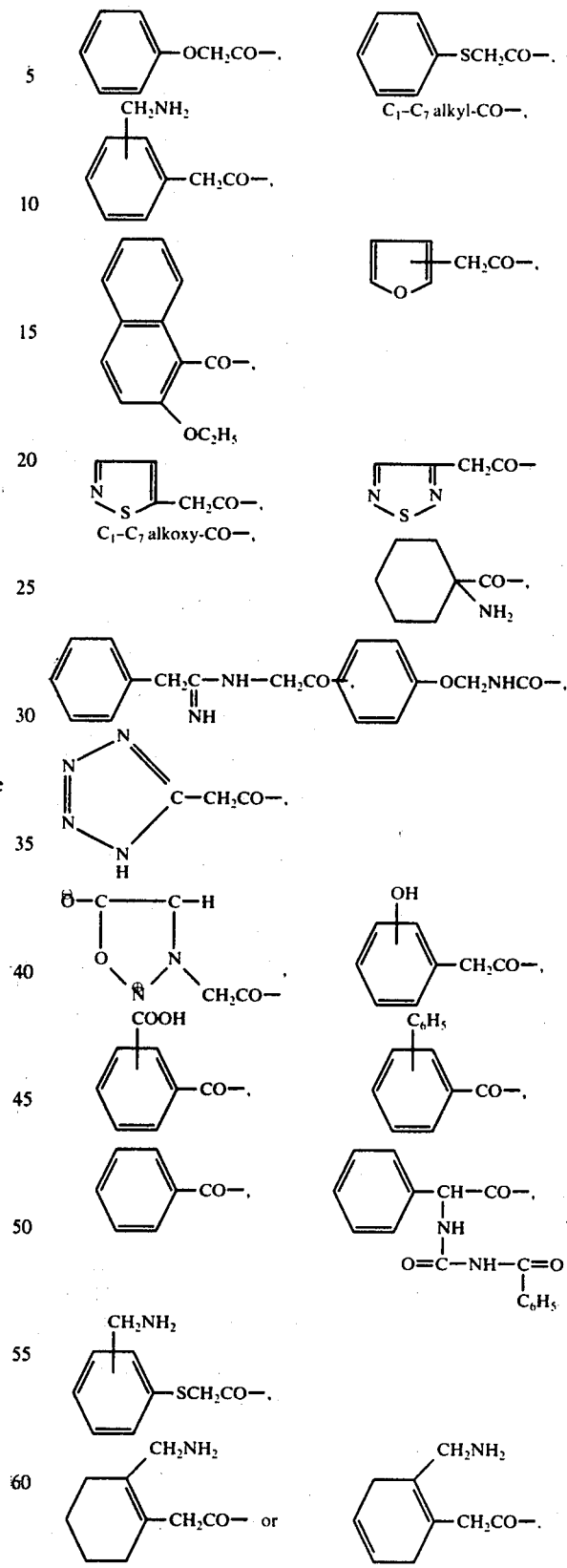

A most preferred group of compounds are those acids defined by formula IIa wherein R is α-carboxyphenylacetyl, cyanoacetyl, α-amino-α-(p-hydroxyphenyl)-acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)acetyl, α-amino-α-(1,4-cyclohexadienyl)acetyl, α-hydroxyacetyl, α-hydroxy-α-(2-thienyl)acetyl, α-hydroxy-α-(3-thienyl)acetyl α-hydroxy-α-(1-cyclohexenyl)acetyl, α-hydroxy-α-(1,4-cyclohexadienyl)acetyl, α-carboxy-α-(2-thienyl)acetyl, α-carboxy-α-(3-thienyl)acetyl, α-carboxy-α-(1-cyclohexenyl)acetyl, α-carboxy-α-(1,4-cyclohexadienyl)-acetyl, α-indanyloxycarbonyl-α-phenylacetyl, 1-(1H)-tetrazolyl, 4-pyridylthioacetyl, 2-thienylacetyl, 3-thienylacetyl, 1-cyclohexenylacetyl, 1,4-cyclohexadienylacetyl, o-aminomethylphenylacetyl, 1-aminocyclohexylcarbonyl, 2,6-dimethoxybenzoyl, sydnoneacetyl or α-azidophenylacetyl, or a pharmaceutically acceptable salt thereof.

Another most preferred group of compounds are the D-isomers of those acids defined by formula IIa wherein R is α-amino-α-(p-hydroxyphenyl)acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)acetyl, α-amino-α-(1,4-cyclohexadienyl)acetyl, α-hydroxyacetyl, α-hydroxy-α-(2-thienyl)acetyl, α-hydroxy-α-(3-thienyl)acetyl, α-hydroxy-α-(1-cyclohexenyl)acetyl or α-hydroxy-α-(1,4-cyclohexadienyl)acetyl, or a pharmaceutically acceptable salt thereof.

Preferred compounds of formula IIa are the acids in which R is phenoxyacetyl, or the pharmaceutically acceptable salts thereof.

Other preferred compounds of formula IIa are the acids in which R is phenylacetyl, or pharmaceutically acceptable salts thereof.

Other preferred compounds of formula IIa are the acids in which R is 2-thienylacetyl or 3-thienylacetyl, or pharmaceutically acceptable salts thereof.

Still further preferred compounds of formula IIa the acids in which R is α-hydroxyphenylacetyl or α-aminophenylacetyl, or pharmaceutically acceptable salts thereof. The pivaloyloxymethyl, phthalidyl, indanyl, acetoxymethyl and methoxymethyl esters of these acids as well as pharmaceutically acceptable salts thereof are also preferred compounds of the present invention. The isomers of those compounds in which the α-carbon atom of the 7-acyl group is of the D-series are found to be of particular importance.

The present invention further provides various novel intermediates useful in the synthesis of the 7-acylamido 0-2-isocephem compounds of formula II described above.

Preferred embodiments of the present invention are the novel intermedites having the formula

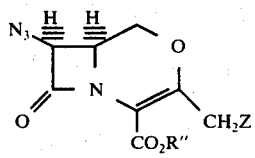

IV wherein Z is halo, hydroxyl, hydroxyl esterified with a carboxylic acid or a sulfonic acid residue or etherified hydroxyl and R" is hydrogen or an easily cleavable ester carboxyl-protecting group, and salts thereof. The preferred Z substituents are as defined above in connection with the compounds of formula II.

The most preferred intermediates of formula IV are those of the formula

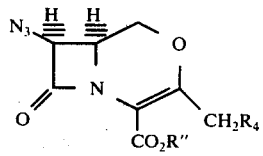

IVa wherein $R_4$ is halo, hydroxyl, —OCHO, —OCH$_2$C$_6$H$_5$, —OCONH$_2$, —OCOCH$_3$ or —OSO$_2$CH$_3$.

Intermediates of formula IVa in which $R_4$ is —OSO$_2$CH$_3$ or —OCHO are of particular importance as starting materials in preparing other intermediates within the scope of formula IV.

Other preferred intermediates are the compounds having the formula

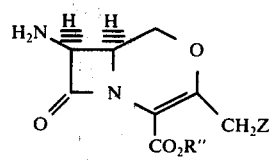

III wherein Z is halo, hydroxyl, hydroxyl esterified with a carboxylic acid or a sulfonic acid residue or etherified hydroxyl and R" is hydrogen or an easily cleavable ester carboxyl-protecting group, and salts thereof. The preferred Z substituents are those mentioned above as being preferred in connection with the compounds of formula II.

The most preferred intermediates or formula III are those of the formula

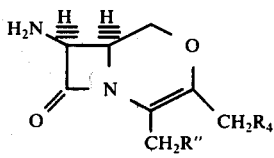

IIIa wherein $R_4$ is halo, hydroxyl, —OCHO, —OCH$_2$C$_6$H$_5$, —OCOCH$_3$, —OCONH$_2$ or —OSO$_2$CH$_3$ and R is hydrogen or an easily cleavable ester carboxyl-protecting group.

Preferred intermediates of formula IIIa are those in which $R_4$ is —OCHO or —OSO$_2$C$_3$.

The intermedites of formulae III and IV may be in the form of the free carboxylic acid or a salt thereof or in the form where the carboxyl group is protected in a conventional manner such as preferably by esterification. The protecting group is selected so that it may be removed by methods which do not result in any appreciable destruction of the remaining portion of the molecule. Preferred carboxyl protecting groups are the easily cleavable esters as defined above including in particular benzhydryl, -nitrobenzyl, trichloroethyl, silyl including especially trimethylsilyl, phenacyl, p-methoxybenzyl, acetonyl, (lower)- alkyl such as methyl, t-butyl or ethyl, benzyl, tri-phenylmethyl, methoxymethyl, acetoxymethyl, phthalidyl, indanyl and pivaloyloxymethyl.

The novel 7-acylamido compounds of formula II may be prepared by N-acylating a 7-amino intermediate of the formula

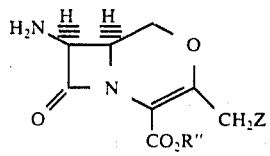

wherein Z is hydroxyl, hydroxyl esterified with a carboxylic acid or a sulfonic acid residue or etherified hydroxyl and R" is hydrogen or an eaily cleavable ester carboxyl-protecting group, or a salt thereof, with an acylating acid of the formula

R—COOH wherein R is an acyl group, or with its functional equivalent as an acylating agent for a primary amine and, if desired, converting the so-produced product to the corresponding 7-acylated product having a substituent Z different from that in starting material III and, if desired, (a) when R" is a carboxyl-protecting group, converting the 7-acylated ester to the free acid compound or a physiologically hydrolyzed ester or a pharmaceutically acceptable salt of said acid or ester, or (b) when R" is hydrogen, converting the 7-acylated carboxylic acid to a physiologically hydrolyzed ester or a pharmaceutically acceptable salt of said acid or ester and, if desired, resolving a resulting isomer mixture into its component isomers.

The 7-amino starting materials of general formula III are of use primarily as intermediates in preparing the pharmacologically active N-acyl derivatives of formula II. The free acids, physiologically hydrolyzed esters and pharmaceutically acceptable salts of said acids and esters of formula III, however, do possess some antibacterial activity per se against various pathogenic microorganisms.

The 7-acylamido -b 0-2-isocephem compounds of formula II are prepared by N-acylation according to known methods of the 7-amino group of intermediate III with an acylating acid of the formula

R—COOH wherein R is an acyl group, or with its functional equivalent as an acylating agent for a primary amino group. The acylating agents for preparing the products of formula II are known, readily preparable by known methods or described herein.

Intermediate III may be acylated either in the form of the free carboxylic acid (or salt thereof) or as an easily cleavable ester (or acid addition salt thereof). Preferred esters include benzhydryl, benzyl, p-nitrobenzyl, trichloroethyl, silyl (especially trimethylsilyl), phenacyl, p-methoxybenzyl, acetonyl, (lower)alkyl including particularly methyl, ethyl and t-butyl, triphenylmethyl, methoxymethyl, acetoxymethyl, pivaloyloxymethyl, phthalidyl and indanyl. The procedures for preparing esters of carboxylic acids are disclosed in the literature and are well-known to those skilled in the art of penicillin and cephalosporin chemistry. Methods for preparing certain of the more preferred easily cleavable esters, i.e. the pivaloyloxymethyl, acetoxymethyl, methoxymethyl, acetonyl and phenacyl esters, are disclosed in U.S. Pat. No. 3,284,451 and in U.K. Pat. No. 1,229,453. Preparation of phthalidyl esters of penicillins and cephalosporins is described in South African Patent Applications 72/3799 and 72/3800. The free acid form of intermediate III may also be converted to a silyl ester, e.g. trimethylsilyl ester, as by the methods described in the literature, e.g. U.S. Pat. No. 3,249,622. The silyl ester carboxylprotecting group may be easily removed following the acylation reaction by hydrolysis or alcoholysis.

Prior to the acylation reaction, any reactive substituents on the acylating acid or derivative thereof, e.g. hydroxy, carboxyl or mercapto, may be protected by use of suitable protecting or blocking groups which ar well-known to those skilled in the art of β-lactam chemistry, e.g. as by acylation or silylation. When the acylating agent contains an amino functional group in the acyl moiety, the amino group is protected by a conventional amino-blocking group which may be readily removed at the conclusion of the reaction. Examples of suitable amino-protecting or blocking groups include t-butyoxycarbonyl, carbobenzyloxy, 2-hydroxy-1-naphthcarbonyl, trichloroethoxycarbonyl, 2-ethoxycarbonyl1-methylvinyl and 2-methoxycarbonyl-1-methylvinyl. A particularly valuable amino-blocking group is a proton, as in the acylating agent of the formula

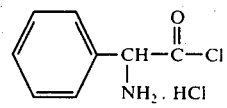

Preferred amino-protecting groups are t-butoxycarbonyl, carbobenzyloxy, the proton and a β-diketone or β-ketoester as in U.K. Pat. No. 1,123,333 or U.S. Pat. Nos. 3,325,479 and 3,316,247, e.g. methyl acetoacetate, or a β-ketoamide as in Japan 71/24714. When the t-butoxycarbonyl, carbobenzyloxy, β-ketoester, β-diketone or β-ketoamide protecting groups are employed, it is preferred to convert the acylating acid containing the blocked amino group to a mixed anhydride, e.g. with ethyl or isobutyl chloroformate, before reaction with compound III or a salt thereof. After the acylation coupling reaction, the amino-protecting group and any other functional protecting groups used may be removed by methods known per se to form the desired product of formula II. With respect to amino-protecting groups, the t-butoxycarbonyl group may be removed by use of formic acid, the carbobenzyloxy group by catalytic hydrogenation, the 2-hydroxy-1-naphthcarbonyl group by acid hydrolysis, the trichloroethoxycarbonyl group by treatment with zinc dust in glacial acetic acid, the proton by neutralization, etc.

Acylation of a free amino group of a cephalosporin or penicillin nucleus is a well-known reaction, and any of the functional equivalents of the carboxylic acid RCOOH commonly used in penicillin or cephalosporin chemistry as acylating agents for primary amino groups may be employed in acylating intermediate III. Examples of suitable acylating derivatives of the free acid include the corresponding acid anhydrides, mixed anhydrides (e.g. alkoxyformic anhydrides), acid halides, acid azides, active esters and active thioesters. The free acid may be coupled with compound III after first reacting said free acid with N,N'-dimethylchloroformininium chloride [cf. Great Britain Ser. No. 1,008,170 and Novak and Weichet, Experientia XXI, 6, 360(1965)] or by the use of enzymes or of an N,N'-carbonyldiimidazole or an N,N'-carbonylditriazole [cf. South African Specification No. 63/2684] or a carbodiimide reagent [especially N,N'-dicyclohexycarbodiimide, N,N'-diisopropylcarbodiimide or N-cyclohexyl-N'-(2- morpholinoethyl)carbodiimide: cf. Sheehan and Hess, *J.A.C.S.*, 77, 1967 (1955)], or of alkylylamine reagent [cf. R. Buijle and H. G. Viehe, *Angew. Chem. International Edition*, 3, 582, (1964)] or of an isoxasolium salt reagent [cf. R. B. Woodward, R. A. Olofson and H. Mayer, *J. Amer. Chem. Soc.*, 83, 1010 (1961)], or of a ketenimine reagent [cf. C. L. Stevens and M. E. Munk, *J. Amer. Chem. Soc.*, 80, 4065 (1958)] or of hexachlorocyclotriphosphatriazine or hexabromocyclotriphosphatriazine (U.S. 3,651,050) or of diphenylphosphoryl acide [DPPA; *J. Amer. Chem. Soc.*, 94, 6203-6205 (1972)] or of diethylphosphoryl cyanide [DEPC; *Tetrahedron Letters* No. 18, pp. 1595-1598)] or of diphenyl phosphite [*Tetrahedron Letters* No. 49, pp. 5047--5050 (1972)]. Other examples of suitable amide coupling reagents which have been described in the literature include $(CH_3)_2SCH_2CCHBr/DMSO$ (*J. Chem. Soc.* (C) 1904 (1969), $HCCOCH_3$(*Rec. Trav. Chim.* 74, 769 (1955), $(CH_3)_2C(OCH_3)_2$ (*Chim. Ther.* 2, 195 (1967), $SiCl_4$ (*J. Org. Chem.* 34, 2766 (1969), $TiCl_4$ (*Can. J. Chem.* 48, 983 (1970), $(PNCL_2)_3$(*J. Org. Chem.* 33, 2979 (1968), $SO_3.DMF$ (*J. Org. Chem.* 24, 368 (1959), ion exchange resins (*Helv.* 44, 1546 (1961) and *J.C.S. C*, 874 (1969) and

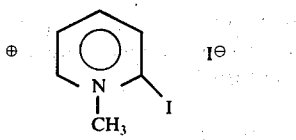

(*J. Chem. Soc.* 4650 (1964). An equivalent of the acid chloride is the corresponding azolide, i.e., an amide of the corresponding acid whose amide nitrogen is a member of a quasi-aromatic five membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield dimidazolide. The by-product, imidazole, precipitates and may be separated and the imidazolide isolated, but this is not essential. A preferred acylating agent for preparing 7-acylamido compounds containing an α-amino substituent, e.g. α-aminobenzyl, α-amino-α-thienylmethyl, etc. is the N-carboxy anhydride (Leuch's anhydride). In this structure the group which activates the carboxyl group also serves to protect the amino group. Another preferred acylating agent for introducing a side chain containing an α-amino functional group is the acid chloride hydrochloride, of the formula

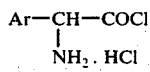

which also serves a dual function of carboxyl activation and amino protection. Mention was made above of the use of enzymes to couple the free acid with compound III. Included in the scope of such processes are the use of an ester, e.g. the methyl ester, of that free acid with enzymes provided by various microorganisms, e.g. those described by T. Takahaski et al., *J.a.C.S.*, 94(11), 4035-4037 (1972) and by T. Nara et al., *J. Antibiotics* (Japan) 24(5), 321-323 (1971) and in U.S. Pat. No. 3,682,777. A particularly preferred coupling agent for coupling the acylating acid with compound III (or a salt or ester thereof) is N-ethoxycarbonyl-2-ethoxy-1,2-dihydroquinoline (EEDQ) as described in *J.A.C.S.*, 90, 823-824 and 1652-1653 (1968) and U.S. Pat. No. 3,455,929.

The particular process conditions, e.g. temperature, solvent, reaction time, etc. selected for the coupling reaction are determined by the nature of the reactants and acylation method used and are known to those skilled in the art.

The acylating agents which may be used to form the N-acyl compounds of formula II are known in the literature along with methods for their synthesis or are disclosed in the examples which follow. In those cases where the acylating agent contains one or more asymmetric carbon atoms and thus exists in optically active forms, the compounds obtained using such an acylating agent are ordinarily obtained in racemic form. When the separate optical isomers are desired, the acylating agent can be resolved in a conventional manner such as by reacting the free acid with cinchonine, strychnine, brucine or the like, fractionally crystallizing to separate the diastereoisomeric salts and separately acidifying the solid phase and the liquid phase to liberate the optical isomers.

The 7-acylamido compounds of the present invention may be isolated in any of the ways customarily employed for the isolation of corresponding cephalosporin compounds. Formation of a desired pharmaceutically acceptable carboxylic acid or acid addition salt is carried out by known methods, e.g. reaction of the acid of compound II (or ester in the case of acid addition salts) with an appropriate base or acid.

At the conclusion of the acylation reaction, the product obtained may be converted (before or after removal of any protecting groups) by methods known per se to another desired product of formula II.

A compound of the formula

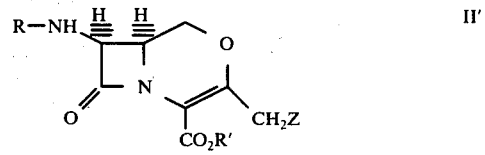

in which Z is hydroxyl and R' is an easily cleavable carboxyl-protecting group may be converted by acylation to the corresponding 7-acylamido compound in which Z is hydroxyl esterified with a carboxylic acid or a sulfonic acid residue. Acylation of the 3-hydroxymethyl group to produce carboxylic esters is preferably carried out using an acid anhydride, e.g. acetic anhydride, in the presence of an organic base such as pyridine. Other conventional acylating agents may be used including acid halides (preferably acid chlorides), mixed anhydrides or free acids in the presence of condensing agents. Methods for esterifying the 3-hydroxymethyl group of a cephalosporin are known in the literature, e.g. see U.S. Pat. No. 3,728,342, 3,532,694 and U.K. Pat. No. 1,365,954, and such methods may be used with the novel 3-hydroxymethyl β-lactam derivatives of the present invention. The sulfonic acid esters may be formed by reaction of the 3-hydroxymethyl compound with a suitable sulfonic acid derivative, most preferably with a sulfonyl halide such as methanesulfonyl chloride, p-toluenesulfonyl chloride or trifluoromethanesulfonyl chloride in the presence of an organic base. The acylating or esterifying agent used is preferably one with which will result in formation of the preferred 3-esterified hydroxyl compounds mentioned above.

A compound of formula II' in which Z is etherified hydroxyl reducible by hydrogenolysis, e.g. benzyloxy, may be converted to the corresponding 7-acylated 3-hydroxymethyl compound by catalytic hydrogenation according to methods known per se. Suitable hydrogenation catalysts include noble metals, most preferably palladium or platinum and their oxides and hydroxides, and Raney nickel, said catalysts being optionally supported on a conventional carrier such as carbon, diatomaceuous earth, etc. An especially preferred catalyst is 20% Pd (OH)$_2$. Preferred solvents for the hydrogenolysis reaction are non-reducible inert solvents such as methanol, ethanol or ethyl acetate. The reaction is preferably conducted at atmospheric or slightly elevated pressure at room temperature. When carboxyl-protecting groups present in compound II' are reducible by hydrogenolysis, e.g. benzyl, p-nitrobenzyl, benzhydryl, etc., compound II' may be simultaneously de-blocked and reduced to the desired 3-hydroxymethyl free acid.

A compound of formula II' in which Z is hydroxyl may be converted to the corresponding 7-acylated 3-etherified hydroxyl product by reacting the compound with an etherifying agent by procedures used for cephalosporin compounds, e.g. those described in U.S. Pat. No. 3,665,003.

A compound of formula II' in which Z is hydroxyl may be converted to the corresponding 3-heterocyclic ether compound by first forming a sulfonic acid ester at the 3-position, e.g. by reacting the 3-hydroxymethyl compound with a sulfonyl chloride in the presence of an organic base, and then displacing the sulfonate residue with a heterocyclic alcohol in the presence of an organic base. The 3-heterocyclic ethers may also be prepared by nucleophilic displacement of the corresponding 3-halomethyl compound, the preparation of which is described below.

A compound of formula II' in which Z is acetoxymay be converted to the corresponding 3-hydroxymethyl product by enzymatic hydrolysis, e.g. by use of citrus acetyl esterase.

A compound of formula II' in which Z is hydroxyl may be converted to the corresponding 3-halomethyl compound by reaction with a suitable halogenating agent, e.g. a phosphorus halide such as phorphorus trichloride, phosphorus tribromide, phosphorus pentachloride, phosphorus pentabromide, phosphorus oxychloride, or phosphorus oxybromide. The 3-iodomethyl compounds may also be formed by treating the 3-bromomethyl or 3-chloromethyl compound with an alkali metal iodide.

Compounds of formula II' in which Z is hydroxyl may be converted to the corresponding compounds having Z = —OCONH$_2$ by reaction in an inert organic solvent, e.g. benzene, with a source of cyanate ions, e.g., from an alkali metal cyanate, followed by treatment with trifluoroacetic acid. The cyanate ion and trifluoroacetic acid are preferably each employed in a molar ratio of about 2:1 with respect to the hydroxymethyl starting material.

A compound of formula II in the form of the free acid or a salt thereof may be converted to a pharmaceutically acceptable salt thereof or to a physiologically hydroylzed ester or pharmaceutically acceptable salt thereof. Similarly, the product of formula II" in the form of an easily cleavable ester or salt thereof may be converted to the free acid product or a pharmaceutically acceptable salt thereof by removal of the esterifying group to form the free acid, e.g. by acidic or alkaline hydrolysis, by enzymatic hydrolysis (as with human or animal serum), by hydrogenolysis or by treatment with chemical reagents known to remove particular blocking groups, e.g. sodium thiophenoxide as in U.S. Pat. No. 3,284,451, and subsequent treatment of the free acid with an acid or base to form a pharmaceutically acceptable salt.

The easily cleavable esters of the compounds of formula II are useful as intermediates in the production of the free acid product. The pivaoloyoxymethyl, acetoxymethyl, phthalidyl, indanyl and methoxymethyl esters are also useful as active antibacterial agents since on oral administration they are rapidly hydrolyzed to the active metabolite. These esters are of particular interest because they provide on oral administration different rates and amounts of absorption and give differing concentrations of the active antibacterial agent in blood and tissues.

The 7-amino intermediates of general formula III may be prepared by selectively reducing a 7-azido intermediate of the formula

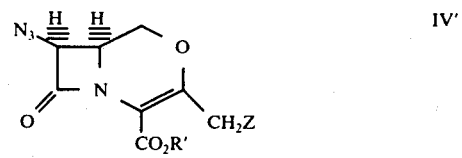

IV' wherein Z is halo, hydroxyl, etherified hydroxyl or hydroxyl esterified with a carboxylic acid or sulfonic acid residue and R' is an easily cleavable ester carboxyl-protective group. The carboxyl-protected compound may, if desired, be cleaved to produce the free-acid intermediate III which can be converted to a salt by methods known per se.

Preferred reducing agents for use in preparing the intermediates of formula III include chemical reducing agents such as zinc and ammonium chloride, aluminum amalgam and hydrogen sulfide in the presence of a base, e.g. triethylamine or ammonia. Catalytic hydrogenation may also be employed with such catalysts as noble metals, preferably platinum or palladium including derivatives thereof such as oxides, hydroxides and halides, or Raney nickel, said catalysts being optionally supported on a conventional carrier such as carbon or diatomaceous earth. Catalytic hydrogenation is performed with a non-reducible inert solvent, e.g. methanol, ethanol or ethyl acetate, and preferably at atmospheric or slightly elevated pressure at room temperature.

Compound III in the carboxyl-protected form or a salt thereof may be used directly as a starting material in the N-acylation process discussed above. Alternatively, the protected intermediate may be de-blocked to form the free carboxylic acid which may then be optionally converted to a salt or to another carboxyl-protected form, e.g. a physiologically hydrolyzed ester or salt thereof. By proper selection of reduction conditions and protecting groups, azido intermediate IV' may be converted either simultaneously or in stepwise fashion to the 7-amino free acid III. Thus, if mild hydrogenation conditions are used, e.g. catalytic hydrogenation with 10% Pd-on-charcoal or a mild chemical reducing agent such as $H_2S$ in the presence of a base such as triethylamine or ammonia, the azido group may be reduced without concomitant removal of esters resistant to such conditions, e.g. benzyl or p-nitrobenzyl. If stronger reducing conditions are used such as 30% Pd-on-diatomaceous earth, both the azido group and most reducible esters will be simultaneously reduced. When it is desired to prepare an intermediate III where Z is etherified hydroxyl, it may be necessary to select sufficiently mild reducing conditions, e.g. $H_2S$ with base, so as not to affect a reducible ether moiety.

A preferred embodiment of the present invention is the process comprising the consecutive steps of 1. selectively reducing a 7-azido intermediate of the formula IV' where Z is halo, hydroxyl, hydroxyl esterified with a carboxylic acid or sulfonic acid residue or etherified hydroxyl and R' is an easily cleavable ester carboxyl-protecting group to produce a carboxyl-protected 7-amino intermediate of formula III and, if desired, removing the carboxyl-protecting group to produce the corresponding free acid intermediate of formula III or optionally a salt thereof; and 2. N-acylating intermediate III or a salt thereof with an acylating acid of the formula R-COOH where R is an acyl group, or with its functional equivalent as an acylating agent for a primary amine and, if desired, converting the so-produced product to the corresponding 7-acylated product having a substituent Z as defined above different from that in compound III and, if desired, (a) when R" is a carboxyl-protecting group, converting the 7-acylated ester to the free acid compound or a physiologically hydrolyzed ester or a pharmaceutically acceptable salt of said acid or ester, or (b) when R" is hydrogen, converting the 7-acylated carboxylic acid to a physiologically hydrolyzed ester or a pharmaceutically acceptable salt of said acid or ester and, if desired, resolving a resulting isomer mixture into its component isomers.

The 7β-azido intermediates IV' may be prepared by various methods depending on the nature of substituent Z. When Z is a group $-OCOR_2$ derived from an acid $R_2COOH$ having a $pK_a$ of between 3.5 to 5.5 and wherein $R_2$ is hydrogen, amino, (lower)alkyl, $C_3-C_7$ cycloalkyl, $C_3-C_7$ cycloalkyl-(lower)alkyl, aryl, aralkyl or aryloxyalkylene, said $R_2$ groups being optionally substituted by one or more radicals selected from (lower)alkoxy, (lower) alkylthio, halogen, (lower)alkyl nitro, hydroxy, acyloxy, carboxy, amino, (lower)alkylamino or acylamino, intermediates of formula IV' may be prepared by cyclizing in an inert organic solvent a compound of the formula

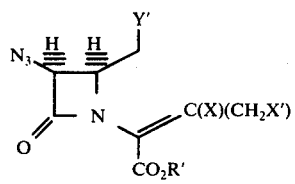
V wherein X and X' which may be the same or different each represent a halogen atom, preferably bromine, or iodine and most preferably iodine, R' is an easily cleavable ester carboxyl-protecting group and Y' represents a suitable leaving group, preferably a group such as halo or sulfonyloxy, e.g. alkyl- or substituted alkylsulfonyloxy or aryl- or substituted arylsulfonyloxy and most preferably a group selected from halo, $-OSO_2$-(lower)alkyl including especially $-OSO_2CH_3$, $-OSO_2CF_3$ and $-OSO_2C_6H_4CH_3$, with a base selected from an anion of the formula $R_2COO^{31}$ derived from a carboxylic acid having a $pK_a$ of between about 3.5 and 5.5 and in which $R_2$ is as defined above.

The dihalide starting material V may be used in either of its isomeric forms

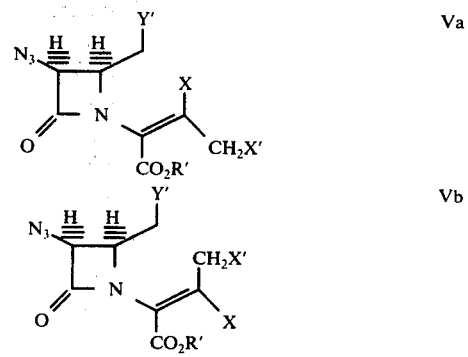

or as a mixture of isomers. Formula V above is intended to represent either of the individual isomers or the mixture. Any dihalide including a mixed dihalide, e.g. X = Cl, X' = Br, may be used but the most preferred compound is the diiodide. Compound V is reacted in an inert organic solvent, preferably a polar organic solvent such as dimethylformamide, with an excess of the base.

Any base derived from a carboxylic acid $R_2COOH$ satisfying the $pK_a$ conditions above and wherein $R_2$ is as defined above may be employed in the cyclization reaction. The preferred bases are the anions of the formula $R_2COO^-$ in which $R_2$ is hydrogen, (lower)alkyl and especially methyl, phenoxymethyl and tetrazolylmethyl. The most preferred bases are the formate and acetate anions, e.g. from an alkali metal, ammonium or substituted ammonium formate or acetate.

The leaving group Y' should be one which is efficiently displaced under the conditions of the base cyclization reaction. Suitable leaving groups include halo and sulfonyloxy groups, i.e., allkyl- or substituted alkylsulfonyloxy or aryl- or substituted arylsulfonyloxy. A most preferred Y' leaving group is the mesylate group.

Cyclization of compound V is conveniently carried out at room temperature or below.

Starting materials of formula V used in the above process may be prepared as described below in the section entitled "Preparation of Starting Materials." Briefly summarized, the reaction scheme is as shown in Flow Sheet I:

Flow Sheet 1

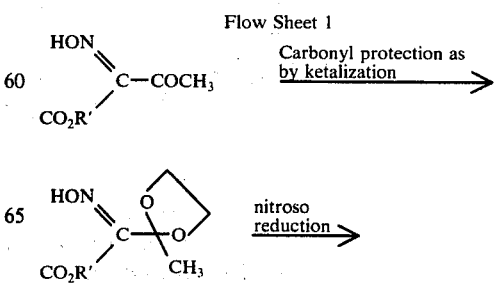

-continued

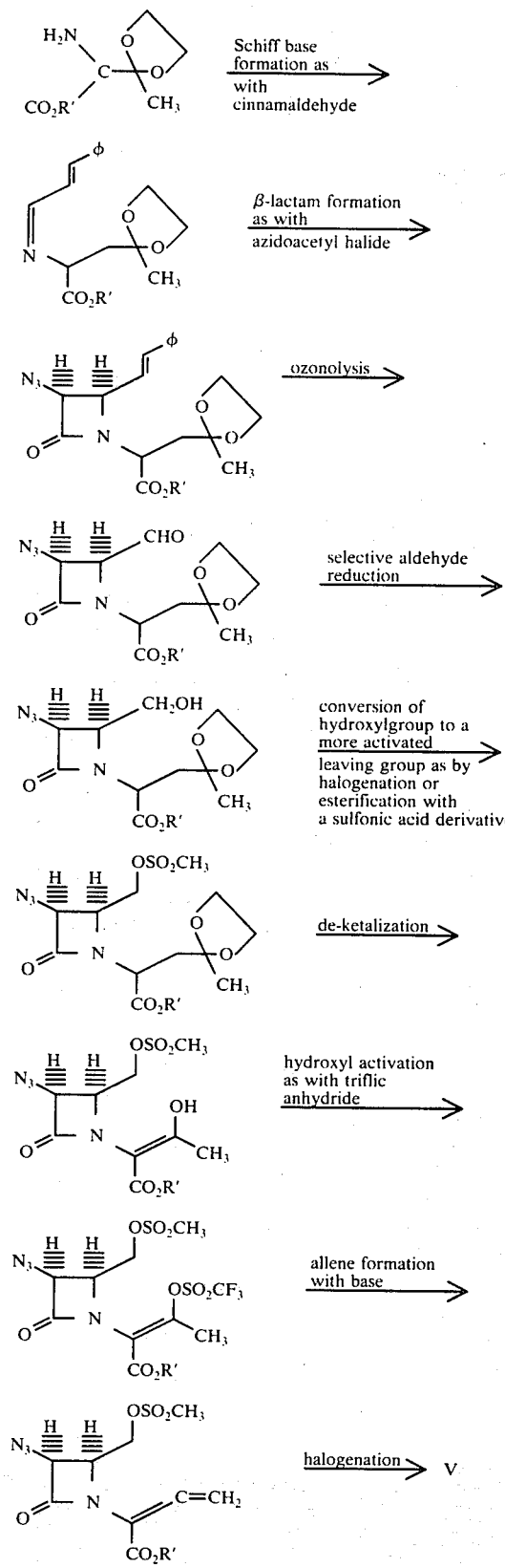

Intermediates of formula IV' having Z either -OCHO or —OCOR$_2$ in which R$_2$ is (lower)alkyl may be converted to the corresponding intermediates of formula IV' wherein Z is hydroxyl by subjecting such compounds to acid hydrolysis, e.g. by treatment with a mineral acid in an aqueous acetone solvent system.

Intermediates of formula IV' in which Z is hydroxyl esterified with a carboxylic acid or sulfonic acid residue may be prepared by esterifying a 3-hydroxymethyl intermediate of the formula

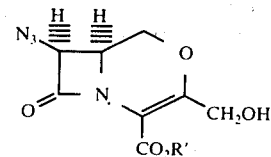

with a carboxylic acid or sulfonic acid agent capable of introducing the desired acyloxy or sulfonyloxy acyl moiety at the 3-position. Esterification in this embodiment of the present invention may be performed in the same manner as described previously in connection with the modification of the Z substituents in compounds of formula II. A preferred embodiment comprises reacting an intermediate IV' in which Z is hydroxyl with acetic anhydride in the presence of an organic base to prepare the corresponding carboxyl-protected 3-acetoxymethyl 7-azido intermediate.

Another preferred embodiment involves esterifying intermediate IV' in which Z is hydroxyl with an esterifying derivative of methanesulfonic acid, trifluoromethanesulfonic acid or p-toluenesulfonic acid, e.g. methanesulfonyl chloride, p-toluenesulfonyl chloride or triflic anhydride, in the presence of an organic base, e.g. triethylamine, and in an inert organic solvent, e.g. methylene chloride, to produce an intermediate of formula IV' in which Z is methanesulfonyloxy, p-toluenesulfonyloxy or trifluoromethylsulfonyloxy.

Intermediates of formula IV' in which Z is hydroxyl may be converted to the corresponding 3-halomethyl compounds by reaction with a halogenating agent, e.g. a phosphorus halide such as phosphorus trichloride, phosphorus tribromide, phosphorus pentachloride, phosphorus pentabromide, phosphorus oxychloride or phosphorus oxybromide. The 3-iodomethyl compounds may also be formed by treating the 3-bromomethyl or 3-chloromethyl compound with an alkali metal iodide.

Intermediates of formula IV' in which Z is 3-halomethyl or 3-sulfonyloxy may be converted to the corresponding 3-heterocyclic ether intermediates by nucleophilic displacement with a heterocyclic alcohol in the presence of an organic base.

Carbamate intermediates of the formula

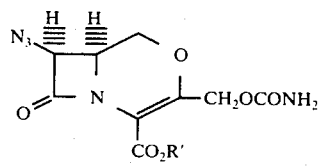

may be prepared by reacting the corresponding carboxylprotected 7-azido 3-hydroxymethyl compound in an inert organic solvent, e.g. benzene, with a source of cyanate ions, e.g. an alkali metal cyanate, followed by treatment with trifluoroacetic acid. The cyanate ion and trifluoroacetic acid are preferably each employed in approximately a 2:1 molar ratio with respect to the azido starting material.

An alternate method provided by the present invention for preparation of intermediates of formula IV' where Z is hydroxyl comprises cyclizing with base in an inert organic solvent an intermediate of the formula

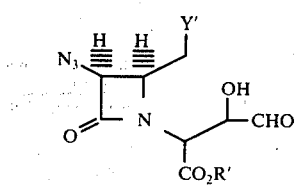

VI wherein R' is an easily cleavable ester carboxylprotecting group and Y' represents a suitable leaving group, preferably a halo or a sulfonyloxy group, e.g. alkyl- or substituted alkylsulfonyloxy or aryl- or substituted arylsulfonyloxy and most preferably a group selected from halo, $-OSO_2$-(lower)alkyl including especially $-O-SO_2CH_3$, $-OSO_2CF_3$ and $-OSO_2C_6H_4CH_3$.

The base used in the cyclization of VI may be selected from a wide variety of bases including especially bases of the following categories:

a. anions derived from carboxylic acids having a $pk_a$ of between 3.5 and 5.5;
b. tertiary organic amines such as a trialkylamine (e.g., triethylamine), pyridine, N-methylpiperidine, N-methylmorpholine, etc.;
c. alkali metal hydrides, e.g., sodium or potassium hydride; and
d. organolithium compounds including especially lithium alkyls, e.g., methyl lithium or butyl lithium.

Most preferred cyclization bases are the acetate and formate anions, e.g., from alkali metal, ammonium or substituted ammonium formates or acetates. The most preferred base is the acetate anion. The base is preferably used in a molar excess relative to compound VI, and the reaction is conducted in an inert organic solvent, preferably a polar organic solvent such as dimethylsulfoxide or dimethylformamide. The temperature for the cyclization is not critical, and room temperature may be used for convenience.

Compound VI used in the above process may be prepared by the procedures described below in the section entitled "Preparation of Starting Materials". A summary of the reaction scheme is shown in Flow Sheet 2:

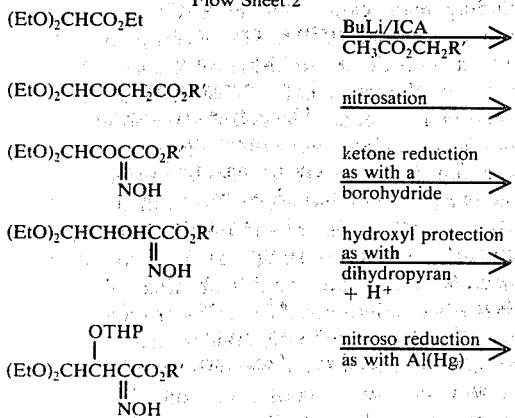

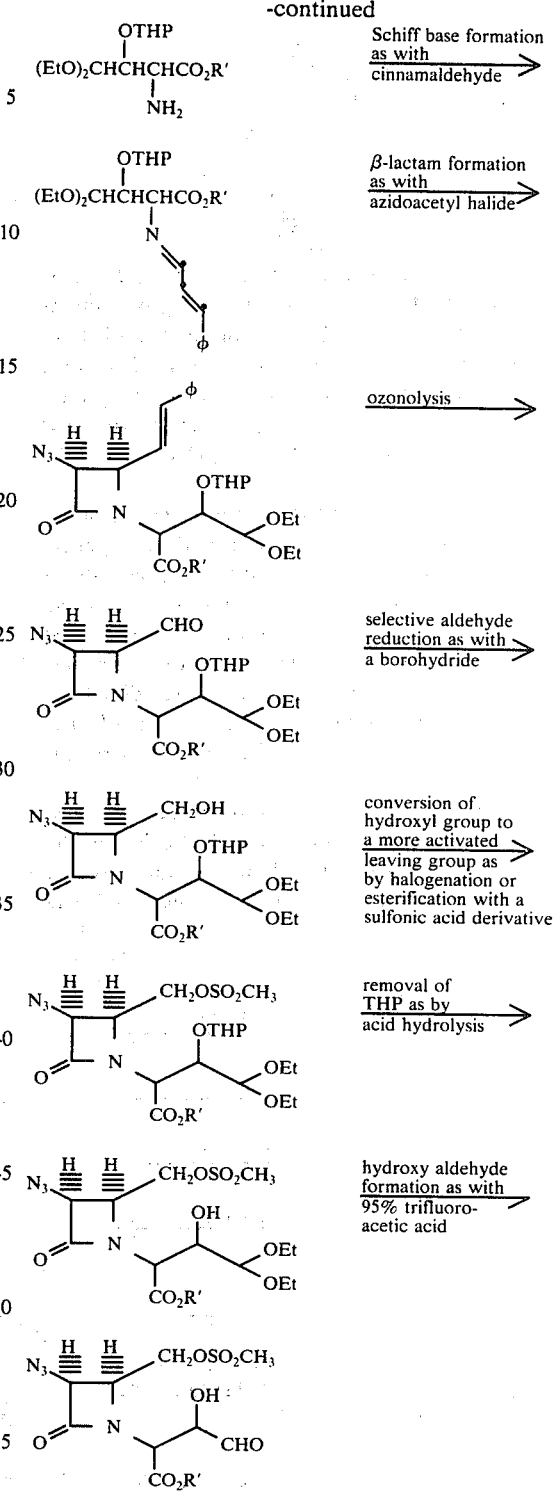

Et = $C_2H_5$—
ICA = isopropylcyclohexylamine
THP = tetrahydropyran
φ = $C_6H_5$—

The 7β-azido intermediates of formula IV' where Z is etherified hydroxyl may be prepared by cyclizing with base in an inert organic solvent an enol intermediate of the formula

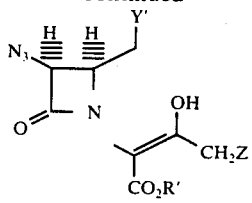

wherein Z is an etherified hydroxyl group, R' is an easily cleavable ester carboxyl-protecting group and Y' represents a suitable leaving group, preferably a halo or sulfonyloxy, e.g. alkyl- or substituted alkylsulfonyloxy or aryl- or substitued arylsulfonyloxy and most preferably a group selected from halo, —OSO$_2$-(lower)alkyl including especially —OSO$_2$CH$_3$, —OSO$_2$CF$_3$ and —O-SO$_2$C$_6$H$_5$CH$_3$.

The base used to cyclize enol VII may be any of the bases mentioned above in connection with the cyclization of intermediate VI and is preferably an acetate or formate anion and most preferably the acetate anion, e.g., from an alkali metal, ammonium or substituted ammonium acetate. Cyclization is carried out in an inert organic solvent, e.g., methylene chloride, dimethylformamide or dimethylsulfoxide, with an excess of base, and may conveniently be done either at room temperature or under reflux.

Compound VI used in the above process may be prepared by the general method described below in the section entitled "Preparation of Starting Materials". A summary of the reaction scheme is shown in Flow Sheet 3:

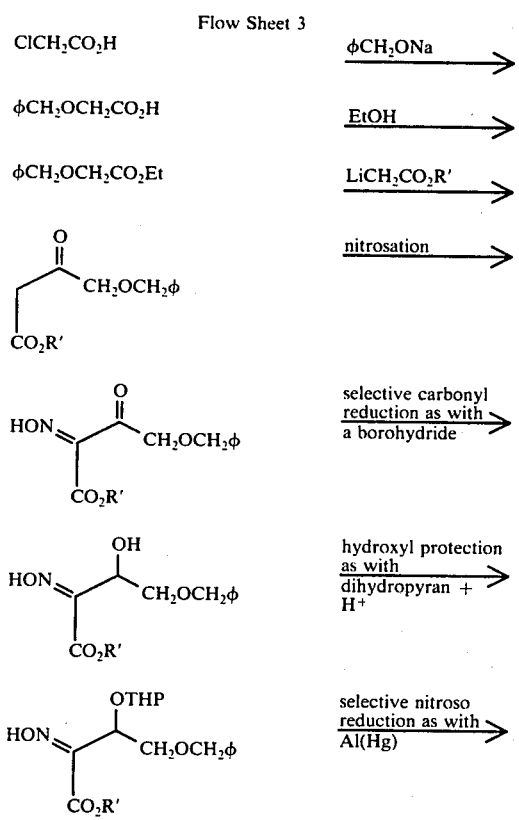

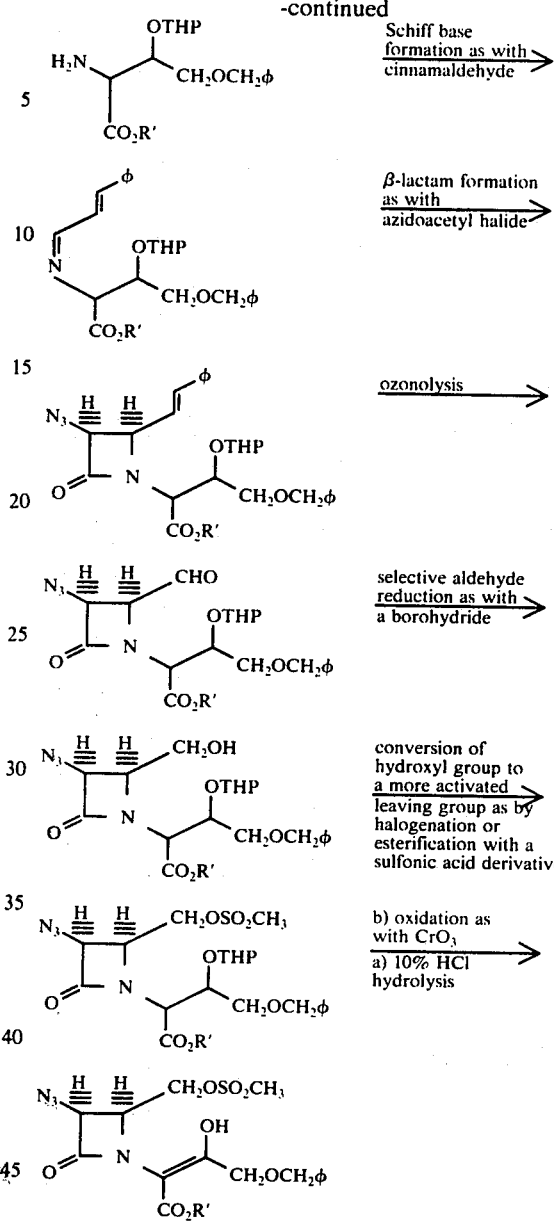

The pharmaceutically active compounds of the present invention are potent antibacterial agents useful in the treatment of infectious diseases in poultry and animals, including man, caused by many Gram-positive and Gram-negative bacteria. The active compounds are also of value as nutritional supplements in animal feeds and as agents for the treatment of mastitis in cattle.

The novel medicaments provided by the present invention may be formulated as pharmaceutical compositions comprising, in addition to the active ingredient, a pharmaceutically acceptable carrier or diluent. The compounds may be administered both orally and parenterally. The pharmaceutical preparations may be in solid form such as capsules, tablets or dragees, or in liquid form such as solutions, suspensions or emulsions. In the treatment of bacterial infections in man, the active compounds of this invention may be administered parenterally or orally in an amount of from about 5 to 200 mg/Kg./day and preferably about 5 to 20 mg./Kg./day in divided dosage, e.g. three or four times a day. They are administered in dosage units containing, for example, 125, 250 or 500 mg. of active ingredient with suitable physiologically acceptable carriers or excipients.

Illustrative examples of the preparation of starting materials and compounds of the present invention follow. These examples are given in illustration of, but not in limitation of, the present invention. All temperatures are in degrees Centigrade. DMF represents dimethylformamide, THF stands for tetrahydrofuran and EEDQ is the amide bond forming reagent having the structure

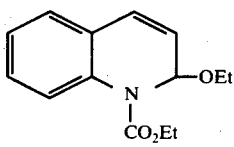

The 7-acylamido compounds prepared in the examples which follow all have the hydrogen atoms at carbons 6 and 7 cis with respect to each other and, unless indicated, the products are racemic mixtures in the sense that they are composed of equal parts of the two isomers having the following structures:

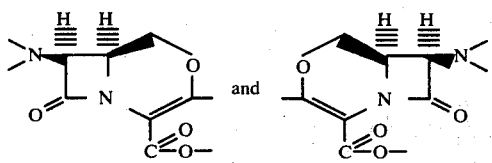

PREPARATION OF STARTING MATERIALS

1. Preparation of intermediates of formulae

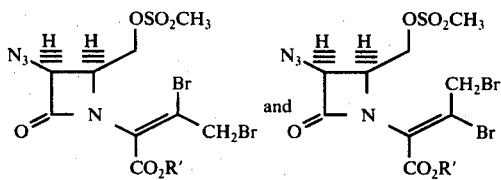

Benzyl Oximino-Acetoacetate

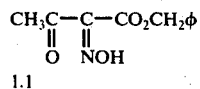

1.1

The procedure was essentially the same as that used to make the corresponding ethyl ester by H. Adkins and J. Reeve, JACS 60, 1328 (1938).

In a three necked one liter flask fitted with a thermometer, a dropping funnel and a magnetic stirrer were placed 173 g. (0.9 mole) of benzyl acetoacetate [The benzyl acetoacetate was prepared as described by Baker et al., J. Org. Chem. 17, 91 (1952)] and 130 ml. of glacial acetic acid. The contents were cooled in an ice bath and a solution of 69 g. (1 mole) of sodium nitrite in 130 ml. of water was added over a period of half an hour; the temperature was kept at 0° to 10° C. After the reaction mixture was stirred for one hour at room temperature, 400 ml. of water was added and the stirring was continued for an additional two hours. The reaction mixture was extracted three times with 200 ml. portions of diethyl ether. The diethyl ether extracts were combined, washed once with water, three times with saturated sodium bicarbonate solution and once with brine. After drying over anhydrous sodium sulfate, the diethyl ether solution was evaporated leaving [1.1] as a clear oil which solidified upon trituration with petroleum ether (30° – 60°) to give 186.5 g. (93.2%) of white solid. Its NMR spectrum was consistent with the assigned structure. Generally the product was used as such in subsequent reaction but it can be recrystallized from toluene, m.p. 81° – 82° C.

Benzyl Oximino-Acetoacetate Ethylene Ketal

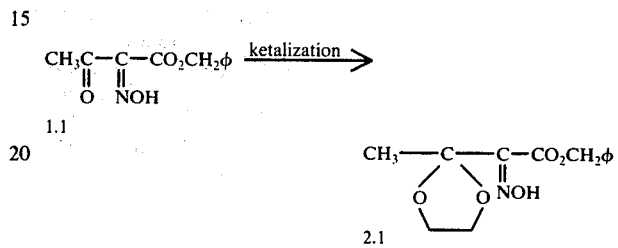

In a two liter flask fitted with a Dean Stark water separator and a condenser were placed 186.5 g. (0.85 mole of benzyl oximino-acetoacetate [1.1], 62 g. (1 mole) of ethylene glycol, 800 ml. of benzene (reagent grade) and 2 g. (10.5 mmole) of p-toluenesulfonic acid monohydrate. The reaction mixture was boiled at reflux until 15 ml. of water was removed (3 hours). The benzene solution was washed once with saturated sodium bicarbonate solution and once with brine. After drying over anhydrous sodium sulfate, the benzene solution was evaporated, leaving 212 g. (94% yield) of benzyl oximinoacetoacetate ethylene ketal [2.1] as a light yellow oil! Its NMR spectrum was consistent with the assigned structure. Generally, the product was used as such in subsequent reactions but one of the isomers can be crystallized[2] from toluene-petroleum either (b.p. 30°-60° C.); m.p. 52° C.

Anal. Calc'd. for $C_{13}H_{15}NO_5$: C, 58.86; H, 5.70; N, 5.28. Found: C, 58.97; H, 5.68; N, 5.12.

1. A mixture of the syn and anti isomers.
2. Only 35% of the oil could be crystallized.

Benzyl Amino-Acetoacetate Ethylene Ketal

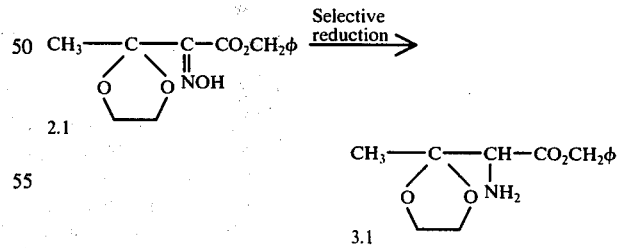

Freshly prepared aluminum amalgam[1] (from 27 g. of aluminum foil) in a three-necked one liter flask was covered with 500 ml. of diethyl ether. The flask was fitted with a mechanical stirrer, a condenser, and a dropping funnel. A solution of benzyl oximino-acetoacetate ethylene ketal [2.1] (132.5 g.; 0.5 mole) in 300 ml. of wet diethylether[2] was added dropwise at such a rate as to maintain boiling at reflux. After stirring for four hours, the reaction mixture was filtered through a Buchner funnel. The filtrate was evaporated leaving 110 g. of yellowish oil. The oil was dissolved in 800 ml. of dry diethylether and dry hydrogen chloride gas was bubbled into the solution until no further precipitation occurred. The white precipitate was filtered off and washed once with diethylether and then dried in vacuo. This provided 108 g. of benzyl aminoacetoacetate ethylene ketal hydrochloride[3] [3.1]; m.p. 157°–158° C.

Anal. Calc'd. for $C_{13}H_{17}NO_4 \cdot HCl$: C, 54.26; H, 6.31; N, 4.87. Found: C, 53.96; H, 6.19; N, 4.60.

To obtain the free base, the hydrochloride salt was suspended in 500 ml. of diethylether and concentrated ammonium hydroxide was added with shaking until the solid went into solution. The diethylether layer was separated and washed twice with brine. After drying over anhydrous sodium sulfate, the solvent was evaporated leaving 90 g. (71% yield) of colorless oil.

1. The aluminum amalgam was prepared essentially as described in A. I. Vogel ("Practical Organic Chemistry", 3rd., Edn., Longemans Green & Co., London, (1957), p. 198) except for the following modification:
   a. 5% NaOH was used.
   b. The second washing with ethanol was omitted.
   c. Dry diethylether was used for washing and most of the water must be drained.
2. The diethylether was saturated with water by shaking with water in a separatory funnel.
3. The product can be stored as the hydrochloride salt.

Schiff Base Formation and β-Lactam Formation

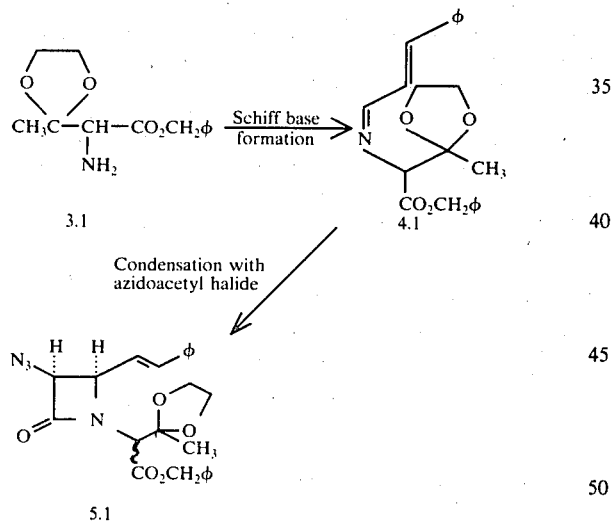

In a one liter flask fitted with a Dean Stark water separator and a condenser were placed 70.3 g. (0.28 mole) benzyl aminoacetoacetate ethylene ketal [3.1], 37 g. (0.28 mole) cinnamaldehyde, and 750 ml. of methylene chloride (reagent grade). The mixture was boiled at reflux for 30 minutes and then 400 ml. of methylene chloride were distilled off. The concentrated solution was then dried over anhydrous sodium sulfate and then evaporated to dryness in vacuo[1]. The residual oil was checked by NMR to ensure hat Schiff base formation was complete before continuing on to the next step.

The freshly prepared Schiff base [4.1] was diluted with 600 ml. of methylene chloride[2] and cooled to 0° C. (ice-salt bath). Triethylamine (31.1 g.; 0.308 mole) was added and then a solution of 36.2 g. (0.308 mole) of azidoacetyl chloride[3] in 362 ml. of methylene chloride[2] was added dropwise at 0° C. over a period of one hour. The reaction mixture was stirred for an additional hour at room temperature[4] and then evaporated on a rotary evaporator at reduced pressure while being heated on a 35° C. water bath[5]. The residue was diluted with 500 ml. of diethylether and filtered. The filtrate was washed twice with brine and dried over anhydrous sodium sulfate. Evaporation of this solution yielded 117.5 g. (94% yield) of styryl β-lactam [5.1]. Its NMR and IR spectra are consistent with the assigned structure and indicate the presence of a mixture of isomers, diasteriomeric at the carbon α to the carbonyl of the benzyl ester.

1. This evaporation must be done to ensure complete Schiff base formation.
2. All the methylene chloride used in the cyclo-addition reaction was reagent grade which was first dried over molecular sieve (Type 4A) and then over anhydrous calcium chloride. It was stored thereafter over molecular sieve (Type 4A).
3. J. H. Boyer and J. Horner, J. Amer. Chem. Soc., (1955), 77, 951.
4. The reaction mixture can be kept overnite at 0° if necessary.
5. This operation is necessary to ensure complete β-lactam formation.

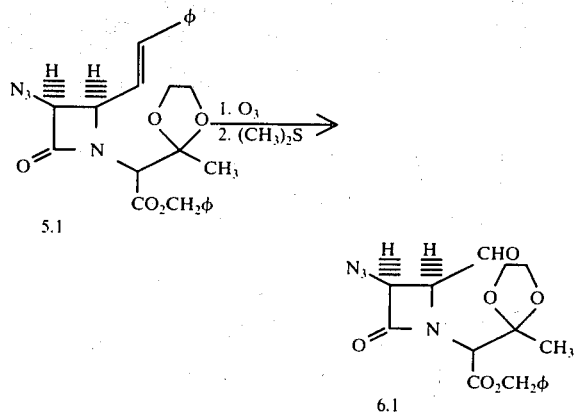

Styryl β-lactam [5.1] (117.5 g.; 0.262 mole) was dissolved in one liter of methylene chloride (reagent grade), cooled to −50° to −60° C. in a dry ice-acetone bath, and ozonized until a faint blue-green color appeared. The solution was then flushed with nitrogen until the color faded. Methylsulfide (100 ml.) was added to the −50° C. solution, which was then allowed to slowly reach 25° as the cooling bath gradually melted. It was kept overnite at room temperature under nitrogen and then it was washed twice with 1% sodium bicarbonate solution, twice with brine, dried over anhydrous sodium sulfate, and evaporated to dryness. The resulting oil triturated four times with 100 ml. portions of petroleum ether (b.p. 30°–60° C.) to remove benzaldehyde. The oil was then triturated carefully with diethylether whereupon it solifified. The solid was filtered off and dried to provide 75 g. (71.5%) of aldehyde [6.1] as a mixture of isomers diasteriomeric at the carbon α to the carbonyl of the benzyl ester. Recrystallization of [6.1] from ether gave white crystals, m.p. 110°–102° C. (corrected).

Anal. Calc'd. for $C_{17}H_{18}N_4O_6$: C, 54.54; H, 4.84; N, 14.96. Found: C, 54.75; H, 4.87; N, 14.89.

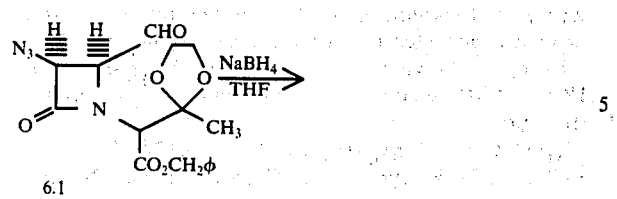

6.1

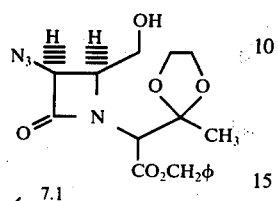

7.1

Conversion of hydroxyl group to / more active leaving group as by esterification with methanesulfonyl halide

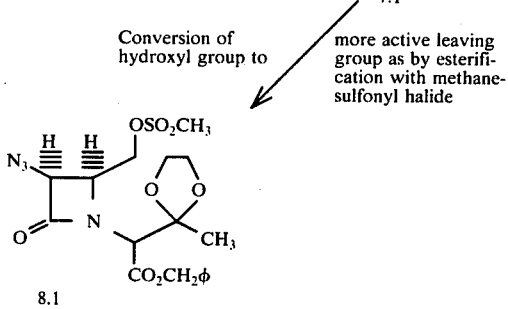

8.1

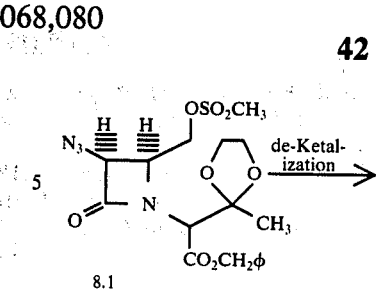

8.1

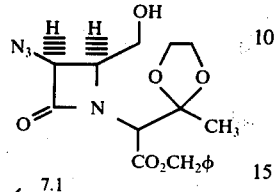

9.1

Hydroxyl activation as by / triflic anhydride

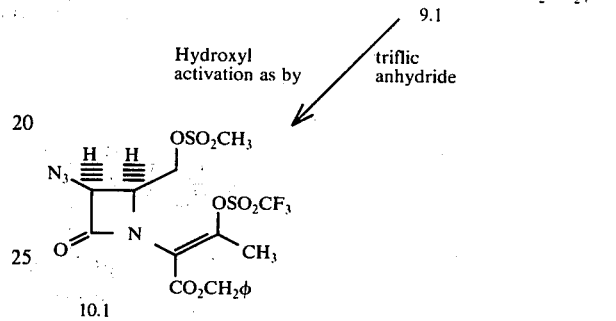

10.1

The aldehyde [6.1] (116.3 g.; 0.31 mole) was dissolved in 600 ml. of THF (reagent grade) and the solution was then cooled to −10° C. (ice-methanol bath). Sodium borohydride (5.88 g.; 0.155 mole) was added and the reaction mixture was stirred 1 hour. 10% aqueous hydrochloric acid was added until the mixture was slightly acidic, then 600 ml. brine was added. The THF layer was separated and the aqueous phase was extracted twice with 250 ml. portions of diethylether. The combined organic phases were washed twice with 400 ml. portions of brine, dried over anhydrous sodium sulfate, and evaporated in vacuo to yield 117.3 g. of crude alcohol [7.1] as an orange oil. This oil was used as such in the next reaction.

A solution of methanesulfonyl chloride (37.8 g.; 0.34 mole) in 100 ml. of methylene chloride[1] was added dropwise at 0° C. (ice-water bath) to a stirring solution of alcohol [7.1] (105.6 g.; 0.28 mole, triethylamine (56.6 g.; 0.34 mole) and one liter of methylene chloride[1]. Afterwards, the reaction was stirred for 30 hours at 25° C. It was then washed twice with brine (500 ml. portions), dried over anhydrous sodium sulfate, and evaporated in vacuo. The resulting oil was dissolved in methylene chloride, treated with norite, and then filtered over approximately 200 g. of activity I silica gel. The silica gel was then washed with approximately 2 liters of methylene chloride. The filtrate was evaporated to dryness and the resulting oil (116 g.) was covered with diethylether. It crystallized on standing to give 87.2 g. (80% from [6.1] of mesylate [8.1] as offwhite solid, m.p. 97°–99° C (corrected).

1. The methylene chloride used was reagent grade which had been further purified by passing over a column of calcium chloride and then storing over molecular sieve (Type 4A).

A mixture of mesylate [8.1](3.19 g.; 6.43 mmole) and 30 ml. of 95% trifluoroacetic acid was stirred at 25° for 2 hours. The mixture was diluted with 300 ml. of brine and extracted three times with methylene chloride (100 ml. portions). The combined extracts were washed three times with water (50 ml. portions, until neutral), dried (anhydrous sodium sulfate) and evaporated to dryness in vacuo leaving 3.17 g. of a brown oil. NMR spectra of this oil indicate the presence of >90% enol [9.1].

Crude enol [9.1]](48.0 g.; 0.117 mole) and triflic anhydride (33.0 g.; 0.117 mole) were dissolved in 500 ml. of methylene chloride and the solution was then cooled to 0° C. (ice-water bath). A solution of triethylamine (11.8 g.; 0.117 mole) in 80 ml. of methylene chloride[2] was added dropwise over a period of 40 minutes. When the addition was complete, the ice-water bath was removed and the mixture was stirred at 25° for 45 minutes. The mixture was then poured into 300 ml. of ice water and washed with cold water until the pH of the washings was approximately 6. The extract was dried (anhydrous sodium sulfate) and evaporated in vacuo to give 54.0 g. of crude triflate [10.1] as a dark red oil. This oil dissolved in 400 ml. of benzene (USP) and passed through a 1½ inch pad of activity III silica gel. The pad was washed with 1 l. of benzene. Evaporation of the benzene gave 38.3 g. of a yellow oil. This oil was carefully triturated with 50 ml. of absolute ethanol and then cooled at 0° C. for 2 hours. The resulting white solid was filtered off and dried in vacuo to give 19.5 g. of triflate [10.1] as one isomer, m.p. 57°–59° C. (corrected).

Anal. Calc'd. for $C_{17}H_{17}F_3N_4O_4S_2$: C, 37.67; H, 3.14; N, 10.33; S, 11.82. Found: C, 37.40; H, 3.12; N, 10.43; S, 11.73.

1. Triflic anhydride was prepared as follows: 170 g. (100 ml.) $CF_3SO_3H$ ("Fluorochemic acid" 3M Company) and 135 g. $P_2O_5$ were mixed carefully, shaken well, and stored 18 hours protected from moisture. The product was distilled from the resulting solid mass using a flame; the fraction boiling 80°–90° C. was collected. Re-distillation of this fraction yielded 119.45 g. (74%) of triflic anhydride boiling 82°–84° C.

2 The methylene chloride used was reagent grade which had been further purified by passing over a column of calcium chloride and then stored over molecular sieve (Type 4A).

washed with water, dried, decolorized, filtered and the solvent evaporated in vacuo to give the diiodide [23.1] (588 mg.; 91% yield) in greater than 95% purity. The IR and NMR spectra were consistent for the proposed structures.

Anal. Calc'd. for $C_{16}H_{16}N_4O_6I_2S$: C, 29.74; H, 2.50; N, 8.67; I, 39.28; S, 4.96. Found: C, 29.76; H, 2.47; N, 8.61;

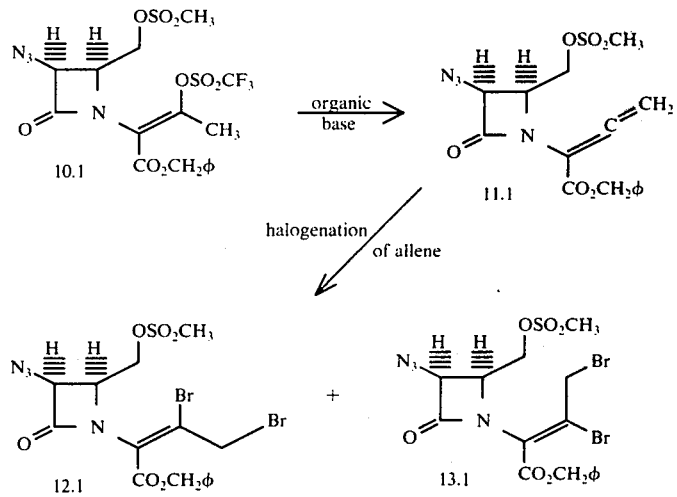

Triethylamine (1 g.; 0.01 mole) was added to a stirred solution of triflate [10.1] (5.42 g.; 0.01 mole) in 55 ml. of methylene chloride (A.R.) at room temperature. After stirring for five minutes (at which point TLC shows complete formation of allene [11.1], a solution of bromine (10 ml. of 1M solution in $CCl_4$; 0.01 mole) was added dropwise. After addition of the bromine, the mixture was concentrated, absorbed onto Activity I silica gel and dry column chromatographed on Activity I silica gel by eluting with methylene chloride (USP). This yielded one fraction (uniformly one spot by TLC) weighing 2.5 g. (45%). Its IR, UV, and NMR spectra were consistent with the expected dibromide structure [13.1].

Anal. Calc'd for $C_{16}H_{12}Br_2N_4O_6S$: C, 34.80; H, 2.92; N, 10.15. Found: C, 35.25; H, 2.97; N, 10.02.

1A. Preparation of intermediates of formulae

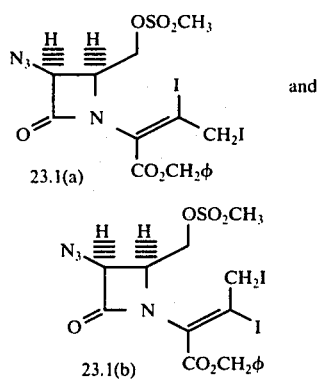

and

A solution of triethylamine (101 mg., 1.00 mmole) in 1.4 ml. of methylene chloride was added with stirring to a solution of triflate [10.1] (542 mg., 1.00 mmole) in 5.4 ml. of methylene chloride at 0° C. After allowing the solution to warm to 24° over 15 minutes, a solution of iodine (254 mg., 1.00 mmole) in 7.5 ml. of methylene chloride was added with stirring over 30 minutes, then

I, 39.37; S, 5.18.

2. Preparation of intermediates of formula

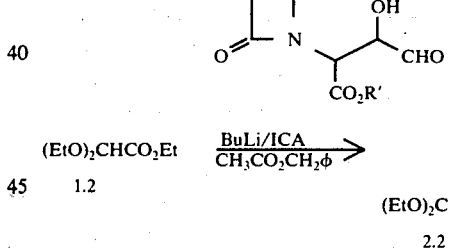

Butyl lithium (1.1 moles, 2.4 M in hexane) was added under an atmosphere of dry nitrogen to 1 liter of dry tetrahydrofuran (freshly distilled from lithium aluminum hydride) at −60° C. It was followed by the dropwise addition of isopropylcyclohexylamine (dried over potassium hydroxide pellets) (200 ml., 1.1 moles) and then benzyl acetate (165 g., 1.1 moles). After stirring for three-fourths hour at −60° C., it was treated fairly rapidly with diethoxy ethyl acetate [1.2][1] (178 g., 1.01 moles). The mixture was allowed to come slowly to 20° C. It was then cooled to 0° C. and acidified with 10% hydrochloric acid. Ether was added and the ether extract was washed with water (twice) and then brine. It was dried over anhydrous sodium sulfate and evaporated to give 283 g. (100%) of β-keto ester [2.2] of suitable purity to be used directly.

1. Prepared by the method of R. Moffett (Organic Synthesis, Coll. Vol. IV, p. 427) or more conveniently by the method of E. Bisagni et al. (Bull. Soc. Chim. Fr. 1968, 637).

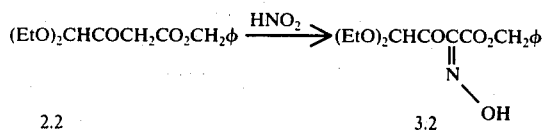

2.2    3.2

A solution of the β-keto ester [2.2] (283 g., 1.01 moles) in glacial acetic acid (300 ml.) was cooled to 0° C. and treated dropwise below 5° C. with a solution of sodium nitrite (100 g., 1.45 moles) in 250 ml. of water. By the end of the addition, the solid product has begun to form. After coming to room temperature over 1 ½ hours, it was treated slowly with 400 ml. of water. The solid was collected by filtration and washed with cold water.

This solid was then dissolved in 1 liter of ether and washed with water and brine. It was dried over anhydrous sodium sulfate and evaporated to give 288 g. (93%) of the oxime [3.2] which was used without further purification.

For analysis, a sample was crystallized twice from ether/petroluem ether (b.p. 30°-60°) giving white needles with m.p. 95°-97° C.

Anal. Calc'd. for $C_{15}H_{19}NO_6$: C, 58.24; H, 6.19; N, 4.53. Found: C, 58.28; H, 6.37; N, 4.51.

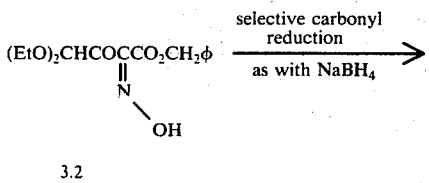

3.2

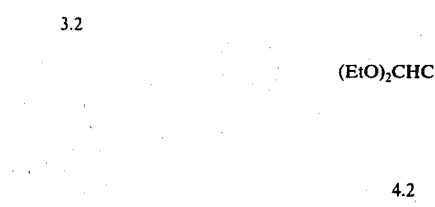

4.2

A solution of the keto-oxime [3.2] (288 g., 0.94 moles) in 1 liter of tetrahydrofuran was cooled to 0° C. and treated portionwise with sodium borohydride (17.8 g., 0.47 moles). After stirring for three-fourths hours at 0° C., it was allowed to come to room temperature over 1 ½ hours.

It was then recooled to 0° C., acidified carefully with dilute hydrochloric acid, and extracted with ether. The ether extract was washed with water and brine. It was dried over anhydrous sodium sulfate and evaporated to give 241.5 g. (83%) of the alcohol [4.2] which was used without purification.

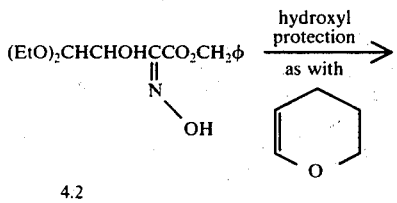

4.2

-continued

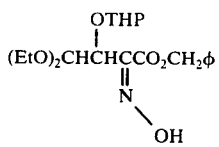

5.2

A solution of the alcohol [4.2] (241.5 g., 0.78 moles) in 1 liter of ether was treated with dihydropyran (130 g.; 1.5 moles) and then with 4.0 g. of p-toluene-sulfonic acid monohydrate. Some cooling was required to keep the initial reaction at gentle reflux. When the initial reaction had ceased, it was stirred at room temperature for 2 hours.

It was then poured onto 500 ml. of saturated sodium bicarbonate solution and the ether extract was washed with water and brine. It was dried over anhydrous sodium sulfate and evaporated to give 356 g. of the THP protected alcohol [5.2][1]. It was used as such in the following reaction.

1. The crude mixture contains [5.2] as well as some di-THP compound [6.2].

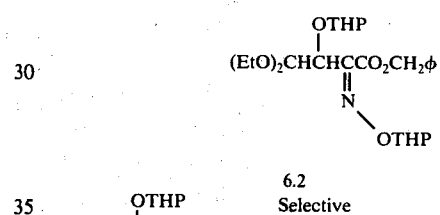

6.2

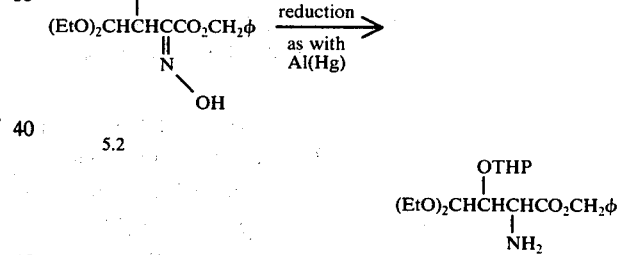

7.2

A solution of the oxime [5.2] (64 g.; 0.143 moles) in tetrahydrofuran (200 ml.) was added to a slurry of aluminum amalgam (prepared from 0.72 moles of aluminum foil according to the method of Vogel, "Practical Organic Chemistry", p. 193–98) at such a rate as to maintain a vigorous reaction. After stirring for 3–4 hours, a fresh amount of aluminum amalgam (0.36 moles) was added at such a rate as to maintain a vigorous reaction. After stirring for 16 hours, it was filtered through celite washing well with ether.

The filtrate was evaporated and the residue was dissolved in ether and treated with a solution of oxalic acid (12.9 g., 0.143 moles) in ether. The mixture was then extracted with cold water twice and the combined aqueous extracts were acidified with concentrated ammonium hydroxide in the cold. It was then extracted with ether and the extract dried over anhydrous sodium sulfate. Evaporation gave 22.8 g. (42% of the amine [7.2]

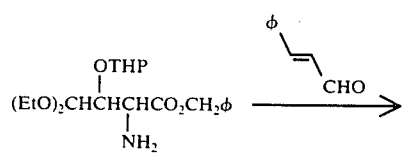

7.2

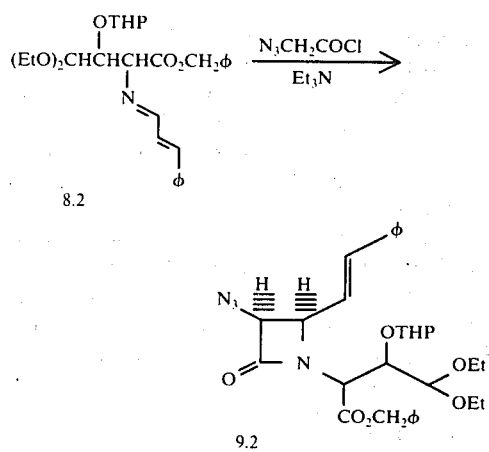

8.2

9.2

The amine [7.2] (28.9 g.; 0.076 moles) was treated with trans-cinnamaldehyde (10.0 g.; 0.076 moles) in methylene chloride (200 ml.) and refluxed for 2 hours. It was then dried over anhydrous sodium sulfate for several minutes and evaporated. The residue was dissolved in a further 200 ml. of methylene chloride and then evaporated again. This procedure was repeated twice more giving a residue with NMR showing almost complete Schiff base [8.2] formation.

The Schiff base [8.2] was immediately dissolved in methylene chloride (200 ml.) (dried over molecular sieves) and cooled to 0° C. It was treated with triethylamine (dried over potassium hydroxide pellets) (7.7 g.; 0.076 moles) and then dropwise at 0° to 5° C. with a solution of azidoacetyl chloride (9.1 g.; 0.076 moles) in dry methylene chloride (100 ml.) under an atmosphere of dry nitrogen. When the addition was complete, it was allowed to come to room temperature for 16 hours and then refluxed for three-fourths hour.

On cooling, the solution was washed with water, 1% hydrochloric acid, and brine. It was dried over anhydrous sodium sulfate and evaporated to give 43.0 g. (100%) of crude styryl compound [9.2].

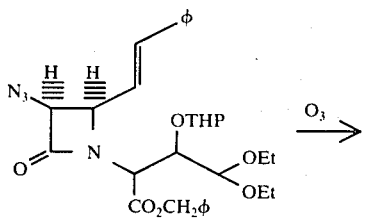

9.2

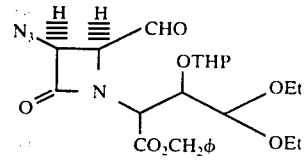

10.2

The crude styryl compound [9.2] (14.4 g.; 0.025 moles) was dissolved in methylene chloride (80 ml.) and cooled to −60° C. in a dry ice: isopropanol bath. Ozone was then bubbled through the solution until the appearance of a faint blue color persisted. It was then flushed with oxygen to remove excess ozone and treated with methyl sulfide (10 ml.) to decompose the ozonide. It was allowed to come to room temperature over 4 hours and then washed with water, 5% sodium bicarbonate, water, and brine. It was dried over anhydrous sodium sulfate and evaporated. The residue was evaporated under high vacuum at 40°-50° C. for 18 hours to remove most of the benzaldehyde. The residue (12.1 g.) had NMR showing about 50-60% of free aldehyde [10.2] by integration. It was used as such in the next step.

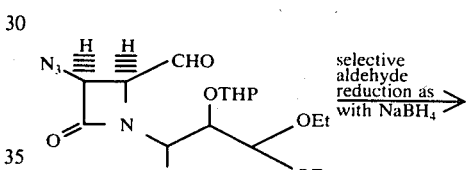

10.2

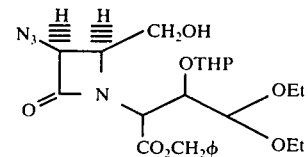

11.2

The crude aldehyde [10.2] (12.1 g.; 0.024 moles) was dissolved in tetrahydrofuran (100 ml.) and cooled to 0° C. It was treated portionwise with powdered sodium borohydride (0.46 g.; 0.012 moles) over a short period of time. After one-half hour stirring at 0° C., it was poured onto ice-cold 10% acetic acid and the acidified mixture was extracted with ether.

The ether extract was washed with water (twice), 10% sodium bicarbonate, and brine. It was dried over anhydrous sodium sulfate and evaporated to give 10.9 g. of crude alcohol [11.2].

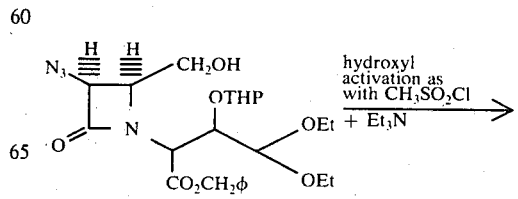

11.2

-continued

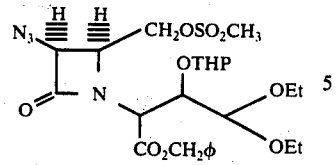
12.2

The crude alcohol [11.2] (12.8 g.) was dissolved in methylene chloride (100 ml.) dried over molecular sieves) and cooled to 0° C. It was treated with dry triethylamine )2.23 g.; 0.022 moles) and then dropwise with a solution of methanesulfonyl chloride (2.52 g.; 0.022 moles) in dry methylene chloride (30 ml.).

It was allowed to come to room temperature over 3 hours and then washed with water, 1% hydrochloric acid, and brine. It was dried over anhydrous sodium sulfate and evaporated to give 11.8 g. of crude mesylated alcohol [12.2].

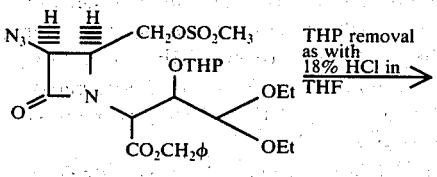
12.2

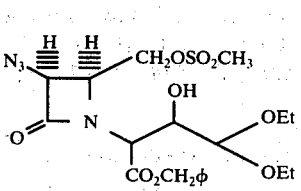
13.2

The crude THP-protected alcohol [12.2] (11.8 g.) was dissolved in tetrahydrofuran (100 ml.) and treated with cooling (keeping the temperature below 15° C.) with 18% hydrochloric acid (50 ml.). After stirring for an additional hour in the cold, thin layer chromatography showed loss of the starting material.

It was diluted with water and extracted with ether. The ether extract was washed with water and brine. It was dried over anhydrous sodium sulfate and evaporated.

The crude residue was purified by dry-column chromatography on silica gel (Activity III) using ether as the solvent. This gave 3.5 g. of the acetal [13.2]. The yield is 28% overall from the amine [7.2].

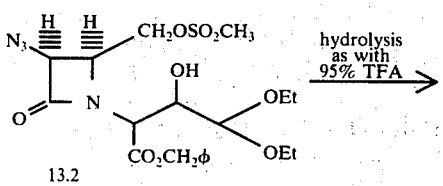
13.2

-continued

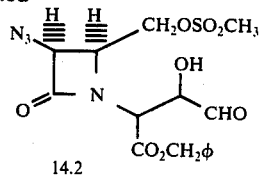
14.2

The acetal[13.2] (1.5 g.; 3 mmoles) was stirred for 45 minutes with 5 ml. of 95% trifluoroacetic acid and then treated with methylene chloride and water. The methylene chloride extract was washed with water, 10% sodium bicarbonate, and brine. It was dried over anhydrous sodium sulfate and evaporated to give 1.0 g. (78%) of crude hydroxy aldehyde [14.2].

3. Preparation of intermediates of formula

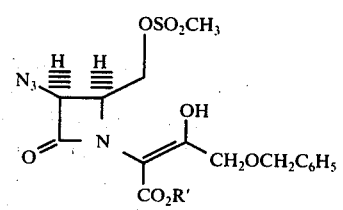

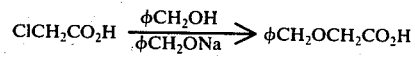

1.3         2.3

Benzyl alcohol (6500 ml.) is added to a 12 liter 3-necked flask equipped with an efficient stirrer, condenser and a heating mantle. The alcohol is heated above the melting point of sodium (~100°-110° C.) and sodium metal (600 g., 26 moles) is added in small pieces with vigorous stirring at a rate sufficient to maintain a gentle reflux and to prevent the accumulation of large amounts of sodium in the reaction flask (~3-4 hours). The solution is then cooled to about 80° C. and chloroacetic acid [1.3] (1120 g.; 12 moles) dissolved in the minimum amount of benzyl alcohol is added dropwise fairly rapidly. The mixture is heated under reflux for 4 hours, cooled to room temperature and diluted with 10 liters of ether. The precipitated sodium salt of benzyloxyacetic acid is collected by filtration, washed with ether, dissolved in cold water and acidified to pH 3 with concentrated HCl. Extraction with $CH_2Cl_2$, drying and concentration gives 1952 g. (98% yield) of benzyloxyacetic acid [2.3] as a crude oil which is esterified without further purification. If desired, the acid can be purified by distillation: b.p. 130°-132° C./0.1 mm.

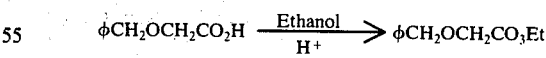

2.3         3.3

Ethanol (7 liters) in a 12 liter 1-neck flask equipped with condenser and drying tube is saturated with dry HCl. Benzyloxyacetic acid [2.3] (1952 g., 11.8 mole) is added in one portion and the solution is heated under reflux for 5 hours. Most of the ethanol is removed by distillation at normal pressure. The residue is cooled to about 5° C. and diluted with about 4 l. of cold water. Extraction with ether, washing of the ether with cold water, saturated $NaHCO_3$ solution and again with cold water, drying over $Na_2SO_4$ and concentration yields an oil which is purified by distillation to give 1425 g. (62% yield) of [3.3]; b.p. 138°–140° C./8 mm. The NMR spectrum indicated a benzyl —$CH_2$: singlet at 4.57δ, aromatic H at 7.3δ, O—$CH_2$—CO— at 4.07δ and an ethyl quartet and triplet centered at 4.18 and 1.25δ.

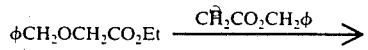

3.3

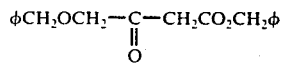

4.3

All operations are carried out under an atmosphere of dried $N_2$. A reaction flask (12 l. 3-neck flask with stirrer, $N_2$ inlet, 500 ml. addition funnel and cold temperature thermometer) is charged with 3 l. of dried tetrahydrofuran and cooled to −78° C. in a bath of dry ice-acetone. Three bottles of BuLi (2.4M in hexane, 1 mole/bottle) are added via a flexible adaptor under $N_2$. N,N-isopropyl cyclohexylamine (423.8 g., 3 mole) is added via the addition funnel over a period of about 15 minutes and stirring is continued for 15 minutes. Benzyl acetate (450.5 g., 3 mole) is then added dropwise over a 30 minute period and the solution is stirred for 30 minutes. Ethyl benzyloxyacetate [3.3] (555.0 g., 2.85 mole) is added dropwise over about 30 minutes and the cooling bath is removed at the end of the addition. The reaction mixture is stirred and allowed to come to room temperature in about 2 hours. When the internal temperature reaches 0°–5°, a voluminous solid separates. Anhydrous ether (about 3 l.) is then added to complete the precipitation. The solid is collected by filtration and washed with ether on the filter.

The solid is added to a vigorously stirred mixture of 250 ml. of concentrated HCl, 500 ml. of water, 500 ml. of ice and 3 l. of ether. When solution is complete the phases are decanted and the aqueous phase is extracted once more with ether. The combined ether layers are washed with brine, dried over $Na_2SO_4$ and concentrated to leave 659 g. (78%) of oily benzyl γ-benzyloxyacetoacetate. [4.3]: TLC: (silica gel, ether-pet. ether 2:1): 1 spot, Rf. 0.5, NMR indicates (aromatic H at 7.23δ; benzyl ester $CH_2$, singlet at 5.05δ; benzyl ether $CH_2$, singlet at 4.42δ; O—$CH_2$CO, singlet at 4.0δ; and $COCH_2CO_2$, singlet at 3.48δ.

This oil is used without purification in the next step. Distillation of large amounts proceeds with extensive decomposition but a small amount (5 ml.) can be purified by distillation if necessary: b.p. 180°–182°/0.05. The TLC and NMR of the crude product and of a distilled sample are identical. New spots appear on TLC if the oil is stored for some time.

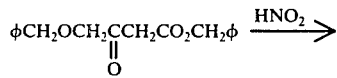

4.3

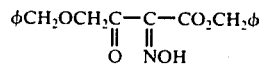

5.3

A solution of sodium nitrite (165 g., 2.4 mole) in 660 ml. of water is added to the cooled (∼10° C.) solution of benzyl γ-benzyloxyacetate from the step immediately above in 1100 ml. of acetic acid. The rate of addition is regulated so that the temperature of the reaction mixture does not exceed 25° C. A white solid crystallizes out when about one-half of the nitrite solution is added. After the end of the addition the mixture is stirred for an additional 30 minutes at 10° and diluted slowly with 2 l. of water. The solid oxime is collected by filtration washed with cold water until the washings are neutral, and dried in vacuo (16 hours) to give 856 g. of oxime as a white solid. The oxime is dissolved in methylene chloride, the water removed by decantation, the organic phase washed with brine, dried over $Na_2SO_4$ and concentrated until crystals start appearing. Crystallization is completed by dilution with petroleum ether (30° – 60°). Filtration, washing with petroleum ether and drying affords 585 g. (81%) of oxime [5.3]; m.p. 92°–95°, NMR indicates aromatic H at 7.27 and 7.30δ; benzyl ester $CH_2$ at 5.27δ and ether $CH_2$ at 4.5δ. This material is used in the next step.

An analytical sample prepared in benzene-petroleum ether had the following properties: m.p. 96°–97°.

Calc'd for $C_{17}H_{18}NO_5$: C, 66.05; H, 5.23; N, 4.28. Found: C, 66.06; H, 5.25; N, 4.23.

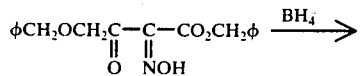

5.3

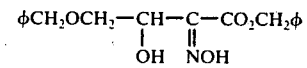

6.3

The keto-oxime [5.3] (400 g., 1.22 mole) dissolved in 1000 ml. dioxane is cooled to 5°, stirred vigorously and treated portionwise with finely powdered sodium borohydride (23.4 g., 0.62 mole) over a 30 minute period. The temperature remains at 10° for a while and then a vigorous reaction sets in which must be controlled with an ice-salt bath (temperature goes up to 50°-60°). After 1 hour TLC (silica gel, ether-petroleum ether) shows disappearance of the starting material. The mixture is stirred an additional hour, poured into ice-cold dilute hydrochloric acid and extracted with ether (2 × 1 l.). The combined extracts are washed with water (5 × 1 l.) and with brine. Drying and concentration leaves a tan-colored solid which is recrystallized in benzene-petroleum ether to give 308 g. (77% yield) of the alcohol-oxime [6.3] as a white solid, m.p. 83°–85°. NMR indicates aromatic H at 7.23δ, ester $CH_2$ at 5.18δ, benzyl ether at 4.48δ, (triplet); H of CHOH at 4.67δ, $CH_2$ ether at 3.65δ and exchangeable H at 3.42 and 10.05δ.

Calc'd for $C_{12}H_{19}NO_5$: C, 65.64; H, 5.81; N, 4.25. Found: C, 65.62; H, 5.91; N, 4.26.

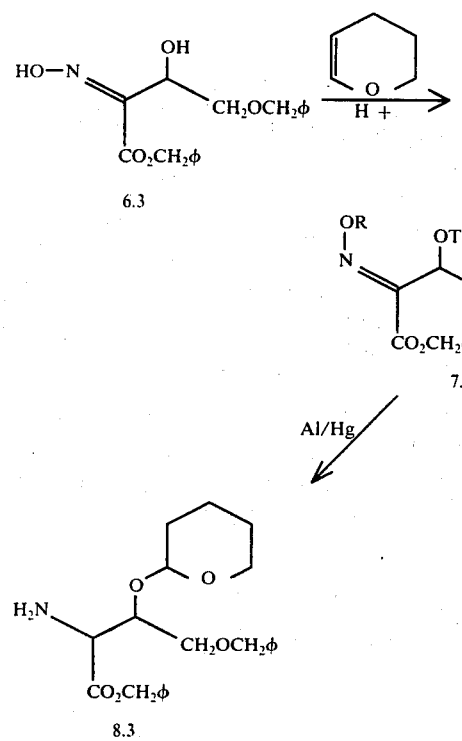

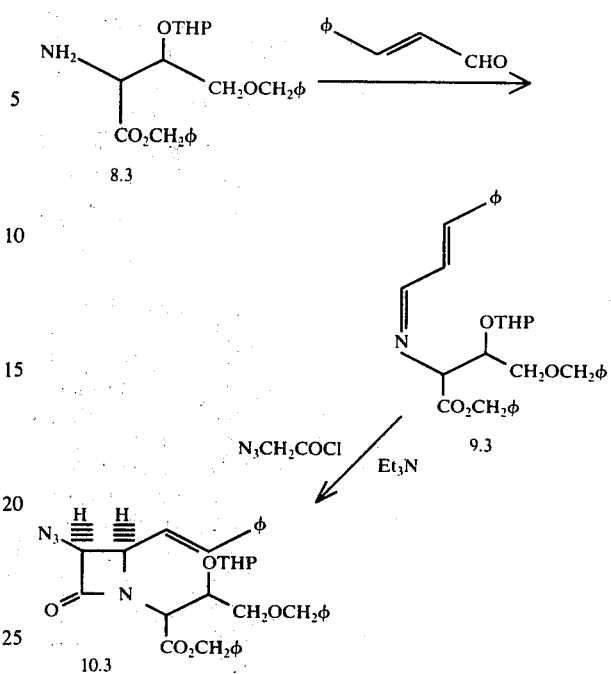

To a well-stirred suspension of hydroxy-oxime [6.3] (298 g., 0.91 mole) in dihydropyran (650 ml., 7.1 mole) are added 15 to 20 drops of concentrated HCl and the mixture is stirred at room temperature. After ½ hour a clear solution is obtained and after 4 hours TLC indicates disappearance of the starting hydroxy-oxime. The solution is diluted with technical ether (1.5 l.) and poured into a 10% $NaHCO_3$ solution. The ether phase is washed with brine, dried and concentrated to leave 402 g. of a yellow oil which consists of a mixture of mono and bis-tetrahydropyranyl derivatives.

The above oil (394 g.) dissolved in ether (technical 600 ml.) is added dropwise to freshly prepared aluminum amalgam covered with technical ether (about 1000 ml.) (the amalgam is prepared using 120 g. aluminum foil as described in Vogel, Practical Organic Chemistry) at a rate sufficient to maintain a vigorous reflux. The mixture is stirred 2 hours after the end of the addition. After removal of the insoluble materials by filtration over Celite, the filtrates are dried over $Na_2SO_4$ and treated with anhydrous oxalic acid (72 g., 0.8 mole) dissolved in the minimum volume of ethanol. After two hours at 0°–5° the solid oxalate salt is collected by filtration, washed with ether and dried to give 215 g. of white solid, m.p. 115°–119°. This crude oxalate is used for regeneration of the free base.

An analytical sample of the oxalate, prepared in methanol-ether gives: m.p. 136°–137°.

Calc'd for $C_{23}H_{29}NO_5 \cdot C_2H_2O_4$: C, 61.34; H, 6.38; N, 2.86. Found: C, 61.25; H, 6.50; N, 2.76.

The free base [8.3] is regenerated by adding the solid oxalate to a well stirred mixture of an excess of ice-cold concentrated ammonium hydroxide and ether: 152 g. (42%), yellowish heavy oil. NMR indicates aromatics at 7.30δ, benzyl ester $CH_2$ at 5.1δ, benzyl ether $CH_2$ at 4.47δ and $NH_2$ at 1.82δ.

A mixture of the amine [8.3] (117.2 g.; 0.294 mole) and cinnamaldehyde (38.8 g.; 0.294 mole) in 500 ml. of reagent grade $CH_2Cl_2$ was refluxed for one hour. The solvent was removed on the rotary evaporator and the residue redissolved in 500 ml. of fresh $CH_2Cl_2$. Part of the solvent was distilled at atmospheric pressure (350 ml.) and the remainder was taken to dryness on the rotary evaporator to give an oil consisting of crude [9.3].

The above oil was dissolved in 400 ml. of $CH_2Cl_2$, triethylamine (45 ml., 0.32 mole) was added and the solution was cooled to 0° C. A solution of azidoacetyl chloride (38.4 g.; 0.32 mole) in 200 ml. of methylene chloride was added to the above cooled and stirred solution in 1.5 hour. The mixture was allowed to come slowly to room temperature and was stirred for 16 hours. It was then heated under reflux for 1 hour, cooled, washed with ice-cold saturated sodium bicarbonate solution and with ice-cold brine solution, dried over $Na_2SO_4$ and concentrated on the rotary evaporator to leave 171.2 g. (98%) of an oil whose IR and NMR spectra are consistent with structure [10.3].

If needed, purification can be effected through chromatography over a column of silica gel. The crude product is normally used in the next step.

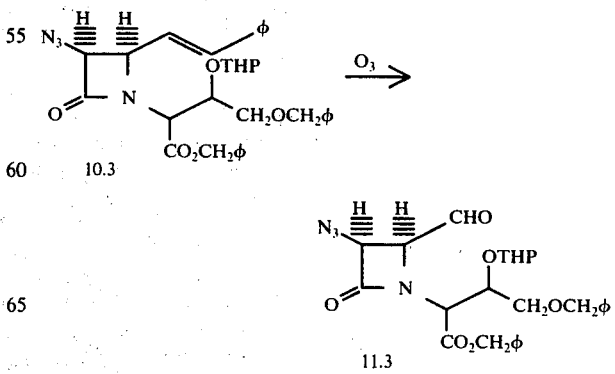

A solution of the crude styryl compound [10.3] (117.6 g., 0.198 mole) in 600 ml. of CH$_2$Cl$_2$ was cooled to −60° C. and ozonized until a faint blue color appeared. Dimethyl sulfide (75 ml.) was added and the solution was allowed to come slowly to room temperature. After 18 hours, the solution was washed several times with ice-cold water, dried over Na$_2$SO$_4$ and concentrated on the rotary evaporator to leave 104 g. of an oil. The pure aldehyde [11.3] (34.6 g.) was obtained in 32% yield after chromatography on 1200 g. of activity 2 silica gel using the dry column technique and eluting with ether-petroleum ether.

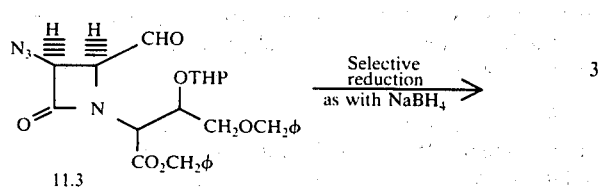

The pure aldehyde [11.3] (35.5 g., 0.068 mole) was dissolved in 250 ml. of reagent grade THF, cooled to −5° C., and treated portionwise under good stirring with sodium borohydride (1.29 g., 0.034 mole). After one-half hour, the mixture was acidified with ice-cold 10% acetic acid and was extracted with ether. The combined ether extracts were washed with ice-cold water and ice-cold 1% NaHCO$_3$ solution, dried and concentrated to leave 33.4 g. (94%) of crude alcohol as an oil whose NMR spectrum is consistent with structure [12.3].

The alcohol was purified by column chromatography over silica gel.

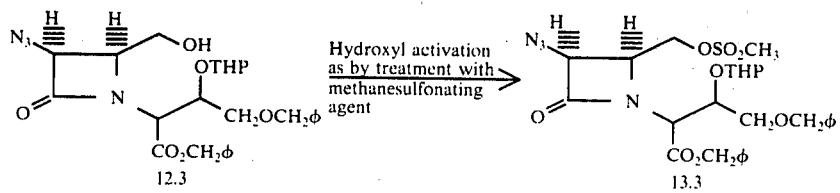

The purified alcohol [12.3] (15 g., 0.0286 mole) was dissolved in 100 ml. of CH$_2$Cl$_2$, cooled to 0° C., treated with triethylamine (4.2 ml., 0.03 mole), and treated dropwise with methanesulfonyl chloride (3.44 g., 0.03 mole) dissolved in 50 ml. of CH$_2$Cl$_2$. After 2 hours, the mixture was washed with ice-cold water and ice-cold brine solution, dried and concentrated on the rotary evaporator to give 15.7 g. (92%) of a thick syrup whose NMR spectrum is consistent with structure [13.3].

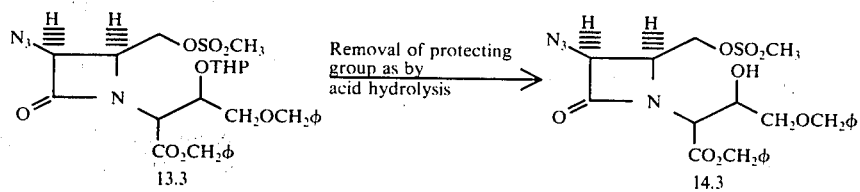

The mesylate [13.3] (15.5 g., 0.0257 mole) was dissolved in 100ml. of THF and treated with 50 ml. of 10% hydrochloric acid. After a 4 hour stirring period, the solution was extracted with ether and the combined ether extracts were washed with water and brine solution, dried and concentrated on the rotary evaporator to leave 13.5 g. of an oil whose NMR spectrum is consistent with structure [14.3].

If desired, the alcohol [14.3] can be purified by column chromatography.

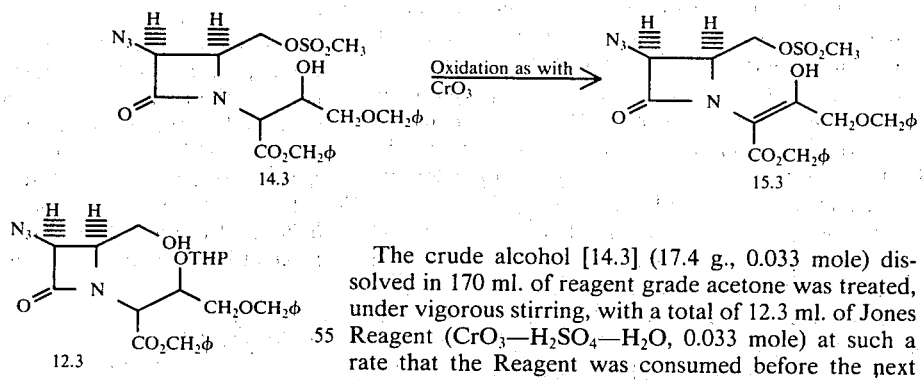

The crude alcohol [14.3] (17.4 g., 0.033 mole) dissolved in 170 ml. of reagent grade acetone was treated, under vigorous stirring, with a total of 12.3 ml. of Jones Reagent (CrO$_3$—H$_2$SO$_4$—H$_2$O, 0.033 mole) at such a rate that the Reagent was consumed before the next drop was added (orange to green). The mixture was diluted with water and extracted with ether. The combined ether layers were extracted with 140 ml. of ice-cold 1% NaOH solution, the basic extracts acidified immediately with ice-cold 10% hydrochloric acid and extracted with ether. Concentration of the neutral ether extracts gave 10.8 g. of an oil consisting mainly in unreacted [14.3]. These were reoxidized as above. The combined ether extracts containing the acidic compound were dried and concentrated to give a total of 4.6 g. of crude enol [15.3] as an oil whose IR and NMR are consistent with structure [15.3].

EXAMPLE 1

Benzyl 7β-Azido-3-acetoxymethyl-Δ³-0-2-isocephem-4-carboxylate (from dibromide intermediate)

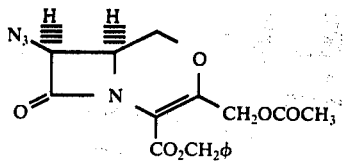

The mixture of dibromide starting materials [12.1 and 13.1] (1.7 g.; 3 mmole) in 50 ml. of dimethylformamide (DMF) was stirred with potassium acetate[1] (1.2 g.; 3.5 equiv.) for 16 hours at room temperature. The mixture was then diluted with 100 ml. of diethylether and 100 ml. of 10% hydrochloric acid. The ether layer was washed with 10% sodium bicarbonate solution (once; 50 ml.) and with brine (once; 75 ml.). The extract was then dried and evaporated in vacuo to leave 1.0 g. of a dark brown residue. This product was purified by passing through a short column of activity III silica gel with methylene chloride elution. This gave a fraction containing 700 mg. (63% yield) of a colorless oil whose spectral data confirm that it has the structure of the title product.

Crystallization from 2:1 benzene:petroleum ether gave a white solid; m.p. 94°–97° C.

Anal. Calc'd for $C_{17}H_{16}N_4O_6$: C, 54.84; H, 4.33; N, 15.05. Found: C, 55.19; H, 4.47; N, 14.89.

1. The potassium acetate used was analytical grade which had been finely ground before use. Water was probably absorbed by the acetate during this process.

EXAMPLE 2

Benzyl 7β-Azido-3-acetoxymethyl-Δ³-0-2-isocephem-4-carboxylate (from diiodide intermediate)

Diiodide intermediate [23.1] (600 mg., 0.93 mmole) prepared according to the method described above was added to a solution of potassium acetate (380 mg., 3.9 mmole) in 5 ml. of dimethylformamide and stirred at 24° C. for 20 hours. The solution was mixed with ether (25 ml.) and washed with water (5 × 25 ml.). The ether mixture was dried (sodium sulfate) and evaporated in vacuo to give crude benzyl 7β-azido-3-acetoxymethyl-Δ³-0-2-isocephem-4-carboxylate. NMR indicated approximately 35% yield. NMR and TLC established that the product is identical with that produced in Example 1.

EXAMPLE 3

Benzyl 7β-Azido-3-formyloxymethyl-Δ³-0-2-isocephem-4-carboxylate

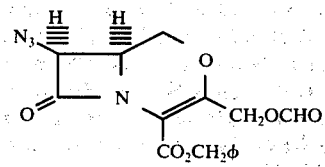

Sodium formate (2.86 g., 42 mmole) was added to a solution of the dibromide mixture [12.1 and 13.1] (2.86 g., 5.05 mmole) in DMF (100 ml.) containing water (0.1 ml.). The solution was stirred at room temperature for 72 hours, diluted with water (100 ml.) and extracted in ether (5 × 75 ml.). The combined organic phases were washed with brine, dried ($Na_2SO_4$) and concentrated to leave 2.52 g. of an oil. The oil was purified by column chromatography on silica gel (100 g.) eluting with 3:1 ether: petroleum ether. The main fraction contained 0.70 g. of pure benzyl 7β-azido-3-formyloxymethyl-Δ³-0-2-isocephem-4-carboxylate as a colorless oil. The NMR spectrum of the product was in agreement with the structure of the title product.

EXAMPLE 4

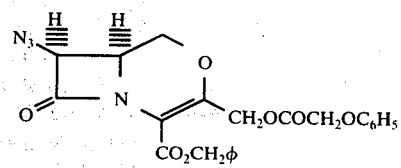

Dibromide mixture [12.1 and 13.1] (9.5 g., 17.2 mmole) was dissolved in 100 ml. of DMF and treated with potassium phenoxyacetate (8.2 g., 43.0 mmole). The reaction mixture was stirred at 50–60° C. for 18 hours. On cooling, it was poured onto 500 ml. of water and extracted with dichloromethane. The extracts were washed several times with water and finally with brine. Drying over anhydrous sodium sulfate and evaporation gave crude product which was purified by "dry-column" chromatography on Activity III silica gel eluting with ether. The product was obtained as a middle cut (3.1 g., 38% yield) which was about 60% pure by NMR.

EXAMPLE 5

Benzyl 7β-Azido-3-hydroxymethyl-Δ³-0-2-isocephem4-carboxylate

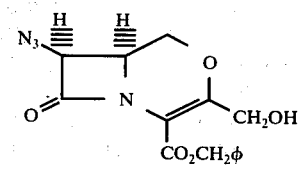

The crude hydroxy aldehyde starting material [14.2] (50 g., 0.117 mmole) prepared above and powdered potassium acetate (50 g., 0.51 mmole) were stirred in 350 ml. of dimethylformamide for 18 hours. The mixture was then diluted with water and extracted with methylene chloride. The extract was washed with water several times and dried over anhydrous sodium sulfate.

Evaporation gave 40 g. of a residue which was purified by dry-column chromatography on silica gel (Activity III) using ether as the solvent. This gave 7.0 g. (19% yield) of pure title product as a pale-yellow solid.

This compound was found to be identical (IR, NMR, mixed m.p.), to the compound prepared in Example 8.

For analysis, a sample was crystallized from ethyl acetate/petroleum ether (30–60°) giving white crystals with m.p. 88–90° C.

Anal. Calc'd. for $C_{15}H_{14}N_4O_5$: C, 54.54, H, 4.27; N, 16.96. Found: C, 54.49; H, 4.23; N, 16.97.

EXAMPLE 6

Benzyl 7β-Azido-3-benzyloxymethyl-Δ³-0-2-isocephem-4-carboxylate

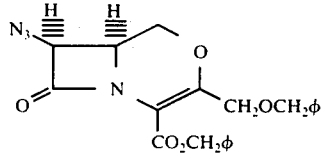

The crude enol starting material [15.3] (4.6 g., 0.089 mmole) was dissolved in 75 ml. of CH₂Cl₂, treated with triethylamine (1.55 ml., 0.11 mole) and heated under reflux for 3 hours. After cooling, the mixture was washed with 10% hydrochloric acid, water, 3% NaHCO₃ solution and brine solution. Drying (Na₂SO₄) and concentration left 3.56 g. of crude material which was purified by chromatography over silica gel to give 1.05 g. (28% yield) of pure benzyl 7β-azido-3-benzyloxymethyl-Δ³-0-O-2-isocephem-4-carboxylate. IR and NMR of this compound were in agreement with the structure of the title product.

EXAMPLE 7

Benzyl 7β-Azido-3-acetoxymethyl-Δ³-0-2-isocephem-4carboxylate (acetylation of benzyl 7β-azido-3-hydroxymethyl-Δ³-0-2-isocephem-4-carboxylate Benzyl 7β-Azido-3-hydroxymethyl-Δ³-0-2-isocephem4-carboxylate (0.2 g., 0.6 mmole) was treated with 8 ml. of pyridine and then acetic anhydride (0.2 g., 2.0 mmole). After stirring at room temperature for 3 hours, the reaction mixture was diluted with water and extracted with ether. The extract was washed with cold 5% hydrochloric acid, water, 1% sodium bicarbonate, and brine. It was then dried over anhydrous sodium sulfate and evaporated to give 0.18 g. (83% yield) of the acetylated title product.

This compound was found to be identical (IR, NMR, mixed m.p.) to the compound prepared in Example 1.

EXAMPLE 8

Benzyl-7β-Azido-3-hydroxymethyl-Δ³-0-2-isocephem-4-carboxylate (acid hydrolysis method)

A. A solution of benzyl 7β-azido-3-formyloxymethyl-Δ³-0-2-isocephem-4-carboxylate (2.0 g.) in acetone (15 ml.), water (15 ml.) and concentrated hydrochloric acid (2.0 ml.) was stirred at room temperature for 2.5 hours. The solution was extracted with CH₂Cl₂ (3 × 25 ml.) and the combined organic extracts were washed with brine, dried (Na₂SO₄) and concentrated to give 1.77 g. of an oil which was purified by column chromatography on silica gel (80 g.) to give 1.0 g. (52% yield) of pure title product identical (IR, NMR, m.p.) with a sample prepared in Example 3 by cyclization.

B. The procedure of Part A was repeated except that the starting material was benzl 7β-azido-3-acetoxymethyl-Δ³-0-2-isocephem-4-carboxylate and the reaction time was 48 hours. The title product was produced in 20% yield.

EXAMPLE 9 p-Nitrobenzyl-7β-Azido-3-methylsulfonyloxymethyl-Δ³-0-2-isocephem-4-carboxylate

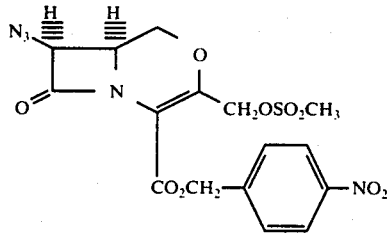

A solution of methanesulfonyl chloride (0.50 ml., 6.5 mmole) in 10 ml. of methylene chloride was added dropwise with stirring to a solution of p-nitrobenzyl 7β-azido-3-hydroxymethyl-Δ³-0-2-isocephem-4-carboxylate (2.41 g., 6.43 mmole), triethylamine (0.97 ml., 7.0 mmole) and 75 ml. of methylene chloride at −10°. After one-half hour at −10° and 1 hour at 24°, the solution was washed with 5% hydrochloric acid, 2% sodium bicarbonate, and water (85 ml. each), then the solvent was evaporated in vacuo to give the mesylate title product, 2.86 g. (98% yield), as a yellow foam. The NMR of the product was in agreement with the proposed structure.

The p-nitrobenzyl 7β-azido-3-hydroxymethyl-Δ³-0-2-isocephem-4-carboxylate starting material used above may be prepared as follows:

1. The diiodide intermediate of the formula

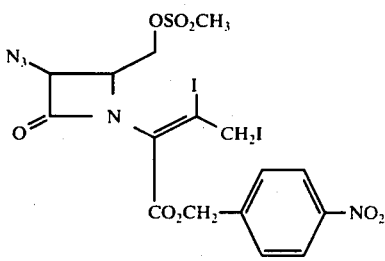

was prepared from p-nitrobenzyl acetoacetate according to the procedures of Preparations 1 and 1A (Starting Materials) described above.

2. The diiodide intermediate (6.6 g., 9.6 mmole) was cyclized with potassium formate (2.54 g., 30 mmole) in a solution of 100 ml. DMF and 0.1 ml. water at 0°. After stirring for 5 hours with the cooling bath removed, the mixture was poured into 100 ml. of cold water and extracted with methylene chloride. After washing with water containing a little NaCl, drying and evaporation in vacuo, p-nitrobenzyl 7β-azido-3-formyloxymethyl-Δ³-0-2-isocephem-4-carboxylate was recovered (5.3 g.) as a brown oil.

3. To a solution of 5.3 g. of the 3-formyloxymethyl intermediate in 53 ml. of acetone was added 26 ml. of water and 3.2 ml. of 12M HCl. The mixture was stirred at 24° for 7 hours, then poured into 100 ml. water and extracted with methylene chloride. The combined extracts were washed with water containing a little sodium chloride, dried and evaporated in vacuo to give 3.6 g. of a brown oil. The oil was absorbed from methylene chloride onto 18 g. of silica gel and placed on a 72 g. silica gel column (grade 3, 5% ether). The column was eluted with 200 ml. of ether, then with ether/ethyl acetate 3:1. The major component (Rf 0.20) gave, on evaporation of the solvent in vacuo, a yellow solid which was recrystallized from acetone-ether to give the 3-hydroxymethyl starting material of this example, 950 mg. (17.5% yield from the diiodide). m.p. 147°–148°.

Anal. Calc'd. for $C_{15}H_{13}N_5O_7$: C, 48.00; H, 3.49; N, 18.66. Found: C, 48.11; H, 3.61; N, 18.81.

EXAMPLE 10

Conversion of p-Nitrobenzyl 7β-Azido-3-hydroxymethyl-Δ³-0-2-isocephem-4-carboxylate to lactone

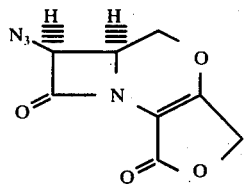

An aqueous solution of 0.05N sodium carbonate (20 ml., 1.0 mmole) was added dropwise with stirring to a solution of p-nitrobenzyl 7β-azido-3-hydroxymethyl-Δ³-0-2-isocephem-4-carboxylate (as prepared in Example 9) (0.38 g., 1.0 mmole) in 50 ml. tetrahydrofuran. The addition took 15 minutes and the solution was stirred for an additional 5 minutes, then diluted with 20 ml. brine and 20 ml. ether. The phases were separated and the organic phase was washed with water and brine, dried ($Na_2SO_4$) and evaporated in vacuo to give 0.28 g. of a solid which was chromatographed (dry-column method) on 15 g. silica gel (activity III) eluting with ether:ethyl acetate 3:1. The lactone (0.16 g., 72%) was obtained as a white crystalline solid. M.p. 178°–179° d (ethyl acetate-ether).

Anal, Calc'd. for $C_8H_6N_4O_4$: C, 43.25; H, 2.72; N, 25.22. Found: C, 43.10; H, 2.75; N, 25.45.

EXAMPLE 11 p-Nitrobenzyl 7β-Azido-3-carbamoyloxymethyl-Δ³-0-2isocephem-4-carboxylate

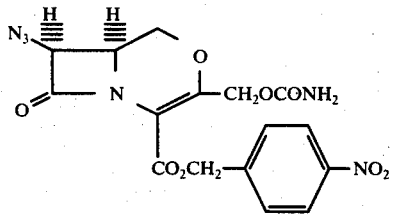

p-Nitrobenzyl 7β-Azido-3-hydroxymethyl-Δ³-0-2-isocephem-4-carboxylate (375 mg., 1.0 mmoles) was dissolved in 15 ml. of benzene and treated with sodium cyanate (130 mg., 2.0 mmoles) followed by trifluoroacetic acid (0.16 ml., 2.1 mmoles). After stirring for 2 hours, the reaction mixture was treated with 25 ml. of water and 15 ml. of ethyl acetate. The aqueous layer was extracted once with 15 ml. of ethyl acetate and the combined organic extracts were washed with water and brine. Drying was over anhydrous sodium sulfate and evaporation in vacuo gave 400 mg. (96%) of crude carbamate product which showed only a minor impurity by thin-layer chromatography (silica gel, 10% ethyl aetate in ether).

EXAMPLE 12

Benzyl 7β-azido-3-bromomethyl-Δ³-0-2-isocephem-4-carboxylate

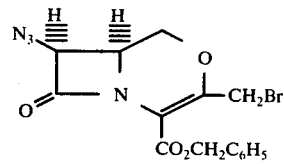

To a solution of benzyl 7β-azido-3-hydroxymethyl-Δ³-0-2-isocephem-4-carboxylate in benzene is added about an equimolar amount of pyridine and a slight molar excess of phosphorus tribromide. There is produced the 3-bromomethyl title product.

EXAMPLE 13 p-Nitrobenzyl 7β-Azido-3-(1-methyltetrazol-5yloxymethyl)-Δ³-0-2-isocephem-4-carboxylate

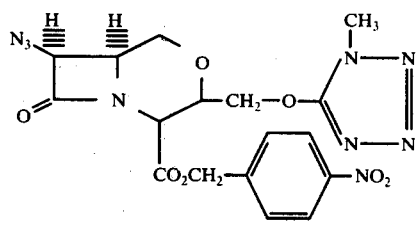

p-Nitrobenzyl 7β-azido-3-hydroxymethyl-Δ³-0-2-isocephem-4-carboxylate (0.70 g., 1.86 mmole) was dissolved in methylene chloride (50 ml.) and triethylamine 0.24 ml., 1.86 mmole) was added. While stirring the solution, there was added dropwise (in 5 minutes) a solution of methanesulfonyl chloride (0.145 ml., 1.86 mmole) in methylene chloride (10 ml.). The resulting solution of p-nitrobenzyl 7β-azido-3-methylsulfonyloxymethyl-Δ³-0-2-isocephem-4-carboxylate was stirred at room temperature for 1 hour, (protected from moisture by a calcium chloride drying tube). At the end of this time, an additional quantity of triethylamine (0.24 ml., 1.86 mmole) was added followed by a solution of 1-methyltetrazol-5-ol (0.186 g., 1.86 mmole) in methylene chloride (25 ml.). The solution was stirred at room temperature for 5 days and then the methylene chloride was removed by evaporation in vacuo and replaced by chloroform (100 ml.). The solution was refluxed 20 hours, then cooled, washed successively with 10% HCl, water and brine, dried ($Na_2SO_4$) and evaporated to dryness leaving a dark semi-solid (0.80 g.). This was chromatographed (dry-column) on silica gel III (25 g.), eluting with ether:ethyl acetate 3:1. The pure compound was obtained as a white solid, m.p. 174°–176° d (ethyl acetate). NMR showed the compound to be the title product.

Anal. Calc'd. for $C_{17}H_{15}N_9O_7$: C, 44.64; H, 3.30; N, 27.56. Found: C, 44.87; H, 3.48; N, 27.59.

EXAMPLE 14

Benzyl 7β-Amino-3-acetoxymethyl-Δ³-0-2-isocephem-4-carboxylate

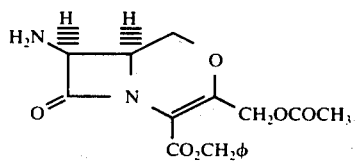

H$_2$S gas was slowly introduced into a stirring solution of benzyl 7β-azido-3-acetoxymethyl-Δ³-0-2-isocephem-4-carboxylate (793 mg., 2.1 mmole), triethylamine (210 mg., 2.1 mmole) and 15 ml. of methylene chloride for 10 minutes. The flask was then flushed with nitrogen to remove excess H$_2$S and then evaporated to dryness in vacuo. The residue was partitioned between diethylether and 10% hydrochloric acid three times. The combined acid extracts were backwashed twice with diethylether and then carefully alkalized with solid sodium bicarbonate, saturated with sodium chloride and extracted with methylene chloride (three times, 75 ml. portions). The combined extracts were washed with brine (once, 75 ml. portion), dried (anhydrous sodium sulfate) and evaporated in vacuo to give 415 mg. (60% yield) of title product as a colorless oil. Spectral data were consistent with the assigned structure.

Anal. Calc'd. for C$_{17}$H$_{18}$N$_2$O$_6$: C, 58.95, H, 5.24; N, 8.09. Found: C, 58.39; H, 5.32; N, 7.95.

EXAMPLE 15

Benzyl 7β-Amino-3-benzyloxymethyl-Δ³-0-2-isocephem-4-carboxylate

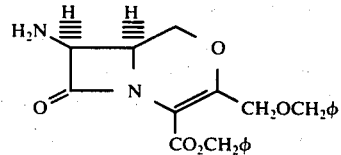

Benzyl 7β-azido-3-benzyloxymethyl-Δ³-0-2-isocephem-4-carboxylate (1.45 g., 3.5 mmole) was dissolved in 150 ml. of dry CH$_2$Cl$_2$ and cooled to 0° C. Triethylamine (1 ml., 7 mmole) was added and, while stirring and cooling, H$_2$S gas was passed through the solution until it was saturated. The solution was then allowed to come to room temperature in 2 hours and concentrated on the rotary evaporator. The residue was partitioned between 10% hydrochloric acid and ether. The mixture of solid and aqueous phase was separated and combined with the subsequent aqueous washings of the ether phase. The solids and combined aqueous phases were made basic with solid NaHCO$_3$ and extracted with CH$_2$Cl$_2$. The extracts were dried (Na$_2$SO$_4$) and concentrated to leave 0.80 g. of crude title product. The NMR of the sample was in agreement with the structure proposed.

EXAMPLE 16

Benzyl 7β-Amino-3-hydroxymethyl-Δ³-0-2-isocephem-4-carboxylate

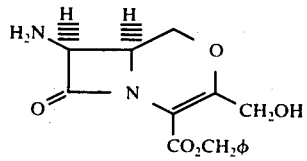

Benzyl 7β-azido-3-hydroxymethyl-Δ³-0-isocephem-4-carboxylate (1.0 g., 3 mmole) was dissolved in 60 ml. of dry CH$_2$Cl$_2$ and cooled to 0° C. Triethylamine (0.75 ml., 6 mmole) was added and, while stirring and cooling, H$_2$S gas was passed through the solution until it was saturated. The solution was stirred at room temperature for 30 minutes and concentrated. Fresh CH$_2$Cl$_2$ (∼30 ml.) was added and the solution was again concentrated. This operation was repeated a second time. The residue was a yellow oil consisting of crude title product.

EXAMPLE 17

7β-Amino-3-acetoxymethyl-Δ³-0-2-isocephem-4-carboxylic acid

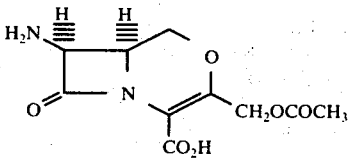

Benzyl 7β-azido-3-acetoxymethyl-Δ³-0-2-isocephem-4-carboxylate (5.0 g., 13.4 mmole) was dissolved in 300 ml. of absolute ethanol and treated with palladium chloride (1.2 g., 7.1 mmole). It was then hydrogenated on a Parr Hydrogenator for 1 hour at room temperature and an initial pressure of 50 p.s.i.g. It was then filtered, washing with warm ethanol (150 ml.). The filtrate was evaporated in vacuo to yield 4.2 g. of a residue in the form of a solidified foam. The NMR was consistent with the hydrochloride salt of the title product.

The free amino acid title product is obtained by dissolving the hydrochloride salt in the minimum amount of water and adjusting the pH to 3.5 with cold concentrated ammonium hydroxide. The product is collected by filtration and washed with cold water and acetone.

The amino acid title product has m.p. 275° (decomposition) and IR and NMR consistent with the desired structure.

A sample of the above compound (called BC-L66) was found to inhibit D. pneumoniae A9585 at a concentration of 8 mcg./ml., St. pyogenes A9604 at 8 mcg./ml. and S. aureus A9537 at 32 mcg./ml.

EXAMPLE 18 p-Nitrobenzyl 7β-amino-3-(1-methyltetrazol-5-yloxymethyl)-Δ³-0-2-isocephem-4-carboxylate p-Nitrobenzyl 7β-azido-3-(1-methyltetrazol-5-yloxymethyl)-Δ³-0-2-isocephem-4-carboxylate (0.26 g., 0.57 mmole) was dissolved in methylene chloride (50 ml.) and nitrogen was bubbled through the solution for 5 minutes. Triethylamine (0.145 ml., 1.14 mmole) was added and the solution was stirred while hydrogen sulfide was gently bubbled into it for about 1½ minutes. The resulting solution was stirred at room temperature for 1½ hours by which time there was no more gas evolution. The excess hydrogen sulfide was removed by a stream of nitrogen bubbled through the solution which was in turn extracted with 10% HCl (10 ml.) and water (2 × 10 ml.). The combined aqueous extracts were carefully alkalized with 5% sodium bicarbonate solution, and then extracted with methylene chloride (3 × 25 ml.). The organic extracts were washed with brine, dried ($Na_2SO_4$), and evaporated on the aspirator to give the title product as a white amorphous solid (0.15 g.).

EXAMPLE 19

Replacement of the benzyl 7β-azido-3-acetoxymethyl-Δ³-O-2-isocephem-4-carboxylate in the procedure of Example 14 with an equimolar weight of benzyl 7β-azido-3-formyloxymethyl-Δ³-O-2-isocephem-4-carboxylate, p-nitrobenzyl 7β-azido-3-methylsulfonyloxymethyl-Δ³-O-2-isocephem-4-carboxylate, p-nitrobenzyl 7β-azido-3-carbamoyloxymethyl-Δ³-O-2-isocephem-4-carboxylate and benzyl 7β-azido-3-bromomethyl-Δ³-O-2-isocephem-4-carboxylate produces the corresponding 7β-amino benzyl or p-nitrobenzyl esters of the above-mentioned compounds.

EXAMPLE 20

Replacement of the benzyl 7β-azido-3-acetoxymethyl-Δ³-O-2-isocephem-4-carboxylate in Example 17 with an equimolar weight of benzyl 7β-azido-3-hydroxymethyl-Δ³-O-2-isocephem-4-carboxylate, benzyl 7β-azido-3-formyloxymethyl-Δ³-O-2-isocephem-4-carboxylate, p-nitrobenzyl 7β-azido-3-methylsulfonyloxymethyl-Δ³-O-2-isocephem-4-carboxylate, p-nitrobenzyl 7β-azido-3-carbamoyloxymethyl-Δ³-O-2-isocephem-4-carboxylate, benzyl 7β-azido-3-bromomethyl-Δ³-O-2-isocephem-4-carboxylate or p-nitrobenzyl 7β-azido-3-(1-methyltetrazol-5-yloxymethyl)-Δ³-O-2-isocephem-4-carboxylate produces the corresponding 7β-amino 4-carboxylic acid compounds of the above-mentioned azido esters.

EXAMPLE 21

Pivaloyloxymethyl 7β-amino-3-acetoxymethyl-Δ³-O-2-isocephem-4-carboxylate

The title compound is produced according to the method of Example 2 of U.K. Specification 1,229,453 by replacing the 7-aminocephalosporanic acid used therein by 7β-amino-3-acetoxymethyl-Δ³-O-2-isocephem-4-carboxylic acid.

The respective acetoxymethyl, methoxymethyl, acetonyl and phenacyl esters of 7β-amino-3-acetoxymethyl-Δ³-O-2-isocephem-4-carboxylic acid are prepared by substituting in the method above for the chloromethyl pivalate used therein an equimolar weight of chloromethyl acetate, chloromethyl methyl ether, chloroacetone and phenacyl bromide, respectively.

EXAMPLE 22

The procedure of Example 21 is repeated using 7β-amino-3-hydroxymethyl-Δ³-O-2-isocephem-4-carboxylic acid, 7β-amino-3-formyloxymethyl-Δ³-O-2-isocephem-4-carboxylic acid, 7β-amino-3-methylsulfonyloxymethyl-Δ³-O-2-isocephem-4-carboxylic acid, 7β-amino-3-carbamoyloxymethyl-Δ³-O-2-isocephem-4-carboxylic acid, 7β-amino-3-(1-methyltetrazol-5-yloxymethyl)-Δ³-O-2-isocephem-4-carboxylic acid or 7β-amino-3-bromomethyl-Δ³-O-2-isocephem-4-carboxylic acid in place of the 7β-amino-3-acetoxymethyl-Δ³-O-2-isocephem-4-carboxylic acid used therein. There are produced the corresponding pivaloyloxymethyl esters. Replacement of chloromethyl pivalate by chloromethyl acetate, chloromethyl methyl ether, chloroacetone and phenacyl bromide, respectively, produces the corresponding acetoxymethyl, methoxymethyl, acetonyl and phenacyl esters.

EXAMPLE 23

Benzyl 7β-phenoxyacetamido-3-acetoxymethyl-Δ³-O-2-isocephem-4-carboxylate

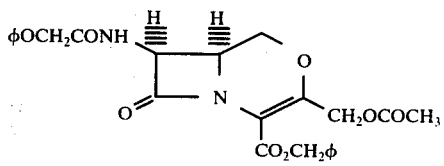

A mixture of benzyl 7β-amino-3-acetoxymethyl-Δ³-O-2-isocephem-4-carboxylate (425 mg., 1.2 mmole) phenoxyacetic acid (183 mg., 1.2 mmole) EEDQ (325 mg., 1.3 mmole) and 15 ml. of methylene chloride[1] was stirred at room temperature for 1.5 hours. The mixture was then washed with 10% HCl (once, 20 ml.), brine (once, 20 ml.), 10% $NaHCO_3$ solution (once, 30 ml.), brine (once, 30 ml.), and finally dried (anhydrous $Na_2SO_4$) and evaporated to dryness leaving a colorless oil. This oil was triturated with diethylether to give 410 mg. of crude amide title product in 71% yield. This material was dry column chromatographed over activity III silica gel by eluting with diethylether to give 400 mg. of title product as a white crystalline solid; m.p. 146° C. (corr.).

Anal. Calc'd for $C_{25}H_{24}N_2O_8$: C, 62.49; H, 5.04; N, 5.83. Found: C, 62.58, H, 5.07; N, 5.83.

[1] The methylene chloride used in this experiment was reagent grade which had been further purified by passing over a calcium chloride column.

EXAMPLE 24

7β-Phenoxyacetamido-3-acetoxymethyl-Δ³-O-2-isocephem-4-carboxylic acid

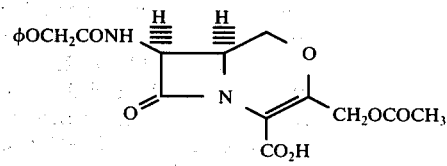

A mixture of benzyl 7β-phenoxyacetamido-3-acetoxymethyl-Δ³-O-2-isocephem-4-carboxylate (100 mg., 0.208 mmole), 100 mg. of 10% Pd-C and 50 ml. of THF was hydrogenated for 15 minutes in a Parr hydrogenator with an initial pressure of 40 p.s.i.g. The catalyst was filtered off and the filtrate evaporated to dryness leaving 50 mg. of white crystalline solid title product; m.p. 160°–170° C. (corr.) (decomposition) (recrystallized from ethanol.

Anal. Calc'd for $C_{18}H_{18}N_2O_8$: C, 55.38; H, 4.65; N, 7.18. Found: C, 55.32; H, 4.88; N, 7.13.

A sample of the title product (called BC-L53) after solution in water and dilution with Nutrient Broth was found to exhibit the following Minimum Inhibitory Concentrations (M.I.C.) in mcg./ml. versus the indicated microorganisms as determined by overnight incubation at 37° C. by tube dilution. Cephalexin was included as a comparison compound.

Table 1

M.I.C. in mcg./ml.

| Organism | | BC-L53 | Cephalexin |
|---|---|---|---|
| D. pneumoniae + 5% serum* | A9585 | .06 | .13 |
| Str. pyogenes + 5% serum* | A9604 | .13 | .13 |
| S. aureus Smith** | A9537 | 1 | .25 |
| S. aureus Smith** + 50% serum | A9537 | 4 | .5 |
| S. aureus BX1633-2 at 10⁻³ dil'n | A9606 | 1 | 1 |
| S. aureus BX1633-2 at 10⁻² dil'n | A9606 | 125 | 4 |
| S. aureus meth.-resist.; at 10⁻³ dil'n | A15097 | 16 | 32 |
| Sal. enteritidis** | A9531 | 2 | 2 |
| E. coli Juhl** | A15119 | 16 | 4 |
| E. coli** | A9675 | 125 | 8 |
| K. pneumoniae** | A9977 | 16 | 2 |
| K. pneumoniae** | A15130 | >125 | 8 |
| Pr. mirabilis** | A9900 | 4 | 4 |
| Pr. morganii** | A15153 | >125 | >125 |
| Ps. aeruginosa** | A9843A | >125 | >125 |
| Ser. marcescens** | A20019 | >125 | >125 |
| Ent. cloacae | A9656 | >125 | >125 |
| Ent. cloacae | A9657 | 63 | 2 |
| Ent. cloacae | A9659 | >125 | >125 |

*50% Nutrient Broth - 45% Antibiotic Assay Broth
**at 10⁻⁴ dilution.

EXAMPLE 25

7β-Phenoxyacetamido-3-hydroxymethyl-Δ³-0-2-isocephem-4-carboxylic acid

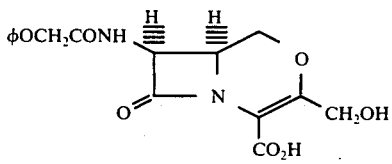

A. Acylation to prepare benzyl 7β-phenoxyacetamido-3-benzyloxymethyl-Δ³-0-2-isocephem-4-carboxylate To benzyl 7β-amino-3-benzyloxymethyl-Δ³-0-2-isocephem-4-carboxylate (0.4 g. 1.01 mmole) dissolved in 100 ml. of $CH_2Cl_2$ was added EEDQ (0.25 g., 1.01 mmole) and phenoxyacetic acid (0.154 g., 1.01 mmole). The solution was stirred at room temperature for 2 hours, washed successively with a 1% $NaHCO_3$ solution, 10% hydrochloric acid and brine solution, dried over $Na_2SO_4$ and concentrated on the rotary evaporator to give 0.53 g. of crude benzyl 7β-phenoxyacetamido-3-benzyloxymethyl-Δ³-0-2-isocephem-4-carboxylate. Purification was achieved through chromatography over silica gel and gave 0.35 g. (66%) of pure benzyl ester.

B. Simultaneous de-blocking at 3- and 4- positions

The benzyl ester intermediate of Step A (0.35 g., 0.66 mmole) was hydrogenated at atmospheric pressure in a total of 55 ml. of ethyl acetate in the presence of 20% $Pd(OH)_2$ (0.35 g.). When hydrogenation was complete (18 hours), the catalyst was removed by filtration over Celite and the filtrates were concentrated on the rotary evaporator to give 0.18 g. of semi-solid which crystallized after trituration with ether. Recrystallization from acetone-ether gave 0.101 g. of white solid; m.p. 157°–159° C. Spectral data, IR and NMR, were fully consistent with the structure of the title product.

This compound was found to be identical (IR, NMR, mixed m.p.) to the compound prepared in Example 26.

Anal. Calc'd. for $C_{16}H_{16}N_2O_7$: C, 55.17; H, 4.63; N, 8.04. Found: C, 55.06; H, 4.59; N, 7.99.

A sample of the title product (called BC-L43) aster solution in water and dilution with Nutrient Broth was found to exhibit the following Minimum Inhibitory Concentrations (M.I.C.) in mcg./ml. versus the indicated microorganisms as determined by overnight incubation at 37° C. by tube dilution.

Table 2

M.I.C. in mcg./ml.

| Organism | | BC-L43 | Cephalexin |
|---|---|---|---|
| D. pneumoniae + 5% serum* | A9585 | <.25 | .13 |
| Str. pyogenes + 5% serum* | A9604 | <.25 | .13 |
| S. aureus Smith** | A9537 | <.25 | .25 |
| S. aureus Smith** + 50% serum | A9537 | 2 | 1 |
| S. aureus BX1633-2 at 10⁻³ dil'n | A9606 | 4 | 1 |
| S. aureus BX1633-2 at 10⁻² dil'n | A9606 | 63 | 4 |
| S. aureus meth.-resist.; at 10⁻³ dil'n | A15097 | 32 | 63 |
| Sal. enteritidis** | A9531 | 16 | 2 |
| E. coli Juhl** | A15119 | >125 | 8 |
| E. coli** | A9675 | >125 | 32 |
| K. pneumoniae** | A9977 | 63 | 4 |
| K. pneumoniae** | A15130 | >125 | 16 |
| Pr. mirabilis** | A9900 | 63 | 4 |
| Pr. morganii** | A15153 | >125 | >125 |
| Ps. aeruginosa** | A9843A | >125 | >125 |
| Ser. marcescens** | A20019 | >125 | >125 |
| Ent. cloacae | A9656 | >125 | >125 |
| Ent. cloacae | A9657 | >125 | 4 |
| Ent. cloacae | A9659 | >125 | >125 |

*50% Nutrient Broth - 45% Antibiotic Assay Broth
**at 10⁻⁴ dilution.

EXAMPLE 26

7β-Phenoxyacetamido-3-hydroxymethyl-Δ³-0-2-isocephem-4-carboxylic acid

A. To the crude 7β-amino intermediate from Example 16 dissolved in 60 ml. of $CH_2Cl_2$ was added EEDQ (0.741 g., 3 mmole) and phenoxyacetic acid (0.456 g., 3 mmole). The solution was stirred at room temperature for 2½ hours, washed successively with a 5% hydrochloric acid solution, water, a 1% sodium bicarbonate solution and water, dried ($Na_2SO_4$) and concentrated to give 1.48 g. of crude benzyl 7β-phenoxyacetamido-3-hydroxymethyl-Δ³-0-2-isocephem-4-carboxylate. Crystallization in ether containing a trace of ethyl acetate afforded 1.07 g. of the pure benzyl ester as a white solid.

B. The benzyl ester from Part A (0.25 g.) was hydrogenated in a Parr-shaker in ethyl acetate (50 ml.) with 20% $Pd(OH)_2$ as the catalyst at an initial pressure of 60 psi of hydrogen. After 30 minutes, the catalyst was removed by filtration over Celite and the filtrates were concentrated to give the title product (0.20 g., 98% yield) as white crystals, m.p. 156°–158° C.

This compound was found to be identical (IR, NMR, mixed m.p.) to the compound prepared in Example 25.

EXAMPLE 27

Benzyl 7β-phenoxyacetamido-3-methylsulfonylmethyl-Δ³-0-2-isocephem-4-carboxylate A solution of methanesulfonyl chloride (0.04 ml., 0.5 mmole) in methylene chloride (10 ml.) was added dropwise to a cooled (5°) and stirred solution of benzyl 7β-phenoxyacetamido-3-hydroxymethyl-Δ³-0-2-isocephem-4-carboxylate (0.219 g., 0.5 mmole) and triethylamine (0.01 ml., 0.5 mmole) in methylene chloride (10 ml.). The cooling bath was removed and the solution was stirred for 2 hours at room temperature After cooling, the solution was washed successively with 10% hydrochloric acid, diluted ammonia solution, water and brine. Drying and concentration left 0.26 g. of title product as a semi-solid. NMR analysis verified the identity of the product.

EXAMPLE 28

7β-(2-Thienylacetamido)-3-acetoxymethyl-Δ³-0-2-isocephem-4-carboxylic acid

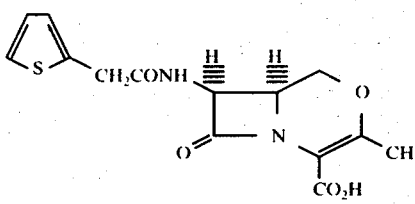

The crude amino acid hydrochloride prepared in Example 17 (4.2 g., 13.4 mmole) was treated with 150 ml. of water, cooled to 0° C., and treated slowly with sodium bicarbonate (7.5 g., 90 mmole). A solution of 2-thienylacetic acid chloride ((4.5 g., 29 mmole) in 50 ml. of acetone was added slowly and the mixture stirred for an additional hour at 0° C.

It was then extracted with ether (2 × 100 ml.) and the aqueous phase was acidified with dilute hydrochloric acid. The product was extracted into methylene chloride and the extract was dried over anhydrous sodium sulfate. Evaporation in vacuo gave a crude residue which solidified on seeding and trituration with ether. The yield of this crude material is 2.6 g. (51% yield from the azido ester).

The product was purified by crystallization from absolute ethanol giving 1.8 g. (35% yield from the azido ester) of title product with m.p. 182° (decomposition).

Anal. Calc'd. for $C_{16}H_{16}N_2O_7S$: C, 50.52; H, 4.24; N, 7.37; S, 8.43. Found: C, 50.34; H, 4.41; N, 7.47; S, 8.45.

U.V. $\lambda_{max}^{EtOH}$ 272, $\epsilon$ = 8654.

The NMR and IR were consistent with the proposed structure. M.I.C. data for the above product (called BC-L58) is shown in the following table.

Table 3
M.I.C. in mcg./ml.

| Organism | | BC-L58 | Cephalexin | Cephalothin |
|---|---|---|---|---|
| D. pneumoniae | A9585 | .03 | .25 | .06 |
| + 5% serum* | | .016 | .5 | .03 |
| Str. pyogenes | A9604 | .03 | .25 | .06 |
| + 5% serum* | | .016 | .13 | .03 |
| S. aureus Smith** | A9537 | .5 | 1 | .13 |
| | | .25 | .5 | .06 |
| S. aureus Smith** | A9537 | 1 | 1 | .13 |
| + 50% serum | | 1 | 2 | .5 |
| S. aureus BX1633-2 at 10⁻³ dil'n | A9606 | 1 | 1 | .13 |
| | | .5 | 1 | .13 |
| S. aureus BX1633-2 at 10⁻² dil'n | A9606 | 2 | 4 | .25 |
| | | 1 | 4 | .25 |
| S. aureus meth.-resist.; at 10⁻³ dil'n | A15097 | 2 | 16 | .5 |
| | | 1 | 4 | .5 |
| Sal. enteritidis** | A9531 | .5 | 2 | .25 |
| | | .13 | 4 | .25 |
| E. coli Juhl** | A15119 | 8 | 8 | 16 |
| | | 8 | 8 | 16 |
| E. coli** | A9675 | 63 | 16 | 63 |
| | | 32 | 16 | 32 |
| K. pneumoniae** | A9977 | 1 | 2 | .5 |
| | | .5 | 4 | 1 |
| K. pneumoniae** | A15130 | 63 | 16 | 16 |
| | | 32 | 8 | 16 |
| Pr. mirabilis** | A9900 | 1 | 4 | .5 |
| | | .5 | 4 | 1 |
| Pr. morganii** | A15153 | 125 | >125 | >125 |
| | | >125 | >125 | >125 |
| Ps. aeruginosa** | A9843A | >125 | >125 | >125 |
| | | >125 | >125 | >125 |
| Ser. marcescens** | A20019 | >125 | >125 | >125 |
| | | >125 | >125 | >125 |
| Ent. cloacae | A9656 | >125 | >125 | >125 |
| | | >125 | >125 | >125 |
| Ent. cloacae | A9657 | 16 | 4 | 2 |
| | | 8 | 4 | 4 |
| Ent. cloacae | A9659 | >125 | >125 | >125 |
| | | >125 | >125 | >125 |

*50% Nutrient Broth - 45% Antibiotic Assay Broth
**at 10⁻⁴ dilution.

Compound BC-L58 was resolved into its individual isomers designated BC-L68 (+ isomer) and BC-L69 (− isomer). M.I.C. data for the isomers is provided below.

Table 4
M.I.C. in mcg./ml.

| Organism | | BC-L68 | BC-L69 | Cephalexin | Cephalothin |
|---|---|---|---|---|---|
| D. pneumoniae | | | | | |
| + 5% serum* | A9585 | .016 | .5 | .5 | .03 |
| Str. pyogenes | | | | | |
| + 5% serum* | A9604 | .016 | .5 | .13 | .03 |
| S. aureus Smith** | A9537 | .06 | 4 | .5 | .06 |
| S. aureus Smith** | | | | | |
| + 50% serum | A9537 | .25 | 32 | .2 | .5 |
| S. aureus BX1633-2 at 10⁻³ dil'n | A9606 | .13 | 8 | 1 | .13 |
| S. aureus BX1633-2 at 10⁻² dil'n | A9606 | 1 | 16 | 4 | .25 |
| S. aureus meth.-resist.; at 10⁻³ dil'n | A15097 | .25 | 8 | 4 | .5 |
| Sal. enteritidis** | A9531 | .03 | 8 | 4 | .25 |
| E. coli Juhl** | A15119 | 4 | >125 | 8 | 16 |
| E. coli** | A9675 | 32 | >125 | 16 | 32 |
| K. pneumoniae** | A9977 | .13 | 32 | 4 | 1 |
| K. pneumoniae** | A15130 | 16 | >125 | 8 | 16 |
| Pr. mirabilis** | A9900 | .13 | 16 | 4 | 1 |
| Pr. morganii** | A15153 | 125 | >125 | >125 | >125 |

Table 4-continued

| Organism | | BC-L68 | BC-L69 | Cepha-lexin | Cepha-lothin |
|---|---|---|---|---|---|
| Ps. aeruginosa** | A9843A | >125 | >125 | >125 | >125 |
| Ser. marcescens** | A20019 | >125 | >125 | >125 | >125 |
| Ent. cloacae | A9656 | >125 | >125 | >125 | >125 |
| Ent. cloacae | A9657 | 16 | >125 | 4 | 4 |
| Ent. cloacae | A9659 | >125 | >125 | >125 | >125 |

*50% Nutrient Broth - 45% Antibiotic Assay Broth
**at 10⁻⁴ dilution.

EXAMPLE 29

Benzyl 7β-phenoxyacetamido-3-acetoxymethyl-$\Delta^3$-0-2-isocephem-4-carboxylate (acylation of corresponding 3-hydroxymethyl compound)

A mixture of benzyl 7β-phenoxyacetamido-3-hydroxymethyl-$\Delta^3$-0-2-isocephem-4-carboxylate (1.07 g., 2.44 mmole), acetic anhydride (1 g., 9.8 mmole) and pyridine (15 ml.) was stirred at room temperature for 1.5 hours. The reaction mixture was diluted with water and extracted with $CH_2Cl_2$. The organic phase was washed with water, 10% HCl and water, dried and concentrated to leave a solid. Recrystallization of the solid in ethyl acetate-ether gave 1.0 g. of title product as white crystals, m.p. 144°–146°. This compound was found to be identical (mixed m.p., IR and NMR) to the product of Example 23.

The benzyl ester may be converted to the corresponding free acid compound by the procedure of Example 24.

EXAMPLE 30

Separation of Diastereomers of

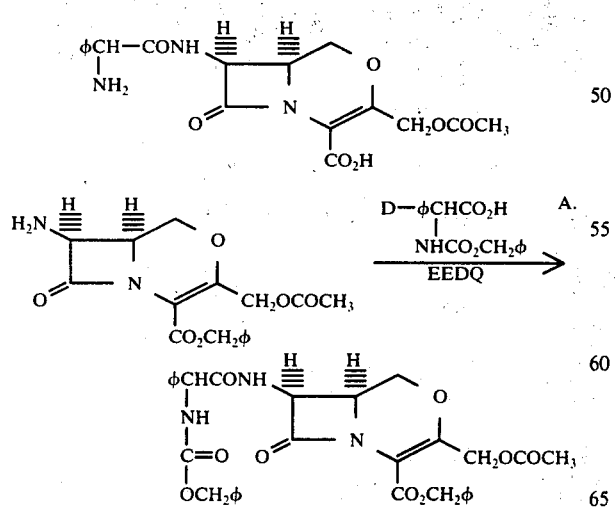

A solution of benzyl 7β-amino-3-acetoxymethyl-$\Delta^3$-0-2-isocephem-4-carboxylate (1.86 g., 5.4 mmole), D-carbobenzoxyphenylglycine (1.54 g., 5.4 mmole) and EEDQ (1.46 g., 6.0 mmole) in 50 ml. of methylene chloride was stirred at 24° for 16 hours. The resulting solution was washed with 5% sodium bicarbonate, 10% hydrochloric acid and dilute sodium chloride solutions, then dried (sodium sulfate) and evaporated in vacuo to give a yellow tar, 3.27 g. The tar was dissolved in methylene chloride and absorbed onto 16.5 g. of silica gel (grade III) which was placed on a chromatographic column of 165 g. of silica gel. Elution with ether gave (after some front running impurities) the major component as a partially separated mixture of two diastereomers. The last fraction (2.0 g.) (shown by NMR to be a 34:66 ratio of isomers) was re-absorbed onto 10 g. of silica gel and chromatographed on 100 g. of silica gel. Elution with ether:hexane 9:1 changing to ether gave further separation of the isomers. The last fraction (371 mg.) was found to be a 15:85 mixture of two isomers. The mixture had $\alpha_D^{25°} = +26.5°$ ($CHCl_3$).

B.

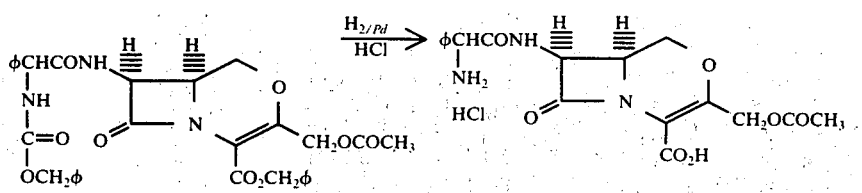

To a solution of 325 mg. (0.53 mmole) of the mixture of isomers from Part A in 8 ml. of ethyl acetate was added 8 ml. of ethanol, 0.53 ml. of 1.00 M hydrochloric acid and 320 mg. of 30% palladium-on-diatomaceous-earth. The mixture was hydrogenated at 24° and 1 atmosphere until uptake of hydrogen ceased. The catalyst was removed by filtration and the solvent evaporated in vacuo to give the amino acid hydrochloride salt as an amorphous solid, 210 mg. NMR showed the product to be a 15:85 ratio mixture of isomers (the 85% isomer is arbitrarily designated isomer B) and to contain about ⅓ mole of ethanol and 1 to 2 mole of water. The chemical purity of the product was estimated from U.V. spectrum to be about 70%. The product had $\alpha_D^{25°} = +72.0°$ (DMSO) and U.V. $\lambda_{max}^{EtOH}$ 270 mm. ($\epsilon = 6600$).

IR and NMR spectra were in agreement with the proposed structure.

A sample of the product (called BC-L65) was found to exhibit the following Minimum Inhibitory Concentrations.

Table 5

| | M.I.C. in mcg./ml. | |
|---|---|---|
| Organism | BC-L65 | Cepha lexin |
| D. pneumoniae +5% serum* | A9585 | .06 | .25 |
| Str. pyogenes | A9604 | .06 | .25 |

Table 5-continued

| | | M.I.C. in mcg./ml. | |
|---|---|---|---|
| Organism | | BC-L65 | Cephalexin |
| +serum* | | | |
| S. aureus Smith** | A9537 | 1 | 1 |
| S. aureus Smith** +50% serum | A9537 | 4 | 2 |
| S. aureus BX1633-2 at 10⁻³ dil'n | A9606 | 2 | 4 |
| S. aureus BX1633-2 at 10⁻² dil'n | A9606 | 8 | 4 |
| S. aureus meth.-resist.; at 10⁻³ dil'n | A15097 | 4 | 8 |
| Sal. enteritidis** | A9531 | .5 | 4 |
| E. coli Juhl** | A15119 | 1 | 8 |
| E. coli** | A9675 | 4 | 16 |
| K. pneumoniae** | A9977 | 1 | 4 |
| K. pneumoniae** | A15130 | 8 | 16 |
| Pr. mirabilis** | A9900 | .5 | 8 |
| Pr. morganii** | A15153 | 32 | >125 |
| Ps. aeruginosa** | A9843A | >125 | >125 |
| Ser. marcescens** | A20019 | 125 | >125 |
| Ent. cloacae | A9656 | 125 | >125 |
| Ent. cloacae | A9657 | 2 | 4 |
| Ent. cloacae | A9659 | 32 | >125 |

*50% Nutrient Broth - 45% Antibiotic Assay Broth
**at 10⁻⁴ dilution.

EXAMPLE 31

Repeating the general N-acylation procedures of Examples 23, 25, 26, 28 or 30 to react the following acylating agents with 7β-amino-3-acetoxymethyl-Δ³-0-2-isocephem-4-carboxylic acid (or an ester or salt thereof), the following products are obtained after removal of any functional blocking groups.

| Acylating Agent | Product |
|---|---|
| mixed anhydride of potassium 2-(1-carbomethoxypropen-2-ylaminomethyl)phenylacetate with isobutyl chloroformate | 7β-(2-Aminomethylphenyl-acetamido)-3-acetoxymethyl-Δ³-0-2-isocephem-4-carboxylic acid |
| α-benzoylureidophenyl-acetic acid | 7β-(α-Benzoylureidophenyl-acetamido)-3-acetoxymethyl-Δ³-0-2-isocephem-4-carboxylic acid |
| 2,6-dimethoxybenzoyl chloride | 7β-(2,6-Dimethoxybenzamido)-3-acetoxymethyl-Δ³-0-2-isocephem-4-carboxylic acid |
| D-anhydro-o-carboxy-mandelic acid | 7β-(D-α-Hydroxyphenylacetamido)-3-acetoxymethyl-Δ³-0-2-isocephem-4-carboxylic acid |
| 3 benzyl-1,2,4-oxadiazole-5-one-4-acetic acid | 7β-[N-(Phenylacetimidoyl)-aminoacetamido]-3-acetoxymethyl-Δ³-0-2-isocephem-4-carboxylic acid |
| valeric acid | 7β-Valeramido-3-acetoxymethyl-Δ³-0-2-isocephem-4-carboxylic acid |
| phenylacetic acid | 7β-Phenylacetamido-3-acetoxymethyl-Δ³-0-2-isocephem-4-carboxylic acid |
| 3-thienylacetyl chloride | 7β-(3-Thienylacetamido)-3-acetoxymethyl-Δ³-0-2-isocephem-4-carboxylic acid |
| α-carboxybenzyl-phenyl-acetic acid | 7β-[α-carboxy-α-phenyl-acetamido]-3-acetoxymethyl-Δ³-0-2-isocephem-4-carboxylic acid |
| o-hydroxyphenylacetic acid | 7β-(o-Hydroxyphenylacetamido)-3-acetoxymethyl-Δ³-0-2-isocephem-4-carboxylic acid |
| cyanoacetic acid | 7β-[cyanoacetamido]-3-acetoxymethyl-Δ³-0-2-isocephem-4-carboxylic acid |
| α-cyanopropionic acid | 7β-(α-cyanopropionamido)-3-acetoxymethyl-Δ³-0-2-isocephem-4-carboxylic acid |
| 2-(2H)-tetrazoleacetic acid | 7β-[2-(2H)-tetrazolylacetamido]-3-acetoxymethyl-Δ³-0-2-isocephem-4-carboxylic acid |
| 3-(o-chlorophenyl)-5-methyl-4-isoxazole-carboxylic acid chloride | 7β-[3-(o-chlorophenyl)-5-methylisoxazol-4-ylcarboxamido]-3-acetoxymethyl-Δ³-0-2-isocephem-4-carboxylic acid |
| 1-(1H)-tetrazolylacetyl chloride | 7β-[1-(1H)-tetrazolylacetamido]-3-acetoxymethyl-Δ³-0-2-isocephem-4-carboxylic acid |

EXAMPLE 32

Repeating the general N-acylation procedures of the examples above to react the following acylating agents with 7β-amino-3-acetoxymethyl-Δ³-0-2-isocephem-4-carboxylic acid (or an ester or salt thereof), the following products are obtained after removal of any functional blocking groups.

| Acylating Agents | Product |
|---|---|
| 4-nitrophenylacetyl chloride | 7β-(4-nitrophenylacetamido)-3-acetoxymethyl-Δ³-0-2-isocephem-4-carboxylic acid |
| p-fluorophenylacetyl chloride | 7β-(p-fluorophenylacetamido)-3-acetoxymethyl-Δ³-0-2-isocephem-4-carboxylic acid |
| p-acetoxyphenylacetyl chloride | 7β-(p-acetoxyphenylacetamido)-3-acetoxymethyl-Δ³-0-2-isocephem-4-carboxylic acid |
| o-chlorophenylacetyl chloride | 7β-(o-chlorophenylacetamido)-3-acetoxymethyl-Δ³-0-2-isocephem-4-carboxylic acid |
| p-aminophenylacetyl chloride | 7β-(p-aminophenylacetamido)-3-acetoxymethyl-Δ³-0-2-isocephem-4-carboxylic acid |
| p-methylphenylacetyl chloride | 7β-(p-methylphenylacetamido)-3-acetoxymethyl-Δ³-0-2-isocephem-4-carboxylic acid |
| 4-guanidinophenylacetyl chloride hydrochloride | 7β-(4-guanidinophenylacetamido)-3-acetoxymethyl-Δ³-0-2-isocephem-4-carboxylic acid |
| 4-isopropylphenylacetyl chloride | 7β-(4-isopropylphenylacetamido)-3-acetoxymethyl-Δ³-0-2-isocephem-4-carboxylic acid |
| 4-methylthiophenylacetyl chloride | 7β-(4-methylthiophenylacetamido)-3-acetoxymethyl-Δ³-0-2-isocephem-4-carboxylic acid |
| 4-cyanophenylacetyl chloride | 7β-(4-cyanophenylacetamido)-3-acetoxymethyl-Δ³-0-2-isocephem-4-carboxylic acid |
| 4-methoxyphenylacetyl chloride | 7β-(4-methoxyphenylacetamido)-3-acetoxymethyl-Δ³-0-2-isocephem-4-carboxylic acid |
| 2,6-dimethoxyphenylacetyl chloride | 7β-(2,6-dimethoxyphenylacetamido)-3-acetoxymethyl-Δ³-0-2-isocephem-4-carboxylic acid |
| 3-sulfamylphenylacetyl chloride | 7β-(3-sulfamylphenylacetamido)-3-acetoxymethyl-Δ³-0-2-isocephem-4-carboxylic acid |
| 2-methyl-4-chlorophenyl-acetyl chloride | 7β-(2-methyl-4-chlorophenyl-acetamido)-3-acetoxymethyl-Δ³-0-2-isocephem-4-carboxylic acid |
| sydnone-3-acetyl chloride | 7β-(sydnone-3-acetamido)-3-acetoxymethyl-Δ³-0-2-isocephem-4-carboxylic acid |
| sydnone-4-acetyl chloride | 7β-(sydnone-4-acetamido)-3-acetoxymethyl-Δ³-0-2-isocephem-4-carboxylic acid |
| 2-furylacetyl chloride | 7β-(2-furylacetamido)-3-acetoxymethyl-Δ³-0-2-isocephem-4-carboxylic acid |
| 3-furylacetyl chloride | 7β-(3-furylacetamido)-3-acetoxymethyl-Δ³-0-2-isocephem-4-carboxylic acid |
| 1,2,5-thiadiazole-3-acetyl chloride | 7β-(1,2,5-thiadiazole-3-acetamido)-3-acetoxymethyl-Δ³-0-2-isocephem-4-carboxylic acid |
| 1-cyclohexenylacetyl chloride | 7β-(1-cyclohexenylacetamido)-3-acetoxymethyl-Δ³-0-2-isocephem-4-carboxylic acid |
| 1,4-cyclohexadienyl-acetyl chloride | 7β-(1,4-cyclohexadienyl-acetamido)-3-acetoxymethyl-Δ³-0-2-isocephem-4-carboxylic acid |
| 3-(1,4-cyclohexadien-1-yl)propionyl chloride | 7β-[3-(1,4-cyclohexadien-1-yl)-propionamido]-3-acetoxymethyl-Δ³-0-2-isocephem-4-carboxylic acid |
| isothiazol-4-yl-acetic acid | 7β-(isothiazol-4-yl-acetamido)-3-acetoxymethyl-Δ³-0-2-isocephem-4-carboxylic acid |
| isothiazol-5-yl-acetic acid | 7β-(isothiazol-5-yl-acetamido)-3-acetoxymethyl- Δ³-0-2-isocephem-4-carboxylic acid |
| isothiazol-3-yl-acetic acid | 7β-(isothiazol-3-yl-acetamido)-3-acetoxymethyl-Δ³-0-2- |

-continued

| Acylating Agents | Product |
|---|---|
| 5-phenyl-1,3,4-thiadiazolyl-2-yl-acetyl chloride | isocephem-4-carboxylic acid 7β-(5-phenyl-1,3,4-thiadiazol-2-yl-acetamido)-3-acetoxymethyl-Δ$^1$-0-2-isocephem-4-carboxylic acid |
| thiazol-2-yl-acetyl chloride | 7β-(thiazol-2-yl-acetamido)-3-acetoxymethyl-Δ$^1$-0-2-isocephem-4-carboxylic acid |
| imidazol-2-yl-acetyl chloride | 7β-(imidazol-2-yl-acetamido)-3-acetoxymethyl-Δ$^1$-0-2-isocephem-4-carboxylic acid |
| 1,2,3-triazol-4-yl-acetic acid | 7β(1,2,3-triazol-4-yl-acetamido)-3-acetoxymethyl-Δ$^1$-0-2-isocephem-4-carboxylic acid |
| oxazol-2-yl-acetyl chloride | 7β-oxazol-2-yl-acetamido)-3-acetoxymethyl-Δ$^1$-0-2-isocephem-4-carboxylic acid |
| 4-pyridylacetyl chloride | 7β-(4-pyridylacetamido)-3-acetoxymethyl-Δ$^1$-0-2-isocephem-4-carboxylic acid |
| 3-pyridylacetyl chloride | 7β-(3-pyridylacetamido)-3-amido-3-acetoxymethyl-Δ$^1$-0-isocephem-4-carboxylic acid |
| 3-phenylpropionyl chloride | 7β-(3-phenylpropionamido)-3-acetoxymethyl-Δ$^1$-0-2-isocephem-4-carboxylic acid |
| 3-(p-chlorophenyl)propionyl chloride | 7β-[3-(p-chlorophenyl)propionamido]-3-acetoxymethyl-Δ$^1$-0-2-isocephem-4-carboxylic acid |
| 3-(p-methoxyphenyl)propionyl chloride | 7β-[p-methoxyphenyl)propionamido]-3-acetoxymethyl-Δ$^1$-0-2-isocephem-4-carboxylic acid |
| 3-(p-sulfamylphenyl)-propionyl chloride | 7β-[3-(p-sulfamylphenyl)propionamido]-3-acetoxymethyl-Δ$^1$-0-2-isocephem-4-carboxylic acid |
| 3-(3,4-dimethoxyphenyl)-propionyl chloride | 7β-[3-(3,4-dimethoxyphenyl)-propionamido]-3-acetoxymethyl-Δ$^1$-0-2-isocephem-4-carboxylic acid |
| 3-(p-hydroxyphenyl)-propionic acid | 7β-[3-(p-hydroxyphenyl)propionamido]-3-acetoxymethyl-Δ$^1$-0-2-isocephem-4-carboxylic acid |
| 3-(p-nitrophenyl)-propionic acid | 7β-[3-(p-nitrophenyl)propionamido]-3-acetoxymethyl-Δ$^1$-0-2-isocephem-4-carboxylic acid |
| 3-(2-thienyl)propionyl | 7β-[3-(2-thienyl)propionamido]-3-acetoxymethyl-Δ$^1$-0-2-isocephem-4-carboxylic acid |
| 3-(3-thienyl)propionyl | 7β-[3-(3-thienyl)propionamido]-3-acetoxymethyl-Δ$^1$-0-2-isocephem-4-carboxylic acid |
| cyclohexylacetic acid | 7β-(cyclohexylacetamido)-3-acetoxymethyl-Δ$^1$-0-2-isocephem-4-carboxylic acid |
| 3-phenyl-5-methylisoxazol-4-yl-acetic acid | 7β-(3-phenyl-5-methylisoxazol-4-yl-acetamido)-3-acetoxymethyl-Δ$^1$-0-2-isocephem-4-carboxylic acid |
| o-aminomethylphenylacetic acid | 7β-(o-aminomethylphenyl-acetamido)-3-acetoxymethyl-Δ$^1$-0-2-isocephem-4-carboxylic acid |
| 3-methoxy-4-furazanacetyl chloride | 7β-(3-methoxy-4-furazan-acetamido)-3-acetoxymethyl-Δ$^1$-0-2-isocephem-4-carboxylic acid |

EXAMPLE 33

Repeating the general N-acylation procedures of the examples above to react the following acylating agents with 7β-amino-3-acetoxymethyl-Δ$^3$-0-2-isocephem-4-carboxylic acid (or an ester or salt thereof), the following products are obtained after removal of any functional blocking groups.

| Acylating Agent | Product |
|---|---|
| p-nitrophenoxyacetic acid | 7β-(p-nitrophenoxyacetamido)-3-acetoxymethyl-Δ$^1$-0-2-isocephem-4-carboxylic acid |
| p-fluorophenoxy-acetic acid | 7β-(p-fluorophenoxyacetamido)-3-acetoxymethyl-Δ$^1$-0-2-isocephem-4-carboxylic acid |
| o-chlorophenoxyacetic acid | 7β-(o-chlorophenoxyacetamido)-3-acetoxymethyl-Δ$^1$-0-2-isocephem-4-carboxylic acid |
| p-sulfamylphenoxyacetic | 7β-(p-sulfamylphenoxyacetamido)- |

-continued

| Acylating Agent | Product |
|---|---|
| acid | 3-acetoxymethyl-Δ$^1$-0-2-isocephem-4-carboxylic acid |
| p-methylphenoxyacetic acid | 7β-(p-methylphenoxyacetamido)-3-acetoxymethyl-Δ$^1$-0-2-isocephem-4-carboxylic acid |
| 4-hydroxyphenoxyacetic | 7β-(4-hydroxyphenoxyacetamido)-3-acetoxymethyl-Δ$^1$-0-2-isocephem-4-carboxylic acid |
| 2,4-dichloro-phenoxyacetic acid | 7β-(2,4-dichlorophenoxy-acetamido)-3-acetoxymethyl-Δ$^1$-0-2-isocephem-4-carboxylic acid |
| 2,6-dimeth-oxyphenoxyacetic acid | 7β-(2,6-dimethoxyphenoxy-acetamido)-3-acetoxymethyl-Δ$^1$-0-2-isocephem-4-carboxylic acid |
| 4-cyanophenoxyacetic acid | 7β-(4-cyanophenoxyacetamido)-3-acetoxymethyl-Δ$^1$-0-2-isocephem-4-carboxylic acid |
| α-phenoxypropionic acid | 7β-(α-phenoxypropionamido)-3-acetoxymethyl-Δ$^1$-0-2-isocephem-4-carboxylic acid |
| α-(2-chlorophenoxy)-propionic acid | 7β-(α-(2-chlorophenoxy)propion-amido]-3-acetoxymethyl-Δ$^1$-0-2-isocephem-4-carboxylic acid |
| α-(2,4-dichlorophenoxy)-n-butyric acid carboxylic acid | 7β-[α-(2,4-dichlorophenoxy)-n-butyramido]-3-acetoxy-methyl-Δ$^1$-0-2-isocephem-4- |
| α-phenoxyphenylacetic acid | 7β-(α-phenoxyphenylacetamido)-3-acetoxymethyl-Δ$^1$-0-2-isocephem-4-carboxylic acid |
| α-phenoxybutyric acid | 7β-(α-phenoxybutyramido)-3-acetoxymethyl-Δ$^1$-0-2-isocephem-4-carboxylic acid |
| 4-trifluoromethyl-phenoxy-acetic acid | 7β-(4-trifluoromethylphenoxy-acetamido)-3-acetoxymethyl-Δ$^1$-0-2-isocephem-4-carboxylic acid |
| benzyloxyacetyl chloride | 7β-(benzyloxyacetamido)-3-acetoxymethyl-Δ$^{3-0-2}$ isocephem-4-carboxylic acid |
| β-naphthoxyacetyl chloride | 7β-(β-naphthoxyacetamido)-3-acetoxymethyl-Δ$^1$-0-2-isocephem-4-carboxylic acid |

EXAMPLE 34

Following the general N-acylation methods of the preceeding examples, the compounds listed below are prepared by acylating 7β-amino-3-acetoxymethyl-Δ$^3$-0-2-isocephem-4-carboxylic acid with an acylating acid of the formula

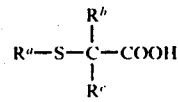

or a functional equivalent, e.g. acid halide, thereof.

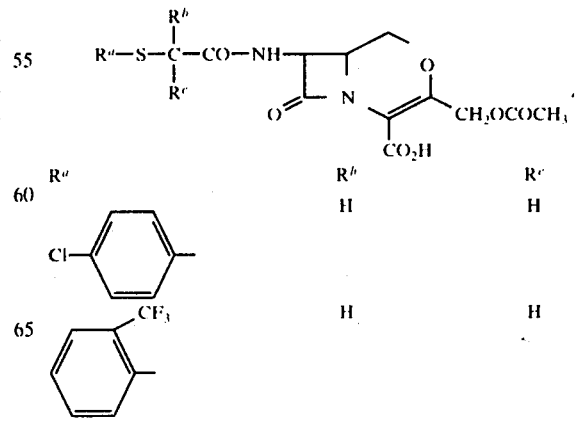

-continued $$R^a-S-\underset{R^c}{\overset{R^b}{C}}-CO-NH-\text{[β-lactam-isocephem structure]}-CH_2OCOCH_3, CO_2H$$

| $R^a$ | $R^b$ | $R^c$ |
|---|---|---|
| 2-Cl,6-CH₃-phenyl | H | H |
| 2-CH₂NH₂-phenyl | H | H |
| 4-(H₂NCH₂)-phenyl | H | H |
| phenyl | H | H |
| 4-F-phenyl | H | H |
| 4-pyridyl | H | H |
| 3-pyridyl | H | H |
| benzyl (-CH₂-phenyl) | H | H |
| 2-CN-phenyl | H | H |
| imidazolyl (2) | H | H |
| imidazolinyl (2) | H | H |
| thiazolyl (2) | H | H |
| thiazolinyl (2) | H | H |
| triazolyl (2) | H | H |
| 1-methylimidazolyl (2) | H | H |
| 2-thienyl | H | H |
| 3-thienyl | H | H |
| n-butyl | H | H |
| isobutyl | H | H |
| 2-acetamido-thiazol-5-yl | H | H |
| 2-phenyl-1,3,4-thiaidazol-5-yl | H | H |
| 2-methyl-1,3,4-oxadiazol-5-yl | H | H |

EXAMPLE 35

Following the general N-acylation methods of the proceeding examples, the compound listed below are prepared by acylation of 7β-amino-3-acetoxymethyl-Δ³-0-2-isocephem-4-carboxylic acid with the appropriate acylating acid of the general formula

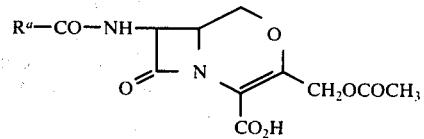

$R^a$—COOH or a functional equivalent thereof.

7β-(3-phenyl-5-methyl-isoxazol-4-ylcarboxamido)-3-acetoxymethyl-Δ³-0-2-isocephem-4-carboxylic acid;

7β-[3-(2,6-dichlorophenyl)-5-methylisoxazol-4-ylcarboxamido]-3-acetoxymethyl-Δ³-0-2-isocephem-4-carboxylic acid;

7β-(2,6-dichlorobenzamido)-3-acetoxymethyl-Δ³-0-2-isocephem-4-carboxylic acid;

7β-(2-phenylbenzamido)-3-acetoxymethyl-Δ³-0-2-isocephem-4-carboxylic acid;

7β-(2-aminomethylbenzamido)-3-acetoxymethyl-Δ³-0-2-isocephem-4-carboxylic acid;

7β-(2-carboxybenzamido)-3-acetoxymethyl-Δ³-0-2-isocephem-4-carboxylic acid;

7β-(cyclopentanecarboxamido)-3-acetoxymethyl-Δ³-0-2-isocephem-4-carboxylic acid;

7β-(1-aminocyclohexanecarboxamido)-3-acetoxymethyl-Δ³-0-2-isocephem-4-carboxylic acid;

7β-(cyclohexanecarboxamido)-3-acetoxymethyl-Δ³-0-2-isocephem-4-carboxylic acid;

7β-(1,4-cyclohexadienylcarboxamido)-3-acetoxymethyl-Δ³-0-2-isocephem-4-carboxylic acid;

7β-(4-nitrobenzamido)-3-acetoxymethyl-Δ³-0-2-isocephem-4-carboxylic acid;

7β-(4-methylbenzamido)-3-acetoxymethyl-Δ³-0-2-isocephem-4-carboxylic acid;

7β-(o-methoxybenzamido)-3-acetoxymethyl-Δ³-0-2-isocephem-4-carboxylic acid;

7β-(o-bromobenzamido)-3-acetoxymethyl-Δ³-0-2-isocephem-4-carboxylic acid;

7β-(p-ethoxybenzamido)-3-acetoxymethyl-Δ³-0-2-isocephem-4-carboxylic acid;

7β-(o-acetamidobenzamido)-3-acetoxymethyl-Δ³-0-2-isocephem-4-carboxylic acid;

7β-(p-allylbenzamido)-3-acetoxymethyl-Δ³-0-2-isocephem-4-carboxylic acid;

7β-(2,5-dihydroxybenzamido)-3-acetoxymethyl-Δ³-0-2-isocephem-4-carboxylic acid;

7β-(2-ethoxy-1-naphthamido)-3-acetoxymethyl-Δ³-0-2-isocephem-4-carboxylic acid;

7β-(2-methoxy-1-naphthamido)-3-acetoxymethyl-Δ³-0-2-isocephem-4-carboxylic acid;

7β-(o-dimethylaminobenzamido)-3-acetoxymethyl-Δ³-0-2-isocephem-4-carboxylic acid;

7β-(benzamido)-3-acetoxymethyl-Δ³-0-2-isocephem-4-carboxylic acid;

7β-(p-chlorobenzamido)-3-acetoxymethyl-Δ³-0-2-isocephem-4-carboxylic acid;

7β-(2-thienylcarboxamido)-3-acetoxymethyl-Δ³-0-2-isocephem-4-carboxylic acid;

7β-(3-thienylcarboxamido)-3-acetoxymethyl-Δ³-0-2-isocephem-4-carboxylic acid;

7β-(2-furylcarboxamido)-3-acetoxymethyl-Δ³-0-2-isocephem-4-carboxylic acid;

7β-(3-furylcarboxamido)-3-acetoxymethyl-Δ³-0-2-isocephem-4-carboxylic acid;

7β-(2'-chlorocyclobutanecarboxamido)-3-acetoxymethyl-Δ³-0-2-isocephem-4-carboxylic acid;

7β-(3'-fluorocyclopentanecarboxamido)-3-acetoxymethyl-Δ³-0-2-isocephem-4-carboxylic acid;

7β-(3'-methylcyclopentanecarboxamido)-3-acetoxymethyl-Δ³-O-2-isocephem-4-carboxyic acid;

7β-(3'-methoxycyclopentanecarboxamido)-3-acetoxy-methyl-Δ³-O-2-isocephem-4-carboxylic acid;

7β-(α-naphthamido)-3-acetoxymethyl-Δ³-O-2-isocephem-4-carboxylic acid;

7β-(β-naphthamido)-3-acetoxymethyl-Δ³-O-2-isocephem-4-carboxylic acid;

7β-(1-aminocyclopentanecarboxamido)-3-acetoxymethyl-Δ³-O-2-isocephem-4-carboxylic acid;

7β-(1-aminocycloheptanecarboxamido)-3-acetoxymethyl-Δ³-O-2-isocephem-4-carboxylic acid;

7β-(1-cyclohexenecarboxamido)-3-acetoxymethyl-Δ³-O-2-isocephem-4-carboxylic acid.

EXAMPLE 36

Repeating the general N-acylation procedures of the above examples to react trityl chloride with 7β-amino-3-acetoxymethyl-Δ³-O-2-isocephem-4-carboxylic acid (or an ester or salt thereof), there is obtained after removal of any carboxyl-protecting group, 7β-triphenylmethylcarboxamido-3-acetoxymethyl-Δ³-O-2-isocephem-4-carboxylic acid.

EXAMPLE 37

Following the acylation methods of the preceeding examples and in particular those disclosed in U.S. Pat. No. 3,546,219, the compounds listed below are prepared by reacting 7β-amino-3-acetoxymethyl-Δ³-O-2-isocephem-4-carboxylic acid (or an ester or salt thereof), with the appropriate acylating agent.

$R^y$CO—CO—NH-[β-lactam-isocephem structure with CH$_2$OCOCH$_3$ and CO$_2$H]

$R^y$ phenyl
p-acetamidophenyl $R^y$ p-methoxyphenyl
p-methylphenyl
2-methoxy-5-methylphenyl
m-chlorophenyl
o-nitrophenyl
2,4-dichlorophenyl
α-naphthyl
2-phenanthryl
p-aminophenyl
2-thienyl
p-dimethylaminophenyl.

EXAMPLE 38

Following the acylation methods of the preceeding examples and in particular those disclosed in U.K. Pat. Nos. 1,296,081 and 1,294,541, the compounds listed below are prepared by reacting 7β-amino-3-acetoxymethyl-Δ³-O-2-isocephem-4-carboxylic acid or an ester or salt thereof with an acylating agent of the formula $R^a$—CH—COOH
    |
    NH
    |
X=C
    |
H—N—C—R'
       ‖
       X' or a functional equivalent thereof.

[Structure: $R^a$—CH(NH-C(=X)-NH-C(=X')-R')—CONH—β-lactam-isocephem with CH$_2$OCOCH$_3$ and CO$_2$H]

| $R^a$ | X | X' | R' |
|---|---|---|---|
| phenyl | O | imino | NH$_2$ |
| 2-thienyl | O | imino | NH$_2$ |
| 3-thienyl | O | imino | NH$_2$ |
| m-nitrophenyl | O | imino | NH$_2$ |
| m-aminophenyl | O | imino | NH$_2$ |
| p-methylphenyl | O | imino | NH$_2$ |
| p-chlorophenyl | O | imino | NH$_2$ |
| p-methoxyphenyl | O | imino | NH$_2$ |
| p-hydroxyphenyl | O | imino | NH$_2$ |
| p-dimethylaminophenyl | O | imino | NH$_2$ |
| 3,4-dimethoxyphenyl | O | imino | NH$_2$ |
| m-methoxyphenyl | O | imino | NH$_2$ |
| p-acetamidophenyl | O | imino | NH$_2$ |
| m-hydroxyphenyl | O | imino | NH$_2$ |
| 3,5-dichloro-4-hydroxyphenyl | O | imino | NH$_2$ |
| 3-chloro-4-hydroxyphenyl | O | imino | NH$_2$ |
| phenyl | O | O | 2-furyl |
| 2-thienyl | O | O | 2-furyl |
| 3-thienyl | O | O | 2-furyl |
| phenyl | O | O | phenyl |
| 2-thienyl | O | O | phenyl |
| phenyl | O | O | 2-thienyl |
| p-chlorophenyl | O | O | 2-furyl |
| p-hydroxyphenyl | O | O | 2-furyl |
| 3-chloro-4-hydroxyphenyl | O | O | 2-furyl |
| 3,5-dichloro-4-hydroxyphenyl | O | O | 2-furyl |
| m-aminophenyl | O | O | 2-furyl |
| p-methylphenyl | O | O | 2-furyl |
| p-dimethylaminophenyl | O | O | 2-furyl |
| p-methoxyphenyl | O | O | 2-furyl |
| m-hydroxyphenyl | O | O | 2-furyl |
| p-acetamidophenyl | O | O | 2-furyl |
| m-nitrophenyl | O | O | 2-furyl |
| phenyl | O | O | CH$_3$ |
| 2-thienyl | O | O | CH$_3$ |
| 3-thienyl | O | O | CH$_3$ |
| phenyl | O | O | —CH$_2$—C$_6$H$_5$ |
| phenyl | O | O | [pyridyl ring] |
| phenyl | O | O | [thiadiazolyl ring] |
| phenyl | O | O | [isoxazolyl ring] |
| phenyl | O | O | [H$_3$C-substituted methylisoxazolyl ring with CH$_3$] |

-continued

| $R^a$ | X | X' | $R^i$ |
|---|---|---|---|
| phenyl | O | O | 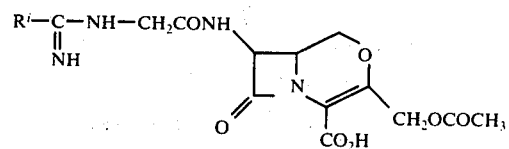 |
| phenyl | O | O | |
| phenyl | O | O | |
| phenyl | O | O | |
| phenyl | O | O | |
| phenyl | S | O | 2-furyl |
| 2-thienyl | S | O | 2-furyl |
| 3-thienyl | S | O | 2-furyl |
| p-hydroxyphenyl | S | O | $CH_3$ |
| phenyl | O | imino | phenyl |
| phenyl | O | imino | |
| 2-thienyl | | | |
| phenyl | O | imino | 2-furyl |
| 3-thienyl | O | imino | phenyl |
| phenyl | O | imino | 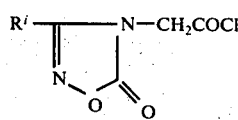 |

EXAMPLE 39

When 7β-amino-3-acetoxymethyl-Δ³-0-2-isocephem-4-carboxylic acid or an ester or salt thereof is acylated according to the procedures above and in particular those disclosed in U.S. Pat. No. 3,692,779 with an acid chloride of the formula

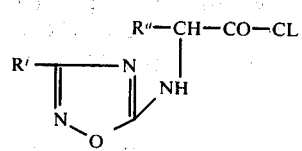

There are produced the compounds listed below.

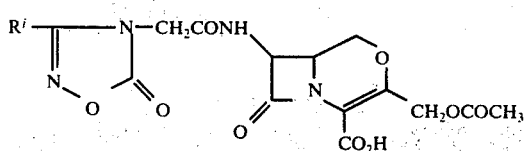

EXAMPLE 40

When the 7-acylamido-3-acetoxymethyl-Δ³-0-2-isocephem-4-carboxylic acid compounds of Example 39 are hydrogenated as by the process of U.S. Pat. No. 3,692,779, there are produced the compounds listed below.

where $R^i$ is as defined in Example 39.

EXAMPLE 41

When 7β-amino-3-acetoxymethyl-Δ³-0-2-isocephem-4-carboxylic acid or an ester or salt thereof is acylated according to the procedures of the above examples (and in particular the procedures disclosed in U.S. Pat. No. 3,646,024) with an acid chloride of the formula there are produced the compounds listed below.

| $R^a$ | $R^i$ |
|---|---|
| phenyl | phenyl |
| phenyl | 2-thienyl |
| phenyl | 2-furyl |
| 2-thienyl | phenyl |
| 3-thienyl | 2-furyl |
| p-hydroxyphenyl | phenyl |

EXAMPLE 42

When 7β-amino-3-acetoxymethyl-Δ³-0-2-isocephem-4-carboxylic acid or an ester or salt thereof is acylated according to the procedures above and in particular according to the methods of U.S. Pat. No. 3,778,436 with an acylating agent of the formula or a functional equivalent thereof, there are produced the compounds listed below.

| $R^a$ | $R^1$ |
|---|---|
| 3,4-dimethoxyphenyl | ethyl |
| p-methylphenyl | 2-thienyl |
| 2,4-dichlorophenyl | ethyl |
| 5-methyl-3-phenyl-isoxazol-4-yl | ethyl |
| 2-thienyl | ethyl |
| 2-furyl | 2-furyl |
| phenyl | phenyl |

-continued

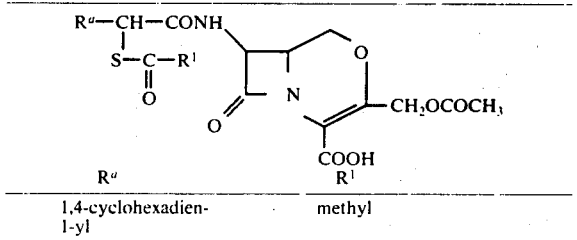

| | |
|---|---|
| 1,4-cyclohexadien-1-yl | methyl |

EXAMPLE 43

When the N-acylation and de-blocking procedures of Example 30 are repeated with the N-carbobenzoxy-D-(−)-phenylglycine used therein replaced by an equimolar weight of the N-t-butoxycarbonylamino acylating acids listed below, there are produced the following compounds.

| | |
|---|---|
| D-(−)-α-(3,5-dichloro-4-hydroxyphenyl)-α-(t-butoxycarbonylamino)acetic acid | 7β-[D-(−)-α-amino-α(3,5-dichloro-4-hydroxyphenyl)-acetamido]-3-acetoxymethyl-Δ³-0-2-isocephem-4-carboxylic acid |
| D-(−)-α-(3-chloro-4-hydroxyphenyl)-2-(t-butoxycarbonylamino)acetic acid | 7β-[D-(−)-α-amino-α-(3-chloro-4-hydroxyphenyl)acetamido]-3-acetoxymethyl-Δ³-0-2-isocephem-4-carboxylic acid |
| D-(−)-α-(p-hydroxyphenyl)-α-(t-butoxycarbonylamino)-acetic acid | 7β-[D-(−)-α-amino-α-(p-hydroxyphenyl)acetamido]-3-acetoxymethyl-Δ³-0-2-isocephem-4-carboxylic acid |
| 2-(N-t-butoxycarbonylamino)-2-(2,4,6-cycloheptatrien-1-yl)acetic acid | 7β-[α-amino-α-(2,4,6-cycloheptatrien-1-yl)acetamido]-3-acetoxymethyl-Δ³-0-2-isocephem-4-carboxylic acid |
| D-2-(t-butoxycarbonylamino)-2-(3'-hydroxyphenyl)acetic acid | 7β-[D-α-amino-α-(3'-hydroxyphenyl)acetamido]-3-acetoxymethyl-Δ³-0-2-isocephem-4-carboxylic acid |
| D-α-(t-butoxycarbonylamino)-α-4-acetamidophenylacetic acid | 7β-[D-α-amino-α-(4-acetamidophenyl)acetamido]-3-acetoxymethyl-Δ³-0-2-isocephem-4-carboxylic acid |
| D-2-(t-butoxycarbonylamino)-2-(1,4-cyclohexadienyl)acetic acid | 7β-[D-α-amino-α-(1,4-cyclohexadienyl)acetamido]-3-acetoxymethyl-Δ³-0-2-isocephem-4-carboxylic acid |
| D-3-(t-butoxycarbonylamino)-3-(1,4-cyclohexadienyl)propionic acid | 7β-[D-3'-amino-3'-(1,4-cyclohexadienyl)propionamido]-3-acetoxy-methyl-Δ³-0-2-isocephem-4-carboxylic acid |
| D-(−)-α-(2-thienyl)-α t-butoxycarbonylamino)-acetic acid | 7β-[-amino-α-(2-thienyl)-acetamido]-3-acetoxymethyl-Δ³-0-2-isocephem-4-carboxylic acid |
| D-(−)-α-(3-thienyl)-α-(t-butoxycarbonylamino)-acetic acid | 7β-[D-α-amino-α(3-thienyl)-acetamido]-3-acetoxymethyl-Δ³-0-2-isocephem-4-carboxylic acid |
| D-α-(t-butoxycarbonylamino)-α-(o-hydroxyphenyl)-acetic acid | 7β-[D-α-amino-α-(o-hydroxyphenyl)acetamido]-3-acetoxy-methyl-Δ³-0-2-isocephem-4-carboxylic acid |
| D-α-(t-butoxycarbonylamino)-α-(p-nitrophenyl)-acetic acid | 7β-[D-αamino-α-(p-nitrophenyl)-acetamido]-3-acetoxymethyl-Δ³-0-2-isocephem-4-carboxylic acid |
| D-α-(t-butoxycarbonylamino)-α-(p-methoxyphenyl)-acetic acid | 7β-[D-α-amino-α-(p-methoxyphenyl)acetamido]-3-acetoxy-methyl-Δ³-0-2-isocephem-4-carboxylic acid |
| D-α-(t-butoxycarbonylamino)-α-(p-cyanophenyl)-acetic acid | 7β-[D-α-amino-α-(p-cyanophenyl)-acetamido]-3-acetoxymethyl-Δ³-0-2-isocephem-4-carboxylic acid |
| D-α-(t-butoxycarbonylamino)-α-(p-methylthiophenyl)acetic acid | 7β-]D-60 -amino-α-(p-methylthiophenyl)acetamido]-3-acetoxy-methyl-Δ³-0-2-isocephem-4-carboxylic acid |
| D-α-(t-butoxycarbonylamino)-α(p-isopropylphenyl)acetic acid | 7β-[D-α-amino-α-(p-isopropylphenyl)acetamido]-3-acetoxy-methyl-Δ³-0-2-isocephem-4-carboxylic acid |
| D-α-(t-butoxycarbonylamino)-α-(o-sulfamylphenyl)acetic acid | 7β-[D-α-amino-α-(o-sulfamylphenyl)acetamido]-3-acetoxy-methyl-Δ³-0-2-isocephem-4-carboxylic acid |
| D-α-(t-butoxycarbonylamino)-α-(o-aminomethylphenyl)acetic acid | 7β-[D-α-amino-α-(o-aminomethylphenyl)acetamido]-3-acetoxymethyl-Δ³-0-2-isocephem-4-carboxylic acid |
| D-α(t-butoxycarbonylamino)-α-(o-dimethylaminophenyl)acetic acid | 7β-[D-α-amino-α-(o-dimethylaminophenyl)acetamido]-3-acetoxymethyl-Δ³-0-2-isocephem-4-carboxylic acid |
| D-α-(t-butoxycarbonylamino)-α-(4-chloro-2-thienyl)acetic acid | 7β-[D-α-amino-α-(4-chloro-2-thienyl)acetamido]-3-acetoxy-methyl-Δ³-0-2-isocephem-4-carboxylic acid |
| D-α-(t-butoxycarbonylamino)-α-(cylohexyl)-acetic acid | 7β-[D-α-amino-α-(cyclohexyl)-acetamido]-3-acetoxymethyl-Δ³-0-2-isocephem-4-carboxylic acid |
| D-α-(t-butoxycarbonylamino)-α-(3-trifluoromethylphenyl)acetic acid | 7β-]D-α-amino-α-(3-trifluoromethylphenyl)acetamido]-3-acetoxymethyl-Δ³-0-2-isocephem-4-carboxylic acid |

EXAMPLE 44

When 7β-amino-3-acetoxymethyl-Δ³-0-2-isocephem-4-carboxylic acid or an ester or salt thereof is acylated according to the general procedures of the preceeding examples with the acylating agents listed below (suitably protected), there are produced the following compounds.

| | |
|---|---|
| α-amino-α-(1-cyclohexenyl)-acetic acid | -]α-amino-α-(1-cyclohexenyl)-acetamido]-3-acetoxymethyl-Δ³-0-2-isocephem-4-carboxylic acid |
| α-amino-α-(isothiazol-4-yl)acetyl chloride | 7β-[α-amino-α-(isothiazol-4-yl)acetamido]-3-acetoxy-methyl-Δ³-0-2-isocephem-4-carboxylic acid |
| α-amino-α-(5-phenyl-1,3,4-thiadiazol-2-yl)acetyl chloride | 7β-[α-amino-α-(5-phenyl-1,3,4-thiadiazol-2-yl)acetamido]-3-acetoxymethyl-Δ³-0-2-isocephem-4-carboxylic acid |
| α-amino-α-(5-phenyl-1,3,4-oxadiazol-2-yl)acetyl chloride | 7β-[α-amino-α-(5-phenyl-1,3,4-oxadiazol-2-yl)acetamido]-3-acetoxymetyl-Δ³-0-2-isocephem-4-carboxylic acid |
| α-amino-α-(3-methyl-1,2,5-oxadiazol-4-yl)acetyl chloride | 7β-[α-amino-α-(3-methyl-1,2,5-oxdiazol-4-yl)acetamido]-3-acetoxymethyl-Δ³-0-2-isocephem-4-carboxylic acid |
| α-amino-α-(oxazol-2-yl)-7β-]α-amino-α(oxazol-2-yl)-acetyl chloride | acetamido]-3-acetoxymethyl-Δ³-0-2-isocephem-4-carboxylic acid |
| α-amino-α-(1H)-tetrazolylacetyl chloride | 7β-[α-amino-α-(1H)-tetrazolylacetamido]-3-acetoxymethyl-Δ³-0-2-isocephem-4-carboxylic acid |
| α-amino-α-4-isoxazolyl-acetyl chloride | 7β-[α-amino-α-(4-isoxazolyl)-acetamido]-3-acetoxymethyl-Δ³-0-2-isocephem-4-carboxylic acid |
| α-amino-α-(2-thiazolyl)-acetyl chloride | 7β-(α-amino-(2-thiazolyl)-acetamido[-3-acetoxymethyl-Δ³-0-2-isocephem-4-carboxylic acid |
| α-amino-α-(2-furyl)-acetyl chloride | 7β-[α-amino-α-(2-furyl)-acetamido]-3-acetoxymethyl-Δ³-0-2-isocephem-4-carboxylic acid |
| α-amino-α-(1,2,5-thiadiazol-3-yl)acetyl chloride | 7β-[α-amino-α-(1,2,5-thiadiazol-3-yl)acetamido]-3-acetoxy-methyl-Δ³-0-2-isocephem-4-carboxylic acid |
| q-amino-α-(3-furyl)acetyl chloride | 7β-[-amino-α-(3-furyl)-acetamido[-3-acetoxymethyl-Δ³-0-2-isocephem-4-carboxylic acid |

EXAMPLE 45

When benzyl 7β-amino-3-acetoxymethyl-Δ³-0-2-isocephem-4-carboxylate is acylated according to the general acylation procedures above with the acylating agents listed below (suitably protected if necessary), there are produced the following compounds after removal of any protecting groups:

| | |
|---|---|
| D-3-chloromandelic acid | 7β-[D-α-hydroxy-α-(3-chlorophenyl)acetamido]-3-acetoxy-methyl-Δ³-0-2-isocephem-4- |

| | |
|---|---|
| D-2-trifluoromethyl-mandelic acid | carboxylic acid<br>7β-[D-α-hydroxy-α-(2-trifluoromethylphenyl)acetamido]-3-acetoxymethyl-Δ³-0-2-isocephem-4-carboxylic acid |
| D-3-nitromandelic acid | 7β-[D-α-hydroxy-α-(3-nitrophenyl)acetamido]-3-acetoxymethyl-Δ³-0-2-isocephem-4-carboxylic acid |
| D-p-hydroxymandelic acid | 7β-[D-α-hydroxy-α-(p-hydroxyphenyl)acetamido]-3-acetoxymethyl-Δ³-0-2-isocephem-4-carboxylic acid |
| D-3-chloro-4-hydroxy-mandelic acid | 7β-[D-α-hydroxy-α-(3-chloro-4-hydroxyphenyl)acetamido]-3-acetoxymethyl-Δ³-0-2-isocephem-4-carboxylic acid |
| D-3,5-dichloro-4-hydroxy-mandelic acid | 7β-[D-α-hydroxy-α-3,5-dichloro-4-hydroxyphenyl)acetamido-9-3-acetoxymethyl-Δ³-0-2-isocephem-4-carboxylic acid |
| D-o-methylaminomandelic acid | 7β-[D-α-hydroxy-α-(o-methylaminophenyl)acetamido]-3-acetoxymethyl-Δ³-0-2-isocephem-4-carboxylic acid |
| D-p-methoxymandelic acid | 7β-[D-α-hydroxy-α-(p-methoxyphenyl)acetamido]-3-acetoxymethyl-Δ³0-2-isocephem-4-carboxylic acid |
| D-m-methylthiomandelic acid | 7β-[D-α-hydroxy-α-(m-methylthiophenyl)acetamido]-3-acetoxymethyl-Δ³-0-2-isocephem-4-carboxylic acid |
| D-m-iodomandelic acid | 7β-[D-α-hydroxy-α-(m-iodophenyl)acetamido]-3-acetoxymethyl-Δ³-0-2-isocephem-4-carboxylic acid |
| 4-isoxazoleglycolic acid | 7-β-[α-hydroxy-α-(4-isoxazolyl)-acetamido]-3-acetoxymethyl-Δ³-0-2-isocephem-4-carboxylic acid |
| 4-thiazoleglycolic acid | 7β-[α-hydroxy-α-(4-thiazolyl)-acetamido]-3-acetoxymethyl-Δ³-0-2-isocephem-4-carboxylic acid |
| 4-oxazoleglycolic acid | 7β-[α-hydroxy-α-(4-oxazolyl)-acetamido]-3-acetoxymethyl-Δ³-isocephem-4-carboxylic acid |
| 3-isothiazoleglycolic acid | 7β-[α-hydroxy-α-(3-isothiazolyl)-acetamido]-3-acetoxymethyl-Δ³-0-2-isocephem-4-carboxylic acid |
| 1,2,3-triazole-4-glycolic acid | 7β-[α-hydroxy-α-(1,2,3-triazol-4-yl)acetamido]-3-acetoxymethyl-Δ³-0-2-isocephem-4-carboxylic acid |
| 5-isoxazoleglycolic acid | 7β-[α-hydroxy-α-(5-isoxazolyl-acetamido]-3-acetoxymethyl-Δ³-0-2-isocephem-4-carboxylic acid |
| 1,2,4-triazole-3-glycolic acid | 7β-[α-hydroxy-α-(1,2,4-triazol-3-yl)acetamido]-3-acetoxymethyl-Δ³-0-2-isocephem-4-carboxylic acid |
| 2-thienylglycolic acid | 7β-[α-hydroxy-α-(2-thienyl)-acetamido]-3-acetoxymethyl-Δ³-0-2-isocephem-4-carboxylic acid |
| 3-thienylglycolic acid | 7β-[α-hydroxy-α-(3-thienyl)-acetamido]-3-acetoxymethyl-Δ³-0-2-isocephem-4-carboxylic acid |
| 1,4-cyclohexadien-1-yl-glycolic acid | 7β-[α-hydroxy-α-(1,4-cyclohexadien-1-yl)acetamido]-3-acetoxymethyl-Δ³-0-2-isocephem-4-carboxylic acid |
| 1-cyclohexenylglycolic acid | 7β-[-hydroxy-α-(1-cyclohexenyl)acetamido]-3-acetoxymethyl-Δ³-0-2-isocephem-4-carboxylic acid |
| 2-pyrrolylglycolic acid | 7β-[α-hydroxy-α-(2-pyrrolyl)-acetamido]-3-acetoxymethyl-Δ³-0-2-isocephem-4-carboxylic acid |
| 2-furylglycolic acid | 7β-[α-hydroxy-α-(2-furyl)-acetamido]-3-acetoxymethyl-Δ³-0-2-isocephem-4-carboxylic acid |
| 3-pyridylglycolic acid | 7β-[α-hydroxy-α-(3-pyridyl)-acetamido]-3-acetoxymethyl-Δ³-0-2-isocephem-4-carboxylic acid |

EXAMPLE 46

When benzyl 7β-amino-3-acetoxymethyl-Δ³-0-2-isocephem-4-carboxylate is acylated according to the general acylation procedures described above with the acylating agents listed below (suitably protected if desired), there are produced the following compounds after removal of any protecting groups:

| | |
|---|---|
| p-hydroxyphenylmalonic acid | 7β-[α-carboxy-α-(p-hydroxyphenyl)acetamido]-3-acetoxymethyl-Δ³-0-2-isocephem-4-carboxylic acid |
| 3-chloro-4-hydroxyphenyl-malonic acid | 7β-[α-carboxy-α-(3-chloro-4-hydroxyphenyl)acetamido]-3-acetoxymethyl-Δ³-0-2-isocephem-4-carboxylic acid |
| 3,5-dichloro-4-hydroxyphenylmalonic acid | 7β-[α-carboxy-α-(3,5-dichloro-4-hydroxyphenyl)acetamido-3-acetoxymethyl-Δ³-0-2-isocephem-4-carboxylic acid |
| o-chlorophenylmalonic acid | 7β-[α-carboxy-α-(o-chlorophenyl)acetamido]-3-acetoxymethyl-Δ³-0-2-isocephem-4-carboxylic acid |
| p-nitrophenylmalonic acid | 7β-[α-carboxy-α-(p-nitrophenyl)acetamido]-3-acetoxymethyl-Δ³-0-2-isocephem-4-carboxylic acid |
| p-acetoxyphenylmalonic acid | 7β-[α-carboxy-α-(p-acetoxyphenyl)acetamido]-3-acetoxymethyl-Δ³-0-2-isocephem-4-carboxylic acid |
| p-methoxyphenylmalonic | 7β-[α-carboxy-α-(p-methoxyphenyl)acetamido]-3-acetoxymethyl-Δ³-0-2-isocephem-4-carboxylic acid |
| p-methylthiophenylmalonic acid | 7β-[α-carboxy-α-(p-mrthylthiophenyl)acetamido]-3-acetoxymethyl-Δ³-0-2-isocephem-4-carboxylic acid |
| p-cyanophenylmalonic acid | 7β-[α-carboxy-α(p-cyanophenyl)-acetamido]-3-acetoxymethyl-Δ³-0-2-isocephem-4-carboxylic acid |
| m-isopropylphenylmalonic acid | 7β-[α-carboxy-α-(m-isopropylphenyl)acetamido]-3-acetoxymethyl-Δ³-0-2-isocephem-4-carboxylic acid |
| o-aminomethylphenyl-malonic acid | 7β-[α-carboxy-α-(o-aminomethylphenyl)acetamido]-3-acetoxymethyl-Δ³-0-2-isocephem-4-carboxylic acid |
| o-dimethylaminophenyl-malonic acid | 7β-[α-carboxy-α-(o-dimethylaminophenyl) acetamido]-3-acetoxymethyl-Δ³-0-2-isocephem-4-carboxylic acid |
| 2-thienylmalonic acid | 7β-[α-carboxy-α-(2-thienyl)-acetamido]-3-acetoxymethyl-Δ³-0-2-isocephem-4-carboxylic acid |
| 3-thienylmalonic acid | 7β-[α-carboxy-α-(3-thienyl)-acetamido]-3-acetoxymethyl-Δ³-0-2-isocephem-4-carboxylic acid |
| 1,4-cyclohexadienyl-malonic acid | 7β-[α-carboxy-α-(1,4-cyclohexadien-1-yl)acetamido]-3-acetoxymethyl-Δ³-0-2-isocephem-4-carboxylic acid |
| 1-cyclohexenylmalonic acid | 7β-[α-carboxy-α-(1-cyclohexenyl)acetamido]-3-acetoxymethyl-Δ³-0-2-isocephem-4-carboxylic acid |
| 2-furylmalonic acid | 7β-[α-carboxy-α-(2-furyl)-acetamido]-3-acetoxymethyl-Δ³-0-2-isocephem-4-carboxylic acid |
| 4-pyridylmalonic acid | 7β-[α-carboxy-α-(4-pyridyl)-acetamido]-3-acetoxymethyl-Δ³-0-2-isocephem-4-carboxylic acid |

EXAMPLE 47

When 7β-amino-3-acetoxymethyl-Δ³-0-2-isocephem-4-carboxylic acid or an ester or salt thereof is acylated according to the general procedures of the preceding examples with an acylating agent of the formula

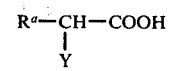

or a functional equivalent thereof, there are produced the compounds listed below

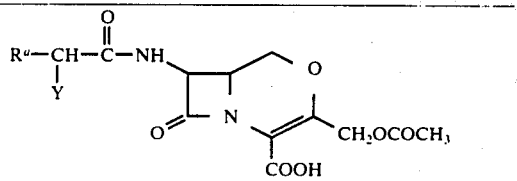

| R<sup>a</sup> | Y |
| --- | --- |
| phenyl | guanidino |
| 2-thienyl | guanidino |
| 3-thienyl | guanidino |
| 1,4-cyclohexadienyl | guanidino |
| 1-cyclohexenyl | guanidino |
| p-hydroxyphenyl | guanidino |
| 3-chloro-4-hydroxyphenyl | guanidino |
| 3,5-dichloro-4-hydroxyphenyl | guanidino |
| phenyl | ureido |
| 2-thienyl | ureido |
| 3-thienyl | ureido |
| 1-cyclohexenyl | ureido |
| 1,4-cyclohexadienyl | ureido |
| p-hydroxyphenyl | ureido |
| 3,5-dichloro-4-hydroxyphenyl | ureido |
| o-aminomethylphenyl | ureido |
| p-methylphenyl | ureido |
| m-chlorophenyl | ureido |
| phenyl | thioureido |
| 2-thienyl | thioureido |
| 3-thienyl | thioureido |
| 1-cyclohexenyl | thioureido |
| 1,4-cyclohexadienyl | thioureido |
| p-hydroxyphenyl | thioureido |
| 3-chloro-4-hydroxyphenyl | thioureido |
| 3,5-dichloro-4-hydroxyphenyl thioureido | |
| o-aminomethylphenyl | methylthioureido |
| m-chlorophenyl | allylthioureido |
| phenyl | chloro |
| 2-thienyl | bromo |
| 3-thienyl | chloro |
| 1,4-cyclohexadienyl | methoxy |
| 1-cyclohexenyl | ethoxy |
| phenyl | phenyl |
| 2-thienyl | methoxy |
| 3-thienyl | ethoxy |
| p-hydroxyphenyl | iodo |
| p-trifluoromethylphenyl | methoxy |
| 3,4-dichlorophenyl | methoxy |
| phenyl | acetoxy |
| 2-thienyl | acetoxy |
| 2-furyl | acetoxy |
| p-nitrophenyl | acetoxy |
| p-methoxyphenyl | acetoxy |
| phenyl | propionyloxy |
| phenyl | cyano |
| phenyl | So$_3$H |
| phenyl | azido |
| phenyl | methylsulfonyl |
| phenyl | 5-indanyloxycarbonyl |
| p-hydroxyphenyl | 5-indanyloxycarbonyl |
| 3-chloro-4-hydroxyphenyl | 5-indanyloxycarbonyl |
| 3,5-dichloro-4-hydroxyphenyl | 6-indanyloxycarbonyl |

EXAMPLE 48

7β-(2-Thienylacetamido)-3-(1-methyltetrazol-5-yloxymethyl)-Δ³-0-2-isocephem-4-carboxylic acid

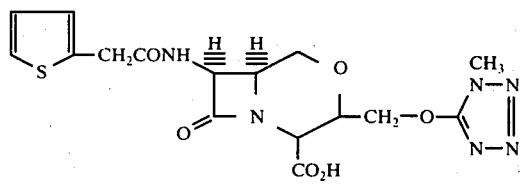

A mixture consisting of p-nitrobenzyl 7β-amino-3-(1-methyltetrazol-5-yloxymethyl)-Δ³-0-2-isocephem-4-carboxylate (0.15 g., 0.35 mmole), EEDQ (0.086 g., 0.35 mmole) and thienylacetic acid (0.05 g., 0.35 mmole) in methylene chloride (50 ml.) was kept at room temperature (protected from moisture by a calcium chloride drying tube) for 16 hours. It was then washed successively with 10% HCl, water 5% sodium bicarbonate and brine, dried (Na$_2$SO$_4$) and evaporated to dryness to give 0.18 g. of an amorphous solid which was identified by NMR as p-nitrobenzyl 7β-(2-Thienylacetamido)-3-(1-methyltetrazol-5-yloxymethyl)-66 ³-0-2-isocephem-4-carboxylate.

The p-nitrobenzyl ester (0.18 g., 0.32 mmole) was dissolved in ethylacetate (75 ml.) and n-butanol (10 ml.) in a 500 ml. Parr bottle. To this was added 20% palladium hydroxide on Celite (0.27 g.) and 0.1N hydrochloric acid (3.2 ml., 0.32 mmole). The mixture was then shaken under hydrogen (initial pressure 60 psi.) for 2½ hours. The solid was filtered off on a Celite pad and the filtrate evaporated in vacuo down to a volume of about 2 ml., when a yellow solid separated. Ether (50 ml.) and 1% sodium bicarbonate (15 ml.) were added and, after thorough shaking, the aqueous phase was isolated and carefully acidified with 10% hydrochloric acid. On cooling, white crystals separated and were collected by suction filtration, washed with cold water and dried to give the title product as a white solid (0.04 g.), m.p. 190°-192° d.

Anal. Calc'd. for $C_{16}H_{16}N_6O_6$: C, 45.71; H, 3.84; N, 19.99. Found: C, 45.63; H, 3.91; N, 20.11.

U.V. $\epsilon_{max} = 7,900$ (THF)

Table 6

| | M.I.C. in mcg./ml. | |
| --- | --- | --- |
| Organism | BC-L72 | Cephalothin |
| D. pneumoniae +5% serum* | A9585 | .06 | .06 |
| Str. pyogenes +5% serum* | A9604 | .06 | .06 |
| S. aureus Smith** | A9537 | .25 | .13 |
| S. Aureus Smith** +50% serum | A9537 | 1 | .5 |
| S. aureus BX1633-2 at 10⁻³ dil'n | A9606 | 8 | .25 |
| S. aureus BX1633-2 at 10⁻² dil'n | A9606 | 125 | .5 |
| S. aureus meth.-resist.; at 10⁻³ dil'n | A15097 | 8 | 1 |
| Sal. enteritidis** | A9531 | .5 | .25 |
| E. coli Juhl** | A15119 | 32 | 16 |
| E. coli** | A9675 | 125 | 63 |
| K. pneumoniae** | A9977 | 2 | 2 |
| K. pneumoniae** | A15130 | 63 | 16 |
| Pr. mirabilis** | A9900 | 2 | 1 |
| Pr. morganii** | A15153 | 125 | >125 |
| Ps. aeruginosa** | A9343A | >125 | >125 |
| Ser. marcescens** | A20019 | >125 | >125 |
| Ent. cloacae | A9656 | >125 | >125 |
| Ent. cloacae | A9657 | 16 | 4 |
| Ent. cloacae | A9659 | >125 | >125 |

*50% Nutrient Broth - 45% Antibiotic Assay Broth
**at 10⁻⁴ dilution.

EXAMPLE 49

7β-(2-Thienylacetamido)-3-Carbamoyloxymethyl-Δ³-0-2-isocephem-4-carboxylic acid

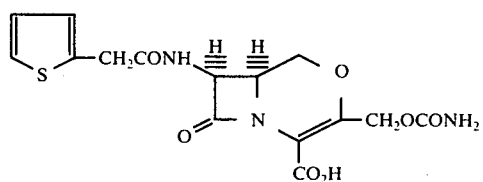

p-Nitrobenzyl 7β-azido-3-carbamoyloxymethyl-Δ³-0-2-isocephem-4-carboxylate (400 mg., 0.96 mmoles) and triethylamine (0.25 ml., 1.8 mmoles) were dissolved in 30 ml. of methylene chloride. Hydrogen sulfide was gently bubbled into the solution for 1 minute with stirring. After stirring for 30 minutes, nitrogen was bubbled through to remove most of the excess $H_2S$ and it was then evaporated in vacuo.

The residue, p-nitrobenzyl 7β-amino-3-carbamoyloxymethyl-Δ³-O-2-isocephem-4-carboxylate, was dissolved in 50 ml. of methylene chloride and treated with thienylacetic acid (150 mg., 1.05 mmoles) and EEDQ (240 mg., 1.0 mmoles). The mixture was stirred at room temperature for 18 hours and then washed with water, 1% sodium bicarbonate, water, 1% hydrochloric acid, water and brine. It was then dried over anhydrous sodium sulfate and evaporated in vacuo to give crude product which was purified by dry-column chromatography on silica gel (Activity III) eluting with 25% ethyl acetate in ether. The yield of p-nitrobenzyl 7β-(2-thienylacetamido)-3-carbamoyloxymethyl-Δ³- 0-2-isocephem-4-carboxylate was 150 mg. (29%). NMR and IR of the product ester were consistent with the proposed structure.

To a solution of 310 mg. (0.80 mmoles) of the ester in 150 ml. of ethyl acetate and 50 ml. of n-butanol was added 8 ml. of 0.1N hydrochloric acid (0.80 mmoles) and 410 mg. of 20% palladium hydroxide on carbon. The mixture was hydrogenated at room temperature on a Parr apparatus at 60 psig for 3 hours.

The catalyst was removed by filtration and the solvent was evaporated in vacuo. The residue was slurried with ether and extracted with 1% sodium bicarbonate. The bicarbonate extract was acidified with dilute hydrochloric acid and extracted with ethyl acetate. It was dried over anhydrous sodium sulfate and evaporated in vacuo to give a semi-solid residue. The residue was triturated with ether and filtered to give 25 mg. of a pale-yellow solid which was about 70–80% pure by spectral data and analysis.

U.V. $\lambda_{max.}^{THF} = 270$ mm ($\epsilon = 10,351$).
NMR and IR analyses confirmed that the compound produced was the title product.

EXAMPLE 50

When the 7β-amino-3-acetoxymethyl-Δ³-0-2-isocephem-4-carboxylic acid (or ester or salt thereof) in the procedures of Examples 23, 28–30 and 31–47 is replaced by an equimolar amount of 7β-amino-3-formyloxymethyl-Δ³-0-2-isocephem-4-carboxylic acid, 7β-amino-3-hydroxymethyl-Δ³-0-2-isocephem-4-carboxylic acid, 7β-amino-3-bromomethyl-Δ³-0-2-isocephem-4-carboxylic acid, 7β-amino-3-methylsulfonyloxymethyl-Δ³-0-2-isocephem-4-carboxylic acid, 7β-amino-3-carbamoyloxymethyl-Δ³-0-2-isocephem-4-carboxylic acid or 7β-amino-3-benzyloxymethyl-Δ³-0-2-isocephem-4-carboxylic acid (or an ester or salt thereof, any reactive functional groups other than the 7-amino group being suitably protected if necessary), respectively, there are produced (after any necessary de-blocking of functional protecting groups) the corresponding 7β-acylamino carboxylic acids of each of the above-named nuclei.

EXAMPLE 51

When the benzyl 7β-phenoxyacetamido-3-hydroxymethyl-Δ³ -0-2-isocephem-4-carboxylate in the procedure of Example 27 is replaced by an equimolar weight of the benzyl esters of each of the 7β-acylamino-3-hydroxymethyl-Δ³-0-2-isocephem-4-carboxylic acid products of Example 50, there are produced the corresponding 7β-acylamino-3-methylsulfonyloxymethyl-Δ³-0-2-isocephem-4-carboxylate esters of the respective 3-hydroxymethyl compounds.

EXAMPLE 52

When the α-amino products of Examples 30 and 43–44 or 50 are reacted with acetone according to the procedure of U.S. Pat. No. 3,303,193, there are obtained the corresponding 0-2-isocephem derivatives of the formula Table 7

| Organism | | M.I.C. in mcg./ml. | | |
|---|---|---|---|---|
| | | BC-L74 | Cephalexin | Cephalothin |
| D. pneumoniae +5% serum* | A9585 | 16 | 1 | .13 |
| Str. pyogenes +5% serum* | A9604 | 8 | .25 | .06 |
| S. aureus Smith** | A9537 | .5 | 1 | .13 |
| S. aureus Smith** +50% serum | A9537 | >63 | 2 | .5 |
| S. aureus BX1633-2 at 10⁻³ dil'n | A9606 | 1 | 4 | .25 |
| S. aureus BX1633-2 at 10⁻² dil'n | A9606 | >125 | 8 | .5 |
| S. aureus meth.-resist.; at 10⁻³ dil'n | A15097 | 32 | 16 | 1 |
| Sal. enteritidis** | A9531 | >125 | 4 | .25 |
| E. coli Juhl** | A15119 | >125 | 8 | 16 |
| E. coli** | A9675 | >125 | 16 | 63 |
| K. pneumoniae** | A9977 | >125 | 8 | 2 |
| K. pneumoniae** | A15130 | >125 | 16 | 32 |
| Pr. mirabilis** | A9900 | >125 | 8 | 1 |
| Pr. morganii** | A15153 | >125 | >125 | >125 |
| Ps. aeruginosa** | A9343A | >125 | >125 | >125 |
| Ser. marcescens** | A20019 | >125 | >125 | >125 |
| Ent. cloacae | A9656 | >125 | >125 | >125 |
| Ent. cloacae | A9657 | >125 | 4 | 8 |
| Ent. cloacae | A9659 | >125 | >125 | >125 |

*50% Nutrient Broth - 45% Antibiotic Assay Broth
**at 10⁻⁴ dilution.

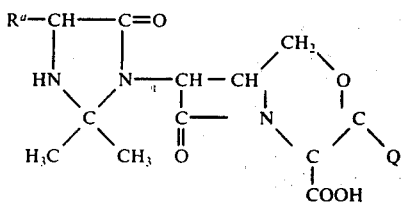

where R$^a$ is as defined in the above-mentioned examples and Q is acetoxymethyl, formyloxymethyl, hydroxymethyl, bromomethyl, methylsulfonyloxymethyl, carbamoyloxymethyl or benzyloxymethyl, or pharmaceutically acceptable salts thereof.

EXAMPLE 53

When the α-amino products of Examples 30, 43–44 or 50 are reacted with dicyanogen or cyanogen bromide or cyanogen chloride according to the procedure disclosed in U.S. Pat. No. 3,796,709, the corresponding α-cyanamino products are obtained.

EXAMPLE 54

When the α-amino products of Examples 30, 43–44 or 50 are reacted with a triethylamine —SO$_3$ complex according to the procedure of U.S. Pat. No. 3,381,001, the corresponding α-sulfoamino products are obtained.

EXAMPLE 55

When the α-amino products of Examples 30, 43–44 or 50 are reacted with 1-methyl-1-nitrosobiuret or a 1-methyl-5-(lower)alkyl-1-nitrosobiuret according to the procedure of U.S. Pat. No. 3,483,188, there are produced the compounds of the general formula

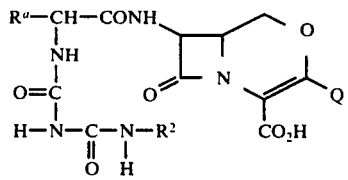

where R$^2$ is hydrogen or (lower)alkyl, Q is acetoxymethyl, formyloxymethyl, bromomethyl, methylsulfonyloxymethyl, carbamoyloxymethyl, benzyloxymethyl or hydroxymethyl and R$^a$ is as defined in the above-mentioned examples.

EXAMPLE 56

Preparation of
7β-[α-(2-Aminomethyl-1,4-cyclohexadienyl)-acetamido]-3-methyl-Δ$^3$-0-2-isocephem-4-carboxylic acid

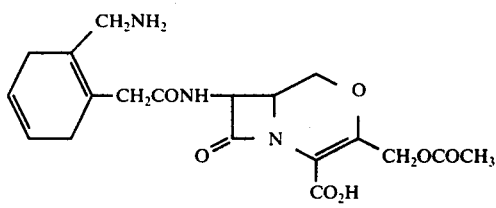

A. α-(2-Aminomethyl-1,4-cyclohexadienyl)acetic acid

A solution of 16.5 g. (0.1 mole) of o-aminomethylphenylacetic acid in 1.5 l of liquid ammonia (which had been treated with 50 mg. of Li to remove a trace of moisture) was slowly diluted with 500 ml. of dry t-BuOH. To the solution was added in small portions 3.4 g. (0.5 atom) of Li over a period of 4 hours and the mixture was stirred for 16 hours at room temperature removing the liquid ammonia in a hood and finally evaporated to dryness below 40° C. The residue was dissolved in 500 ml. of water and the solution was chromatographed on a column of IR-120 (H$^+$,700 ml.) resin and eluted with 1% NH$_4$OH solution. Ninhydrin positive fractions of the eluate were combined and evaporated to dryness. The residue was washed with four 50 ml. portions of hot acetone and recrystallized from 500 ml. of ethanol-water (1:1) to give 11.2 g. (67%) of α-(2-aminomethyl-1,4-cyclohexadienyl)acetic acid as colorless needles. M.p. 183° C IR: $\nu_{max}^{nuj}$ 1630, 1520, 1380, 1356 cm$^{-1}$. NMR: δD$_2$O + K$_2$CO$_3$ 272

(4H, s, H$_2$C 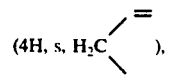 ), 3.01 (2H, s, CH$_2$CO), 3.20 (2H, s, CH$_2$-N), 5.78

(2H, s, 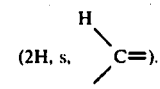 ).

Anal. Calcd. for C$_9$H$_{13}$NO$_2$: C, 64.65; H, 7.84; N, 8.38. Found: C, 64.77; H, 8.06; N, 8.44.

B.
α-[2-(t-Butoxycarbonylaminomethyl)-1,4-cyclohexadienyl]-acetic acid

To a stirred solution of 8.0 g. (0.048 mole) of α-(2-aminomethyl-1,4-cyclohexadienyl)acetic acid and 3.8 g. (0.096 mole) of NaOH in 150 ml. of water was added a solution of 10.3 g. (0.072 mole) of t-butoxycarbonylazide in 80 ml. of THF and the mixture was stirred for 18 hours at room temperature. The THF was removed under reduced pressure and the residual solution was washed with ether (2 × 100 ml.), acidified with 6 N HCl and extracted with ether (3 × 100 ml.). The combined extracts were washed with water (2 × 100 ml.) and a saturated NaCl solution (100 ml.), dried with Na$_2$SO$_4$ and evaporated to dryness. The oily residue was triturated with n-hexane to give 10.5 g. (82%) of colorless powder melting at 113° C.

IR: $\nu_{max}^{nuj}$ 3370, 1715, 1640, 1530, 1280, 1160 cm$^{-1}$. NMR: δ$_{ppm}^{CDCl3}$ 1.45 (9H, s, t-Bu-H), 2.73

(4H, s, H$_2$C 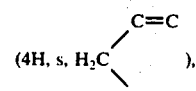 ), 3.16 (2H, s, CH$_2$CO), 3.76 (2H, d, 6Hz, CH$_2$N) 4.90 (1H, m, NH), 5.66

(2H, s, 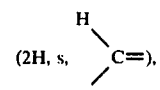 ).

10.6 (1H, br-s, COOH).

Anal. Calcd. for $C_{14}H_{21}NO_4$: C, 62.90; H, 7.92; N, 5.24. Found: C, 63.13; H, 8.21; N, 5.26.

C.
7β-[α-(2-t-Butoxycarbonylaminomethyl-1,4-cyclohexadienyl)-acetamido]-3-acetoxymethyl-Δ³-0-2-isocephem-4-carboxylic acid To a stirred solution of equimolar amounts of α-[2-(t-butoxycarbonylaminomethyl)-1,4-cyclohexadienyl)acetic acid and 2,4-dinitrophenol in ethyl acetate is added an equimolar amount of N,N'-dicyclohexylcarbodiimide. The reaction mixture is stirred at room temperature for 3 hours. The separated dicyclohexylurea is filtered off. The filtrate is evaporated to dryness to give the activated ester which is dissolved in tetrahydrofuran. To this solution is added a solution of 7β-amino-3-acetoxymethyl-Δ³-0-2-isocephem-4-carboxylic acid and triethylamine in approximately a 1:2 molar proportion, respectively, relative to the α-[2-(t-butoxycarbonylaminomethyl)-1,4-cyclohexadienyl]acetic acid. The mixture is stirred at room temperature for several hours and concentrated in vacuo. The concentrate is washed with ether, acidified with dilute mineral acid and extracted with ethyl acetate. The extracts are washed with water and saturated NaCl solution and dried to give the title product.

D.
7β[α-(2-Aminomethyl-1,4-cyclohexadiethyl-)acetamido]-3-acetoxymethyl-Δ³-0-2-isocephem-4-carboxylic acid A solution of 7β-[α-(2-t-butoxycarbonylaminomethyl-1,4-cyclohexadienyl)acetamido]-3-acetoxymethyl-Δ³-0-2-isocephem-4-carboxylic acid in trifluoroacetic acid is stirred at 0° C. for one hour. To the solution is added dry ether until a precipitate forms. The precipitate is collected by filtration, suspended in water and adjusted to pH6 to give the title product.

EXAMPLE 57
7β-[α-(2-Aminomethyl-1-cyclohexenyl)acetamido]-3-acetoxymethyl-Δ³-0-2-isocephem-4-carboxylic acid

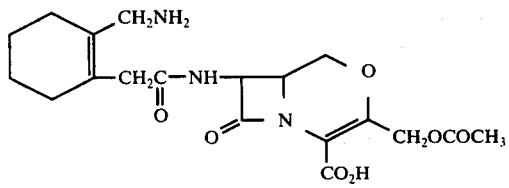

A.
[2-(N-t-Butoxycarbonylaminomethyl)-1-cyclohexen-1-yl]-acetic acid

A solution of α-[2-(t-butoxycarbonylaminomethyl)-1,4-cyclohexadienyl]-acetic acid (1.33 g., 5 mmoles) in 3% ammonium hydroxide (10 ml.) was hydrogenated at 40 psi with palladium on charcoal (10%, 0.2 g.). A theoretical amount of hydrogen was taken up in 3 hours. The catalyst was removed and the filtrate was acidified to pH 2 with dil. HCl and extracted with ethyl acetate (2 × 50 ml.). The combined extracts were washed with water (20 ml.), dried with $Na_2SO_4$ and evaporated under reduced pressure to afford an oil (1.34 g.) which solidified on standing for several days. Recrystallization from n-hexane - ethyl acetate gave 1.2 g. title product as colorless prisms melting at 118°–119° C.

IR: $\nu_{max}^{nujol}$ 3450, 1730, 1660, 1510 cm⁻¹. NMR: $\delta_{ppm}^{CDCl_3}$ 1.58 (9H, s, t-butyl-H), 1.50 - 1.90 (4H, m, —CH₂—), 1.90 - 2.20 (4H, m, allylic methylene-H), 3.18 (2H, s, CH₂-CO), 3.78 (2H, d, 6 Hz, CH₂-N), 5.00 (1H, br-s, NH), 8.98 (1H, br-s, COOH).

Anal. Calcd. for $C_{14}H_{23}NO_4$: C, 62.43; H, 8.61; N, 5.20. Found: C, 62.12; H, 8.77; N, 5.37.

B.
7β-[α-(2-t-Butoxycarbonylaminomethyl-1-cyclohexenyl)acetamido]-3-acetoxymethyl-Δ³-0-2-isocephem-4-carboxylic acid To a stirred solution of equimolar amounts of [2-(N-t-butoxycarbonylaminomethyl)-1-cyclohexen-1-yl]acetic acid and 2,4-dinitrophenol in ethyl acetate is added an equimolar amount of N,N'-dicyclohexylcarbodiimide. The reaction mixture is stirred for 1 hour at room temperature and the precipitated dicyclohexylurea is filtered off. The filtrate is cooled to 5° C. and poured into a cold solution of 7β-amino-3-acetoxymethyl-Δ³-0-2-isocephem-4-carboxylic acid and excess triethylamine in 50% aqueous THF. The mixture is stirred overnight at room temperature and washed with ether. The aqueous layer is acidified with dilute HCl to precipitate the title product.

C.
7β-[α-Aminomethyl-1-cyclohexenyl)acetamido]-3-acetoxymethyl-Δ³-0-2-isocephem-4-carboxylic acid A solution of 7β-[α-(2-t-butoxycarbonylaminomethyl-1-cyclohexenyl)acetamido]-3-acetoxymethyl-Δ³-0-2-isocephem-4-carboxylic acid in trifluoroacetic acid is stirred at 0° C. for 1.5 hours. The mixture is diluted with ether to separate the trifluoroacetate salt which is dissolved in water and neutralized to give the title product.

EXAMPLE 58

When the 7-amino intermediates in the acylation procedures of Examples 23, 26, 28, 30, 31–50, 56 and 57 are replaced by the corresponding pivaloyloxymethyl, acetoxymethyl, methoxymethyl, acetonyl and phenacyl esters, respectively, and the ester group of the 7-acylamido product is not removed, there are obtained the corresponding pivaloyloxymethyl, acetoxymethyl, methoxymethyl, acetonyl and phenacyl esters, respectively, of the 7-acylamido end products.

We claim:
1. A compound having the formula

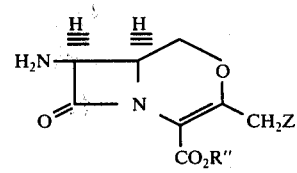

wherein Z is etherified hydroxyl of the formula —OR₃ in which R³ is benzyl or a 5- or 6-membered heterocyclic radical containing 1–4 atoms selected from N, O and S, said heterocyclic radical being optionally substituted by one or more substituents selected from halogen, amino, nitro, $C_1$–$C_4$ alkyl, $C_3$–$C_4$ cycloalkyl, $C_1$–$C_4$ alkoxy, $C_2$–$C_4$ alkenyl, trifluoromethyl, phenyl, benzyl, $C_1$–$C_4$ alkylthio, $C_1$–$C_4$ alkylamino, di $C_1$–$C_4$ alkylamino or alkoxyalkyl of up to 4 carbon atoms and R'' is hydrogen or an easily cleavable ester carboxyl-protecting group selected from benzhydryl, benzyl, p-nitrobenzyl, p-methoxybenzyl, trichloroethyl, trimethylsilyl, phenacyl, acetonyl, (lower)alkyl, triphenylmethyl, methoxymethyl, indanyl, phthalidyl, pivaloyloxymethyl or acetoxymethyl, or a pharmaceutically acceptable salt thereof.

2. A compound of claim 1 wherein $R_3$ is benzyl, 1,2,3-triazolyl, 1,2,4-triazolyl, 1,3,4-thiadiazolyl, 1,2,4-thiadiazolyl, 1,3,4-oxadiazolyl, 1,2,3,4-tetrazolyl, 2-methyl-1,3,4-thiadiazol-5-yl, 2-methyl-1,3,4-oxadiazol-5-yl or 1-N-methyltetrazolyl.

3. An acid of claim 2 wherein $R''$ is hydrogen, or a pharmaceutically acceptable salt thereof.

4. An acid of claim 2 wherein $R''$ is hydrogen.

5. A compound of claim 2 wherein $R''$ is pivaloyloxymethyl, methoxymethyl, indanyl, phthalidyl or acetoxymethyl.

6. The acid of claim 2 wherein $R_3$ is benzyl and $R''$ is hydrogen.

7. The acid of claim 2 wherein $R_3$ is 1-N-methyltetrazol-5-yl and $R''$ is hydrogen.

8. The ester of claim 2 wherein $R_3$ is 1-N-methyltetrazol-5-yl and $R''$ is p-nitrobenzyl.

9. The ester of claim 2 wherein $R_3$ is benzyl and $R''$ is benzyl.

* * * * *